US009593159B2

(12) United States Patent
Kwaks et al.

(10) Patent No.: US 9,593,159 B2
(45) Date of Patent: *Mar. 14, 2017

(54) HUMAN BINDING MOLECULES CAPABLE OF NEUTRALIZING INFLUENZA A VIRUSES OF PHYLOGENETIC GROUP 1 AND PHYLOGENETIC GROUP 2 AND INFLUENZA B VIRUSES

(71) Applicant: Crucell Holland B.V., Leiden (NL)

(72) Inventors: Theodorus Hendrikus Kwaks, Voorschoten (NL); David Adrianus Theodorus Maria Zuijdgeest, The Hague (NL); Ronald Vogels, Linschoten (NL); Robert H. E. Friesen, Leiden (NL)

(73) Assignee: Janssen Vaccines & Prevention B.V., Leiden (NL)

( * ) Notice: Subject to any disclaimer, the term of this patent is extended or adjusted under 35 U.S.C. 154(b) by 0 days.

This patent is subject to a terminal disclaimer.

(21) Appl. No.: 14/597,016

(22) Filed: Jan. 14, 2015

(65) Prior Publication Data
US 2015/0274811 A1    Oct. 1, 2015

Related U.S. Application Data

(63) Continuation of application No. 14/126,404, filed as application No. PCT/EP2012/063637 on Jul. 12, 2012, now Pat. No. 8,961,978.

(60) Provisional application No. 61/572,417, filed on Jul. 14, 2011.

(30) Foreign Application Priority Data

Jul. 14, 2011   (EP) .................................... 11173953

(51) Int. Cl.
| A61K 39/42 | (2006.01) |
| C07K 16/10 | (2006.01) |
| G01N 33/569 | (2006.01) |
| A61K 39/00 | (2006.01) |

(52) U.S. Cl.
CPC .......... C07K 16/1018 (2013.01); A61K 39/42 (2013.01); G01N 33/56983 (2013.01); *A61K 2039/505* (2013.01); *C07K 2317/21* (2013.01); *C07K 2317/33* (2013.01); *C07K 2317/565* (2013.01); *C07K 2317/569* (2013.01); *C07K 2317/622* (2013.01); *C07K 2317/70* (2013.01); *C07K 2317/76* (2013.01); *C07K 2317/92* (2013.01); *G01N 2333/11* (2013.01)

(58) Field of Classification Search
None
See application file for complete search history.

(56) References Cited

U.S. PATENT DOCUMENTS

| 6,265,150 B1 | 7/2001 | Terstappen et al. |
| 2009/0092620 A1 | 4/2009 | Moste et al. |
| 2014/0120113 A1 | 5/2014 | Kwaks et al. |

FOREIGN PATENT DOCUMENTS

| WO | 8403564 A1 | 9/1984 |
| WO | 9309872 A1 | 5/1993 |
| WO | 9815833 A1 | 4/1998 |
| WO | 0063403 A2 | 10/2000 |
| WO | 02103012 A1 | 12/2002 |
| WO | 2008028946 A2 | 3/2008 |
| WO | 2010010466 A2 | 1/2010 |
| WO | 2013007770 A1 | 1/2013 |

OTHER PUBLICATIONS

Sui et al., Structural and functional bases for broad-spectrum neutralization of avian and human influenza A viruses Nature Structural and Molecular Biology, Mar. 1, 2009, pp. 265-273, vol. 16, No. 3, Nature Publishing Group, US.
Lerner, Richard A., Rare antibodies from combinatorial libraries suggests an SOS component of the human immunological repertoire, Molecular Biosystems, Jan. 1, 2011, pp. 1004-1012, vol. 7, No. 4, Royal Society of Chemistry, United Kingdom.
Ekiert et al., Antibody Recognition of a Highly Conserved Influenza Virus Epitope, Science, Apr. 1, 2009, pp. 246-251, vol. 324, No. 5924, American Association for the Advancement of Science, Washington, DC, US.
Smirnov et al., An epitope shared by the hemagglutinins of H1, H2, H5, and H6 subtypes of influenza A virus, ACTA Virologica, Aug. 1, 1999, pp. 237-244, vol. 43, No. 4., Academia Prague, Prague, CS.
Okuno et al., A common Neutralizing Epitope Conserved Between the Hemagglutinins of Influenza A Virus H1 and H2 Strains, Journal of Virology, May 1, 1993, pp. 2552-2558, The American Society for Microbiology, US.
Rudikoff et al., Single amino acid substitution altering antigenbinding specificity, Proceedings of the National Academy of Sciences of USA, Mar. 1, 1982, pp. 1979-1983, vol. 79, National Academy of Science, Washington, DC, US.
Corti et al., Heterosubtypic neutralizing antibodies are produced by individuals immunized with a seasonal influenza vaccine, Journal of Clinical Investigation, May 3, 2010, pp. 1663-1673, vol. 120, No. 5, American Society for Clinical investigation, US.

(Continued)

*Primary Examiner* — Nick Zou
(74) *Attorney, Agent, or Firm* — TraskBritt, P.C.

(57) ABSTRACT

Described are binding molecules, such as human monoclonal antibodies, that bind to an epitope in the stem region of hemagglutinin of influenza A viruses of phylogenetic group 1 and group 2, as well as influenza B viruses, and have a broad neutralizing activity against such influenza viruses. Provided are nucleic acid molecules encoding the binding molecules, their sequences, and compositions comprising the binding molecules. The binding molecules can be used, for example, in the diagnosis, prophylaxis, and/or treatment of influenza A viruses of phylogenetic groups 1 and 2, as well as influenza B viruses.

8 Claims, 4 Drawing Sheets

(56) References Cited

OTHER PUBLICATIONS

PCT International Search Report, PCT/EP2012/063637, dated Dec. 18, 2012.
PCT International Preliminary Report on Patentability, PCT/EP2012/063637 dated Oct. 10, 2013.
Gravel et al., Qualitative and quantitative analyses of virtually all subtypes of influenza A and B viral neuraminidases using antibodies targeting the universally conserved sequences, Vaccine, 2010, pp. 5774-5784, vol. 28.
Chun et al., Universal antibodies and their applications to the quantitative determination of virtually all subtypes of the influenza A viral hemagglutinins. Vaccine. Nov. 11, 2008;26(48):6068-76. doi: 10.1016/j.vaccine.2008.09.015.
Hashem et al., Universal antibodies against the highly conserved influenza fusion peptide cross-neutralize several subtypes of influenza A virus. Biochem Biophys Res Commun. Dec. 10, 2010;403(2):247-51. doi: 10.1016/j.bbrc.2010.11.030. Epub Nov. 13, 2010.
Sun et al., Generation, characterization and epitope mapping of two neutralizing and protective human recombinant antibodies against influenza A H5N1 viruses. PLoS One. 2009;4(5):e5476. Epub May 7, 2009.
Yang et al., Evaluation of diagnostic applications of monoclonal antibodies against avian influenza H7 viruses. Clin Vaccine Immunol. Sep. 2010;17(9):1398-406. Epub Jul. 21, 2010.
Pansri et al., A compact phage display human scFv library for selection of antibodies to a wide variety of antigens. BMC Biotechnol. Jan. 29, 2009;9:6 . . . .
Ekiert et al., A Highly Conserved Neutralizing Epitope on Group 2 Influenza A Viruses. Science. Aug. 12, 2011; 333 (6044):843-850.
Ekiert et al. Antibody recognition of a highly conserved influenza virus epitope: implications for universal prevention and therapy. Science. Apr. 10, 2009; 324(5924): 246-251.

HUMAN BINDING MOLECULES CAPABLE OF NEUTRALIZING INFLUENZA A VIRUSES OF PHYLOGENETIC GROUP 1 AND PHYLOGENETIC GROUP 2 AND INFLUENZA B VIRUSES

CROSS-REFERENCE TO RELATED APPLICATIONS

This application is a continuation of U.S. patent application Ser. No. 14/126,404, filed Dec. 13, 2013, now U.S. Pat. No. 8,961,978, issued Feb. 24, 2015, which application is a national phase entry under 35 U.S.C. §371 of International Patent Application PCT/EP2012/063637, filed Jul. 12, 2012, designating the United States of America and published in English as International Patent Publication WO 2013/007770 A1 on Jan. 17, 2013, which claims the benefit under Article 8 of the Patent Cooperation Treaty and under 35 U.S.C. §119(e) to U.S. Provisional Patent Application Ser. No. 61/572,417, filed Jul. 14, 2011, and to European Patent Application Serial No. 11173953.8, filed Jul. 14, 2011, the contents of the entirety of each of which are incorporated herein by this reference.

TECHNICAL FIELD

The disclosure herein relates to biotechnology and medicine. This disclosure, in particular, relates to human binding molecules able to neutralize influenza A viruses of both phylogenetic group 1 and phylogenetic group 2. In particular, the disclosure relates to binding molecules able to neutralize influenza A viruses of both phylogenetic group 1 and phylogenetic group 2, as well as influenza B viruses. This disclosure further relates to the diagnosis, prophylaxis and/or treatment of an infection caused by influenza A viruses of phylogenetic groups 1 and 2 and, preferably, also influenza B viruses.

STATEMENT ACCORDING TO 37 C.F.R. §1.821(c) or (e)—SEQUENCE LISTING SUBMITTED AS PDF FILE WITH A REQUEST TO TRANSFER CRF FROM PARENT APPLICATION

Pursuant to 37 C.F.R. §1.821(c) or (e), a file containing a PDF version of the Sequence Listing has been submitted concomitant with this application, the contents of which are hereby incorporated by reference. The transmittal documents of this application include a Request to Transfer CRF from the parent application.

BACKGROUND

Influenza infection (also referred to as "influenza" or "the flu") is one of the most common diseases known to man causing between three and five million cases of severe illness and between 250,000 and 500,000 deaths every year around the world. Influenza rapidly spreads in seasonal epidemics affecting 5-15% of the population and the burden on health care costs and lost productivity are extensive (World Healthcare Organization (WHO)).

Three types of influenza virus (types A, B and C) are responsible for infectious pathologies in humans and animals. The type A and type B viruses are the agents responsible for the influenza seasonal epidemics and pandemics observed in humans.

Influenza A viruses can be classified into influenza virus subtypes based upon variations in antigenic regions of two genes that encode the surface glycoproteins hemagglutinin (HA) and neuraminidase (NA), which are required for viral attachment and cellular release. Currently, sixteen subtypes of HA (H1-H16) and nine NA (N1-N9) antigenic variants are known in influenza A virus. Influenza virus subtypes can further be classified by reference to their phylogenetic group. Phylogenetic analysis (Fouchier et al., 2005) has demonstrated a subdivision of HAs comprising two main groups (Air, 1981): inter alia the H1, H2, H5 and H9 subtypes in phylogenetic group 1 (herein also referred to as "group 1") and inter alia the H3, H4 and H7 subtypes in phylogenetic group 2 (or "group 2"). Only some of the influenza A subtypes (i.e., H1N1, H1N2 and H3N2) circulate among people, but all combinations of the 16 HA and 9 NA subtypes have been identified in animals, in particular, in avian species. Animals infected with influenza A often act as a reservoir for the influenza viruses and certain subtypes have been shown to cross the species barrier to humans, such as the highly pathogenic influenza A strain H5N1.

The influenza type B virus strains are strictly human. The antigenic variations in HA within the influenza type B virus strains are weaker than those observed within the type A strains. Two genetically and antigenically distinct lineages of influenza B virus are circulating in humans, as represented by the B/Yamagata/16/88 (also referred to as "B/Yamagata") and B/Victoria/2/87 ("B/Victoria") lineages (Ferguson et al., 2003). Although the spectrum of disease caused by influenza B viruses is generally milder than that caused by influenza A viruses, severe illness requiring hospitalization is still frequently observed with influenza B infection.

Current approaches to dealing with annual influenza epidemics include annual vaccination, preferably generating heterotypic cross-protection. However, circulating influenza viruses in humans are subject to permanent antigenic changes that require annual adaptation of the influenza vaccine formulation to ensure the closest possible match between the influenza vaccine strains and the circulating influenza strains. Although yearly vaccination with influenza vaccines is the best way to prevent influenza, antiviral drugs, such as oseltamivir (TAMIFLU®) can be effective for prevention and treatment of influenza infection. The number of influenza virus strains showing resistance against antiviral drugs, such as oseltamivir is, however, increasing.

An alternative approach is the development of antibody-based prophylactic or therapeutic treatments to neutralize various seasonal and pandemic influenza viruses. The primary target of most neutralizing antibodies that protect against influenza virus infection is the globular head (HA1 part) of the viral HA protein that contains the receptor binding site, but that is subject to continuing genetic evolution with amino acid substitutions in antibody-binding sites (antigenic drift).

Recently, broadly cross-neutralizing antibodies recognizing an epitope in the conserved stem region of hemagglutinin of influenza A viruses of phylogenetic group 1 (including, e.g., the H1 and H5 influenza subtypes) have been identified (see, e.g., WO2008/028946), as well as cross-neutralizing antibodies recognizing a highly conserved epitope in the stem region of HA of influenza A viruses of phylogenetic group 2 (including, e.g., H3 and H7 subtypes) (WO 2010/130636). The neutralizing activity of these antibodies is restricted to either group 1 or group 2 influenza viruses. In addition, these antibodies are not capable of binding to and neutralizing influenza B viruses.

Furthermore, WO 2010/010466 discloses a human antibody F16 binding to hemagglutinin and capable of binding to and neutralizing influenza A subtypes of group 1 (including H1 and H5 subtypes) and group 2 (including H3 and H7 subtypes). This antibody also does not bind HA from influenza B viruses.

In addition, US 2009/0092620 discloses a murine antibody recognizing an antigenic structure present in hemagglutinin of both the H1 and the H3 subtype and on hemagglutinin of influenza B viruses belonging to the B/Victoria and B/Yamagata groups. The antibodies inhibit the hemagglutination activity of several H3N2 strains implicating that this antibody binds an epitope in the globular head of HA.

In view of the severity of the respiratory illness caused by influenza A and influenza B viruses, as well has the high economic impact of the seasonal epidemics and the continuing risk for pandemics, there is an ongoing need for effective means for the prevention and treatment of influenza A and B subtypes. There is thus a need for binding molecules, preferably broadly neutralizing human binding molecules, capable of cross-neutralizing influenza A viruses of both phylogenetic group 1 and phylogenetic group 2, and preferably also influenza B viruses.

DISCLOSURE

Provided are binding molecules able to specifically bind to influenza A virus strains from both phylogenetic group 1 (including, e.g., influenza viruses comprising HA of the H1 and H5 subtype) and influenza A virus strains from phylogenetic group 2 (including, e.g., influenza viruses comprising HA of the H3 and H7 subtype). In certain embodiments, the binding molecules also have neutralizing activity against influenza A virus strains from both phylogenetic group 1 and phylogenetic group 2. In certain embodiments, the binding molecules are furthermore able to specifically bind influenza B virus strains, including, e.g., influenza B virus strains of the B/Yamagata and/or B/Victoria lineages. In certain embodiments, the binding molecules are furthermore able to neutralize influenza B virus strains, including, e.g., influenza B virus strains of the B/Yamagata and/or B/Victoria lineages. In certain embodiments, the binding molecules are capable of in vivo neutralizing influenza A and/or B virus strains. In certain embodiments the binding molecules bind to a conserved epitope in the stem region of the HA protein of influenza A and B viruses. In certain embodiments, the binding molecules have no hemagglutination inhibiting (HI) activity.

Thus provided are binding molecules that bind to an epitope in the stem region of the hemagglutinin protein that is shared between influenza A virus subtypes within the phylogenetic group 1 and influenza virus subtypes within phylogenetic group 2, as well as influenza B virus subtypes, and therefore relates to binding molecules that cross-react between both group 1 and group 2 influenza A virus subtypes and influenza B viruses. The disclosure also pertains to nucleic acid molecules encoding at least the binding region of the human binding molecules.

The binding molecules and/or nucleic acid molecules hereof are suitable for use as a universal prophylactic, diagnostic and/or treatment agent for influenza A viruses and influenza B viruses, even irrespective of the causative influenza subtype.

It is surmised that the binding molecules hereof bind to hitherto unknown and highly conserved epitopes that are not prone to, or much less prone to, antigenic drift or shift. In particular, this epitope is shared between influenza viruses belonging to both phylogenetic group 1 and phylogenetic group 2, and influenza B viruses. Use of the binding molecules hereof to identify and/or characterize these epitopes is also encompassed herein.

Further provided is the use of the human binding molecules and/or the nucleic acid molecules hereof in the diagnosis, prophylaxis and/or treatment of a subject having, or at risk of developing, an influenza virus infection. Furthermore, the disclosure pertains to the use of the human binding molecules and/or the nucleic acid molecules hereof in the diagnosis/detection of such influenza infections.

DETAILED DESCRIPTION

Figure 1A:
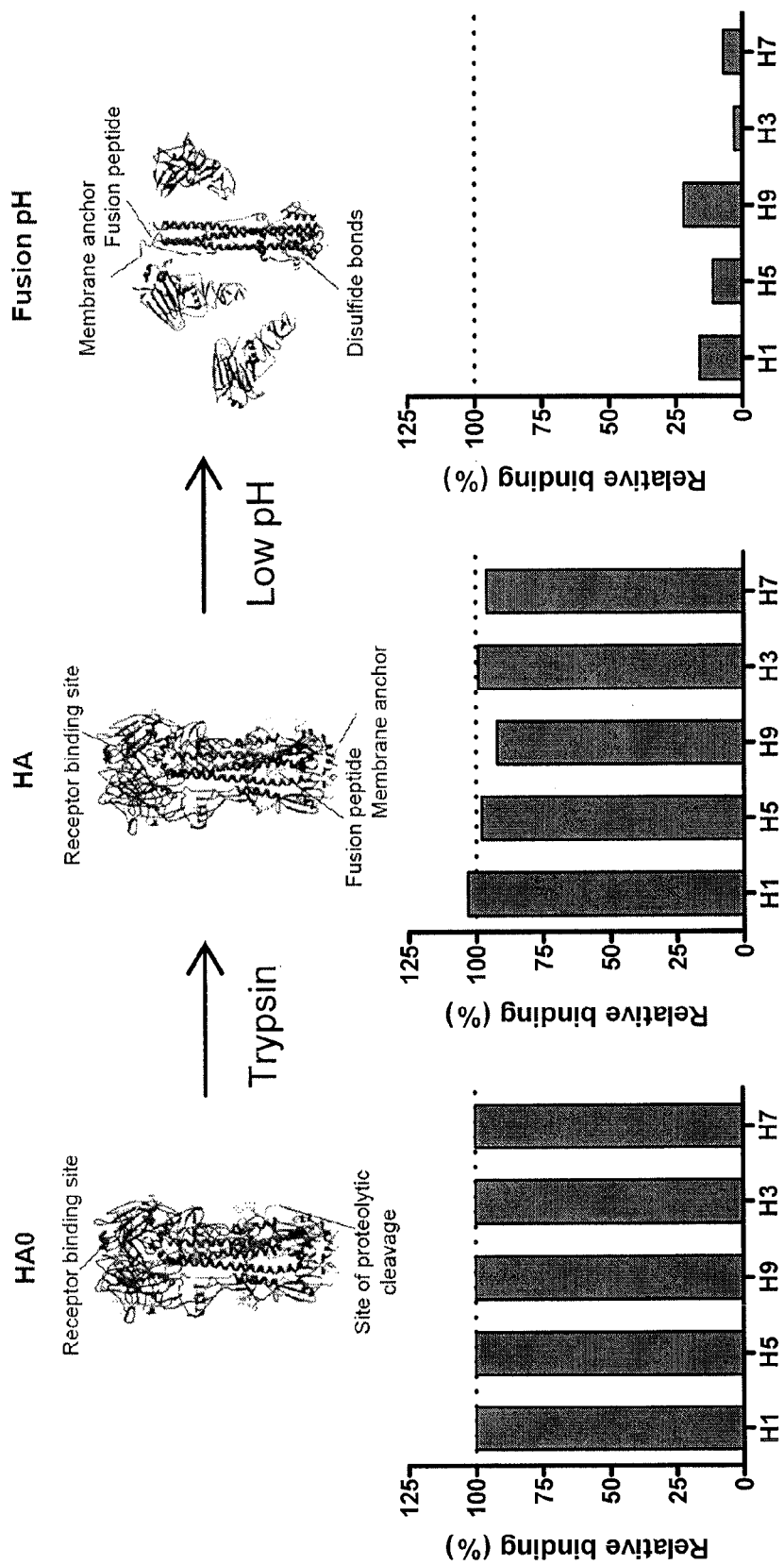
FIG. 1A shows the blocking of conformational change of H1, H5, H9, H3, and H7 HAs by CR9114. Panel A: FACS binding of CR9114 to various conformations—uncleaved precursor (HA0); neutral pH, cleaved (HA); fusion pH, cleaved (fusion pH)—of surface-expressed rHA of A/New Caledonia/20/1999 (H1), A/Viet Nam/1203/2004 (H5), A/Hong Kong/1073/1999 (H9), A/Wisconsin/67/2005 (H3), and A/Netherlands/219/2003 (H7). Binding is expressed as the percentage of binding to untreated rHA (HA0).

Definitions of terms as used in the disclosure described herein are given below.

The term "included" or "including," as used herein, is deemed to be followed by the words "without limitation."

As used herein, the term "binding molecule" refers to an intact immunoglobulin including monoclonal antibodies, such as chimeric, humanized or human monoclonal antibodies, or to an antigen-binding and/or variable domain comprising fragment of an immunoglobulin that competes with the intact immunoglobulin for specific binding to the binding partner of the immunoglobulin, e.g., HA. Regardless of structure, the antigen-binding fragment binds with the same antigen that is recognized by the intact immunoglobulin. An antigen-binding fragment can comprise a peptide or polypeptide comprising an amino acid sequence of at least 2, 5, 10, 15, 20, 25, 30, 35, 40, 50, 60, 70, 80, 90, 100, 125, 150, 175, 200, or 250 contiguous amino acid residues of the amino acid sequence of the binding molecule.

The term "binding molecule," as used herein, includes all immunoglobulin classes and subclasses known in the art. Depending on the amino acid sequence of the constant domain of their heavy chains, binding molecules can be divided into the five major classes of intact antibodies: IgA, IgD, IgE, IgG, and IgM, and several of these may be further divided into subclasses (isotypes), e.g., IgA1, IgA2, IgG1, IgG2, IgG3 and IgG4.

Antigen-binding fragments include, inter alia, Fab, F(ab'), F(ab')2, Fv, dAb, Fd, complementarity-determining region (CDR) fragments, single-chain antibodies (scFv), bivalent single-chain antibodies, single-chain phage antibodies, diabodies, triabodies, tetrabodies, (poly)peptides that contain at least a fragment of an immunoglobulin that is sufficient to confer specific antigen binding to the (poly)peptide, etc. The above fragments may be produced synthetically or by enzymatic or chemical cleavage of intact immunoglobulins or they may be genetically engineered by recombinant DNA techniques. The methods of production are well known in the art and are described, for example, in *Antibodies: A Laboratory Manual*, edited by E. Harlow and D. Lane (1988), Cold Spring Harbor Laboratory, Cold Spring Harbor, N.Y., which is incorporated herein by reference. A binding molecule or antigen-binding fragment thereof may have one or more binding sites. If there is more than one binding site, the binding sites may be identical to one another or they may be different.

The binding molecule can be a "naked" or unconjugated binding molecule, but can also be part of an immunoconjugate. A naked or unconjugated binding molecule is intended to refer to a binding molecule that is not conjugated, operatively linked or otherwise physically or functionally associated with an effector moiety or tag, such as, inter alia, a toxic substance, a radioactive substance, a liposome, or an enzyme. It will be understood that naked or unconjugated binding molecules do not exclude binding molecules that have been stabilized, multimerized, humanized or in any other way manipulated, other than by the attachment of an effector moiety or tag. Accordingly, all post-translationally modified naked and unconjugated binding molecules are included herewith, including where the modifications are made in the natural binding molecule-producing cell environment by a recombinant binding molecule-producing cell, and are introduced by the hand of man after initial binding molecule preparation. The term "naked" or "unconjugated binding molecule" does not exclude the ability of the binding molecule to form functional associations with effector cells and/or molecules after administration to the body, as some of such interactions are necessary in order to exert a biological effect. The lack of associated effector group or tag is, therefore, applied in definition to the naked or unconjugated binding molecule in vitro, not in vivo.

As used herein, the term "biological sample" encompasses a variety of sample types, including blood and other liquid samples of biological origin, solid tissue samples such as a biopsy specimen or tissue cultures, or cells derived therefrom and the progeny thereof. The term also includes samples that have been manipulated in any way after their procurement, such as by treatment with reagents, solubilization, or enrichment for certain components, such as proteins or polynucleotides. The term encompasses various kinds of clinical samples obtained from any species, and also includes cells in culture, cell supernatants and cell lysates.

The term "complementarity-determining regions" (CDR), as used herein, means sequences within the variable regions of binding molecules, such as immunoglobulins, that usually contribute to a large extent to the antigen binding site that is complementary in shape and charge distribution to the epitope recognized on the antigen. The CDR regions can be specific for linear epitopes, discontinuous epitopes, or conformational epitopes of proteins or protein fragments, either as present on the protein in its native conformation or, in some cases, as present on the proteins as denatured, e.g., by solubilization in SDS. Epitopes may also consist of post-translational modifications of proteins.

The term "deletion," as used herein, denotes a change in either amino acid or nucleotide sequence in which one or more amino acid or nucleotide residues, respectively, are absent as compared to the reference, often the naturally occurring, molecule.

The term "expression-regulating nucleic acid sequence," as used herein, refers to polynucleotide sequences necessary for and/or affecting the expression of an operably linked coding sequence in a particular host organism. The expression-regulating nucleic acid sequences, such as, inter alia, appropriate transcription initiation, termination, promoter, enhancer sequences; repressor or activator sequences; efficient RNA processing signals such as splicing and polyadenylation signals; sequences that stabilize cytoplasmic mRNA; sequences that enhance translation efficiency (e.g., ribosome binding sites); sequences that enhance protein stability; and, when desired, sequences that enhance protein secretion, can be any nucleic acid sequence showing activity in the host organism of choice and can be derived from genes encoding proteins, which are either homologous or heterologous to the host organism. The identification and employment of expression-regulating sequences is routine to the person skilled in the art.

The term "functional variant," as used herein, refers to a binding molecule that comprises a nucleotide and/or amino acid sequence that is altered by one or more nucleotides and/or amino acids compared to the nucleotide and/or amino acid sequences of the reference binding molecule and that is capable of competing for binding to the binding partner, i.e., the influenza virus, with the reference binding molecule. In other words, the modifications in the amino acid and/or nucleotide sequence of the reference binding molecule do not significantly affect or alter the binding characteristics of the binding molecule encoded by the nucleotide sequence or containing the amino acid sequence, i.e., the binding molecule is still able to recognize and bind its target. The functional variant may have conservative sequence modifications including nucleotide and amino acid substitutions, additions and deletions. These modifications can be introduced by standard techniques known in the art, such as site-directed mutagenesis and random PCR-mediated mutagenesis, and may comprise natural as well as non-natural nucleotides and amino acids.

Conservative amino acid substitutions include the ones in which the amino acid residue is replaced with an amino acid residue having similar structural or chemical properties. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., asparagine, glutamine, serine, threonine, tyrosine, cysteine, tryptophan), non-polar side chains (e.g., glycine, alanine, valine, leucine, isoleucine, proline, phenylalanine, methionine), beta-branched side chains (e.g., threonine, valine, isoleucine) and aromatic side chains (e.g., tyrosine, phenylalanine, tryptophan). Other classifications of amino acid residue families than the one used above can also be employed. Furthermore, a variant may have non-conservative amino acid substitutions, e.g., replacement of an amino acid with an amino acid residue having different structural or chemical properties. Similar minor variations may also include amino acid deletions or insertions, or both. Guidance in determining which amino acid residues may be substituted, inserted, or deleted without abolishing immunological activity may be found using computer programs well known in the art.

A mutation in a nucleotide sequence can be a single alteration made at a locus (a point mutation), such as transition or transversion mutations or, alternatively, multiple nucleotides may be inserted, deleted or changed at a single locus. In addition, one or more alterations may be made at any number of loci within a nucleotide sequence. The mutations may be performed by any suitable method known in the art.

The term "influenza virus subtype," as used herein, in relation to influenza A viruses refers to influenza A virus variants that are characterized by various combinations of the hemagglutinin (H) and neuramidase (N) viral surface proteins. According to the disclosure, influenza virus subtypes may be referred to by their H number, such as, for example, "influenza virus comprising HA of the H1 or H3 subtype," or "H1 influenza virus," "H3 influenza virus," or by a combination of an H number and an N number, such as, for example, "influenza virus subtype H3N2" or "H3N2."

The term "influenza virus subtype" specifically includes all individual influenza virus "strains" within each subtype, which usually result from mutations and show different pathogenic profiles. Such strains may also be referred to as various "isolates" of a viral subtype. Accordingly, as used herein, the terms "strains" and "isolates" may be used interchangeably. The current nomenclature for human influenza virus strains or isolates includes the geographical location of the first isolation, strain number and year of isolation, usually with the antigenic description of HA and NA given in brackets, e.g., A/Moscow/10/00 (H3N2). Non-human strains also include the host of origin in the nomenclature.

The term "neutralizing," as used herein, in relation to the binding molecules hereof refers to binding molecules that inhibit an influenza virus from replicatively infecting a target cell, regardless of the mechanism by which neutralization is achieved. Thus, neutralization can, e.g., be achieved by inhibiting the attachment or adhesion of the virus to the cell surface, or by inhibition of the fusion of viral and cellular membranes following attachment of the virus to the target cell, and the like.

The term "cross-neutralizing" or "cross-neutralization," as used herein, in relation to the binding molecules hereof refers to the ability of the binding molecules hereof to neutralize different subtypes of influenza A and/or B viruses.

The term "host," as used herein, is intended to refer to an organism or a cell into which a vector such as a cloning vector or an expression vector has been introduced. The organism or cell can be prokaryotic or eukaryotic. Preferably, the hosts isolated host cells, e.g., host cells in culture. The term "host cells" merely signifies that the cells are modified for the (over)-expression of the binding molecules hereof and include B cells that originally express these binding molecules and which cells have been modified to over-express the binding molecule by immortalization, amplification, enhancement of expression, etc. It should be understood that the term "host" is intended to refer not only to the particular subject organism or cell but to the progeny of such an organism or cell as well. Because certain modifications may occur in succeeding generations due to either mutation or environmental influences, such progeny may not, in fact, be identical to the parent organism or cell, but are still included within the scope of the term "host" as used herein.

The term "human," when applied to binding molecules as defined herein, refers to molecules that are either directly derived from a human or based upon a human germ line sequence. When a binding molecule is derived from or based upon a human sequence and subsequently modified, it is still to be considered human as used throughout the specification. In other words, the term "human," when applied to binding molecules, is intended to include binding molecules having variable and constant regions derived from human germline immunoglobulin sequences or based upon variable or constant regions occurring in a human or human lymphocyte and modified in some form. Thus, the human binding molecules may include amino acid residues not encoded by human germline immunoglobulin sequences, comprise substitutions and/or deletions (e.g., mutations introduced by, for instance, random or site-specific mutagenesis in vitro or by somatic mutation in vivo). "Based upon," as used herein, refers to the situation that a nucleic acid sequence may be exactly copied from a template, or with minor mutations, such as by error-prone PCR methods, or synthetically made matching the template exactly or with minor modifications.

The term "insertion," also known as the term "addition," denotes a change in an amino acid or nucleotide sequence resulting in the addition of one or more amino acid or nucleotide residues, respectively, as compared to the parent sequence.

The term "isolated," when applied to binding molecules as defined herein, refers to binding molecules that are substantially free of other proteins or polypeptides, particularly free of other binding molecules having different antigenic specificities, and are also substantially free of other cellular material and/or chemicals. For example, when the binding molecules are recombinantly produced, they are preferably substantially free of culture medium components, and when the binding molecules are produced by chemical synthesis, they are preferably substantially free of chemical precursors or other chemicals, i.e., they are separated from chemical precursors or other chemicals that are involved in the synthesis of the protein. The term "isolated," when applied to nucleic acid molecules encoding binding molecules as defined herein, is intended to refer to nucleic acid molecules in which the nucleotide sequences encoding the binding molecules are free of other nucleotide sequences, particularly nucleotide sequences encoding binding molecules that bind other binding partners. Furthermore, the term "isolated" refers to nucleic acid molecules that are substantially separated from other cellular components that naturally accompany the native nucleic acid molecule in its natural host, e.g., ribosomes, polymerases, or genomic sequences with which it is naturally associated. Moreover, "isolated" nucleic acid molecules, such as cDNA molecules, can be substantially free of other cellular material or culture medium when produced by recombinant techniques, or substantially free of chemical precursors or other chemicals when chemically synthesized.

The term "monoclonal antibody," as used herein, refers to a preparation of antibody molecules of single specificity. A monoclonal antibody displays a single binding specificity and affinity for a particular epitope. Accordingly, the term "human monoclonal antibody" refers to an antibody displaying a single binding specificity that has variable and constant regions derived from or based upon human germline immunoglobulin sequences or derived from completely synthetic sequences. The method of preparing the monoclonal antibody is not relevant for the binding specificity.

The term "naturally occurring," as used herein, as applied to an object refers to the fact that an object or compound can be found in nature. For example, a polypeptide or polynucleotide sequence that is present in an organism that can be isolated from a source in nature and that has not been intentionally modified by man in the laboratory is naturally occurring.

The term "nucleic acid molecule," as used herein, refers to a polymeric form of nucleotides and includes both sense and anti-sense strands of RNA, cDNA, genomic DNA, and synthetic forms and mixed polymers of the above. A nucleotide refers to a ribonucleotide, deoxynucleotide or a modified form of either type of nucleotide. The term also includes single- and double-stranded forms of DNA. In addition, a polynucleotide may include either or both naturally occurring and modified nucleotides linked together by naturally occurring and/or non-naturally occurring nucleotide linkages. The nucleic acid molecules may be modified chemically or biochemically or may contain non-natural or derivatized nucleotide bases, as will be readily appreciated by those of skill in the art. Such modifications include, for example, labels, methylation, substitution of one or more of the naturally occurring nucleotides with an analogue, internucleotide modifications such as uncharged linkages (e.g., methyl phosphonates, phosphotriesters, phosphoramidates, carbamates, etc.), charged linkages (e.g., phosphorothioates, phosphorodithioates, etc.), pendent moieties (e.g., polypeptides), intercalators (e.g., acridine, psoralen, etc.), chelators, alkylators, and modified linkages (e.g., alpha anomeric nucleic acids, etc.) The above term is also intended to include any topological conformation, including single-stranded, double-stranded, partially duplexed, triplex, hairpinned, circular and padlocked conformations. Also included are synthetic molecules that mimic polynucleotides in their ability to bind to a designated sequence via hydrogen bonding and other chemical interactions. Such molecules are known in the art and include, for example, those in which peptide linkages substitute for phosphate linkages in the backbone of the molecule. A reference to a nucleic acid sequence encompasses its complement unless otherwise specified. Thus, a reference to a nucleic acid molecule having a particular sequence should be understood to encompass its complementary strand, with its complementary sequence. The complementary strand is also useful, e.g., for anti-sense therapy, hybridization probes and PCR primers.

The term "operably linked" refers to two or more nucleic acid sequence elements that are usually physically linked and are in a functional relationship with each other. For instance, a promoter is operably linked to a coding sequence if the promoter is able to initiate or regulate the transcription or expression of a coding sequence, in which case, the coding sequence should be understood as being "under the control of" the promoter.

By "pharmaceutically acceptable excipient" is meant any inert substance that is combined with an active molecule, such as a drug, agent, or binding molecule, for preparing an agreeable or convenient dosage form. The "pharmaceutically acceptable excipient" is an excipient that is non-toxic to recipients at the used dosages and concentrations, and is compatible with other ingredients of the formulation comprising the drug, agent or binding molecule. Pharmaceutically acceptable excipients are widely applied and known in the art.

The term "specifically binding," as used herein, in reference to the interaction of a binding molecule, e.g., an antibody, and its binding partner, e.g., an antigen, means that the interaction is dependent upon the presence of a particular structure, e.g., an antigenic determinant or epitope, on the binding partner. In other words, the antibody preferentially binds or recognizes the binding partner even when the binding partner is present in a mixture of other molecules or organisms. The binding may be mediated by covalent or non-covalent interactions or a combination of both. In other words, the term "specifically binding" further means immunospecifically binding to an antigenic determinant or epitope and not immunospecifically binding to other antigenic determinants or epitopes. A binding molecule that immunospecifically binds to an antigen may bind to other peptides or polypeptides with lower affinity as determined by, e.g., radioimmunoassay (RIA), enzyme-linked immunosorbent assay (ELISA), BIACORE, or other assays known in the art. Binding molecules or fragments thereof that immunospecifically bind to an antigen may be cross-reactive with related antigens carrying the same epitope. Preferably, binding molecules or fragments thereof that immunospecifically bind to an antigen do not cross-react with other antigens.

A "substitution," as used herein, denotes the replacement of one or more amino acids or nucleotides by different amino acids or nucleotides, respectively.

The term "therapeutically effective amount" refers to an amount of the binding molecule as defined herein that is effective for preventing, ameliorating and/or treating a condition resulting from infection with an influenza B virus. "Amelioration," as used in herein, may refer to the reduction of visible or perceptible disease symptoms, viremia, or any other measurable manifestation of influenza infection.

The term "treatment" refers to therapeutic treatment as well as prophylactic or preventative measures to cure or halt or at least retard disease progress. Those in need of treatment include those already inflicted with a condition resulting from infection with influenza virus as well as those in which infection with influenza virus is to be prevented. Subjects partially or totally recovered from infection with influenza virus might also be in need of treatment. Prevention encompasses inhibiting or reducing the spread of influenza virus or inhibiting or reducing the onset, development or progression of one or more of the symptoms associated with infection with influenza virus.

The term "vector" denotes a nucleic acid molecule into which a second nucleic acid molecule can be inserted for introduction into a host where it will be replicated, and in some cases, expressed. In other words, a vector is capable of transporting a nucleic acid molecule to which it has been linked. Cloning as well as expression vectors are contemplated by the term "vector," as used herein. Vectors include, but are not limited to, plasmids, cosmids, bacterial artificial chromosomes (BAC) and yeast artificial chromosomes (YAC) and vectors derived from bacteriophages or plant or animal (including human) viruses. Vectors comprise an origin of replication recognized by the proposed host and in the case of expression vectors, promoter and other regulatory regions recognized by the host. A vector containing a second nucleic acid molecule is introduced into a cell by transformation, transfection, or by making use of viral entry mechanisms. Certain vectors are capable of autonomous replication in a host into which they are introduced (e.g., vectors having a bacterial origin of replication can replicate in bacteria). Other vectors can be integrated into the genome of a host upon introduction into the host, and thereby are replicated along with the host genome.

In a first aspect, the disclosure encompasses binding molecules able to specifically bind to hemagglutinin (HA) of influenza A virus subtypes of phylogenetic group 1 and influenza A virus subtypes of phylogenetic group 2. In certain embodiments, the binding molecules are able to neutralize influenza A virus subtypes of both phylogenetic group 1 and phylogenetic group 2. The binding molecules hereof thus are unique in that they are capable of cross-neutralizing group 1 influenza A virus strains and group 2 influenza A virus strains. In certain embodiments, the binding molecules are able to neutralize at least one or more, preferably two or more, preferably three or more, preferably four or more, even more preferably, five or more group 1 influenza A virus subtypes selected from the group consisting of the H1, H2, H5, H6, H8, H9 and H11 subtype, and at least one or more, preferably two or more, preferably three or more group 2 influenza A virus subtypes selected from the group consisting of the H3, H4, H7, and H10 subtype. In certain embodiments, the binding molecules are able to specifically bind to hemagglutinin (HA) of influenza B virus subtypes. In another embodiment, the binding molecules are able to neutralize influenza B viruses. In certain embodiments, the binding molecules are capable of in vivo neutralizing influenza A and/or B viruses. The influenza A and B virus strains may be both human and non-human influenza virus strains (i.e., obtained from non-human animals, e.g., birds).

Preferably, the binding molecules are human binding molecules. In certain embodiments, the binding molecules are human antibodies, or antigen-binding fragments thereof.

In certain embodiments, the binding molecules are derived from the VH1-69 germ line gene. Thus, the binding molecules all use the same VH1-69 germ line-encoded framework.

In certain embodiments, the binding interaction of the binding molecules, preferably the antibody, and HA is mediated exclusively by heavy chain variable sequences.

In certain embodiments, the binding molecules comprise a heavy chain CDR1 comprising the amino acid sequence of SEQ ID NO:133 or SEQ ID NO:139, a heavy chain CDR2 comprising the amino acid sequence of SEQ ID NO:134, SEQ ID NO:140 or SEQ ID NO:151, and a heavy chain CDR3 comprising an amino acid sequence selected from the group consisting of SEQ ID NO:135, SEQ ID NO:141, SEQ ID NO:145, SEQ ID NO:152, SEQ ID NO:161, and SEQ ID NO:162. The CDR regions of binding molecules hereof are shown in Table 7. CDR regions are according to Kabat et al. (1991) as described in *Sequences of Proteins of Immunological Interest.*

Influenza viruses infect cells by binding to sialic acid residues on the cell surface of target cells, and following transfer into endosomes, by fusing their membranes with the endosomal membranes and releasing the genome-transcriptase complex into the cell. Both receptor binding and membrane fusion process are mediated by the HA glycoprotein. The HA of influenza virus A comprises two structurally distinct regions, i.e., a globular head region, which contains a receptor binding site that is responsible for virus attachment to the target cell, and is involved in the hemagglutination activity of HA, and a stem region, containing a fusion peptide, which is necessary for membrane fusion between the viral envelope and the endosomal membrane of the cell. The HA protein is a trimer in which each monomer consists of two disulphide-linked glycopolypeptides, HA1 and HA2, that are produced during infection by proteolytic cleavage of a precursor (HA0). Cleavage is necessary for virus infectivity since it is required to prime the HA for membrane fusion to allow conformational change. Activation of the primed molecule occurs at low pH in endosomes, between pH5 and pH6, and requires extensive changes in HA structure. Each of the stages in the priming and activation of HA for its participation in the membrane fusion process, presents a different target for inhibition, e.g., by monoclonal antibodies. In certain embodiments, the binding molecules are capable of blocking the pH-induced conformational changes in HA associated with membrane fusion.

The binding molecules hereof may be able to specifically bind to the HA0, HA1 and/or HA2 subunit of the HA protein. They may be able to specifically bind to linear or structural and/or conformational epitopes on the HA0, HA1 and/or HA2 subunit of the HA protein. The HA molecule may be purified from viruses or recombinantly produced and optionally isolated before use. Alternatively, HA may be expressed on the surface of cells. In certain embodiments, the binding molecules hereof are able to specifically bind to an epitope in the stem region of HA. In certain embodiments, the binding molecules bind to an epitope that is accessible in the pre-fusion conformation of HA.

The binding molecules hereof may be able to specifically bind to influenza viruses that are viable, living and/or infective or that are in inactivated/attenuated form. Methods for inactivating/attenuating virus, e.g., influenza viruses are well known in the art and include, but are not limited to, treatment with formalin, β-propiolactone (BPL), merthiolate, and/or ultraviolet light.

The binding molecules hereof may also be able to specifically bind to one or more fragments of the influenza viruses, such as, inter alia, a preparation of one or more proteins and/or (poly)peptides derived from subtypes of influenza A and/or B viruses or one or more recombinantly produced proteins and/or polypeptides of influenza A and/or B viruses. The nucleotide and/or amino acid sequence of proteins of various influenza A and B strains can be found in the GenBank-database, NCBI Influenza Virus Sequence Database, Influenza Sequence Database (ISD), EMBL-database and/or other databases. It is well within the reach of the skilled person to find such sequences in the respective databases.

In another embodiment, the binding molecules hereof are able to specifically bind to a fragment of the above-mentioned proteins and/or polypeptides, wherein the fragment at least comprises an epitope recognized by the binding molecules hereof. An "epitope," as used herein, is a moiety that is capable of binding to a binding molecule of the disclosure with sufficiently high affinity to form a detectable antigen-binding molecule complex.

The binding molecules hereof may or may not be able to specifically bind to the extracellular part of HA (also called herein "soluble HA" ("sHA")).

The binding molecules hereof can be intact immunoglobulin molecules, such as polyclonal or monoclonal antibodies, or the binding molecules can be antigen-binding fragments thereof, including, but not limited to, heavy and light chain variable regions, Fab, F(ab'), F(ab')$_2$, Fv, dAb, Fd, complementarity-determining region (CDR) fragments, single-chain antibodies (scFv), bivalent single-chain antibodies, single-chain phage antibodies, diabodies, triabodies, tetrabodies, and (poly)peptides that contain at least a fragment of an immunoglobulin that is sufficient to confer specific antigen binding to influenza virus strains or a fragment thereof. In a preferred embodiment, the binding molecules hereof are human monoclonal antibodies, and/or antigen-binding fragments thereof. The binding molecules may also be nanobodies, alphabodies, affibodies, FN3-domain scaffolds and other scaffolds based upon domains in (human) repeat proteins like Adnectins, Anticalins, Darpins, etc., or other scaffolds comprising epitope binding sequences.

The binding molecules hereof can be used in non-isolated or isolated form. Furthermore, the binding molecules hereof can be used alone or in a mixture comprising at least one binding molecule (or variant or fragment thereof) of the disclosure, and/or with other binding molecules that bind to influenza and have influenza virus-inhibiting effect. In other words, the binding molecules can be used in combination, e.g., as a pharmaceutical composition comprising two or more binding molecules hereof, variants or fragments thereof. For example, binding molecules having different, but complementary, activities can be combined in a single therapy to achieve a desired prophylactic, therapeutic or diagnostic effect, but alternatively, binding molecules having identical activities can also be combined in a single therapy to achieve a desired prophylactic, therapeutic or diagnostic effect. Optionally, the mixture further comprises at least one other therapeutic agent. Preferably, the therapeutic agent such as, e.g., M2 inhibitors (e.g., amantidine, rimantadine) and/or neuraminidase inhibitors (e.g., zanamivir, oseltamivir) is useful in the prophylaxis and/or treatment of an influenza virus infection.

Typically, binding molecules hereof can bind to their binding partners, i.e., an influenza A virus of group 1 (such as H1N1) and an influenza A virus of group 2 (such as H3N2), and/or an influenza B virus, and/or fragments thereof, with an affinity constant ($K_d$-value) that is lower than $0.2 \times 10^{-4}$ M, $1.0 \times 10^{-5}$ M, $1.0 \times 10^{-6}$ M, $1.0 \times 10^{-7}$ M, preferably lower than $1.0 \times 10^{-8}$ M, more preferably lower than $1.0 \times 10^{-9}$ M, more preferably lower than $1.0 \times 10^{-10}$ M, even more preferably lower than $1.0 \times 10^{-11}$ M, and, in particular, lower than $1.0 \times 10^{-12}$ M. The affinity constants can vary for antibody isotypes. For example, affinity binding for an IgM isotype refers to a binding affinity of at least about $1.0 \times 10^{-7}$ M. Affinity constants can, for instance, be measured using surface plasmon resonance, for example, using the BIACORE system (Pharmacia Biosensor AB, Uppsala, Sweden).

The binding molecules hereof exhibit neutralizing activity. Neutralizing activity can, for instance, be measured as described herein. Alternative assays measuring neutralizing activity are described in, for instance, *WHO Manual on Animal Influenza Diagnosis and Surveillance*, Geneva: World Health Organisation, 2005, version 2002.5.

Typically, the binding molecules hereof have a neutralizing activity of 50 µg/ml or less, preferably 20 µg/ml or less, more preferably a neutralizing activity of 10 µg/ml or less, even more preferably 5 µg/ml or less, as determined in an in vitro virus neutralization assay (VNA) as described in Example 6. The binding molecules hereof may bind to influenza virus or a fragment thereof in soluble form such as, for instance, in a sample or in suspension or may bind to influenza viruses or fragments thereof bound or attached to a carrier or substrate, e.g., microtiter plates, membranes and beads, etc. Carriers or substrates may be made of glass, plastic (e.g., polystyrene), polysaccharides, nylon, nitrocellulose, or TEFLON®, etc. The surface of such supports may be solid or porous and of any convenient shape. Furthermore, the binding molecules may bind to influenza virus in purified/isolated or non-purified/non-isolated form.

As discussed above, the disclosure relates to isolated human binding molecules that are able to recognize and bind to an epitope in the influenza hemagglutinin protein (HA) wherein the binding molecules have neutralizing activity against influenza A viruses of phylogenetic group 1 and influenza A viruses of phylogenetic group 2. It thus has been shown that the binding molecules hereof cross-neutralize influenza virus subtypes belonging to both phylogenetic groups. The skilled person, based upon what has been disclosed herein, can determine whether an antibody indeed cross-reacts with HA proteins from different subtypes and can also determine whether they are able to neutralize influenza viruses of different subtypes in vitro and/or in vivo.

In certain embodiments, the binding molecule hereof is selected from the group consisting of:
  a) a binding molecule comprising a heavy chain CDR1 region of SEQ ID NO:133, a heavy chain CDR2 region of SEQ ID NO:134, and a heavy chain CDR3 region of SEQ ID NO:135;
  b) a binding molecule comprising a heavy chain CDR1 region of SEQ ID NO:139, a heavy chain CDR2 region of SEQ ID NO:140, and a heavy chain CDR3 region of SEQ ID NO:141;
  c) a binding molecule comprising a heavy chain CDR1 region of SEQ ID NO:139, a heavy chain CDR2 region of SEQ ID NO:134, and a heavy chain CDR3 region of SEQ ID NO:145;
  d) a binding molecule comprising a heavy chain CDR1 region of SEQ ID NO:139, a heavy chain CDR2 region of SEQ ID NO:151, and a heavy chain CDR3 region of SEQ ID NO:152;
  e) a binding molecule comprising a heavy chain CDR1 region of SEQ ID NO:139, a heavy chain CDR2 region of SEQ ID NO:134, and a heavy chain CDR3 region of SEQ ID NO:152;
  f) a binding molecule comprising a heavy chain CDR1 region of SEQ ID NO:139, a heavy chain CDR2 region of SEQ ID NO:151, and a heavy chain CDR3 region of SEQ ID NO:161;
  g) a binding molecule comprising a heavy chain CDR1 region of SEQ ID NO:139, a heavy chain CDR2 region of SEQ ID NO:151, and a heavy chain CDR3 region of SEQ ID NO:162; and
  h) a binding molecule comprising a heavy chain CDR1 region of SEQ ID NO:139, a heavy chain CDR2 region of SEQ ID NO:134, and a heavy chain CDR3 region of SEQ ID NO:141.

In certain embodiments, the binding molecule comprises a heavy chain CDR1 region comprising the amino acid sequence of SEQ ID NO:139, a heavy chain CDR2 region comprising an amino acid sequence of SEQ ID NO:134, and a heavy chain CDR3 region comprising the amino acid sequence of SEQ ID NO:145 or SEQ ID NO:152.

In another embodiment, the human binding molecules hereof are selected from the group consisting of:
  a) a binding molecule having a heavy chain CDR1 region of SEQ ID NO:133, a heavy chain CDR2 region of SEQ ID NO:134, and a heavy chain CDR3 region of SEQ ID NO:135, a light chain CDR1 region having the amino acid sequence of SEQ ID NO:136, a light chain CDR2 region having the amino acid sequence of SEQ ID NO:137, and a light chain CDR3 region having the amino acid sequence of SEQ ID NO:138;
  b) a binding molecule comprising a heavy chain CDR1 region of SEQ ID NO:139, a heavy chain CDR2 region of SEQ ID NO:140, and a heavy chain CDR3 region of SEQ ID NO:141, a light chain CDR1 region having the amino acid sequence of SEQ ID NO:142, a light chain CDR2 region having the amino acid sequence of SEQ ID NO:143, and a light chain CDR3 region having the amino acid sequence of SEQ ID NO:144;

c) a binding molecule comprising a heavy chain CDR1 region of SEQ ID NO:139, a heavy chain CDR2 region of SEQ ID NO:134, and a heavy chain CDR3 region of SEQ ID NO:145, a light chain CDR1 region having the amino acid sequence of SEQ ID NO:146, a light chain CDR2 region having the amino acid sequence of SEQ ID NO:174, and a light chain CDR3 region having the amino acid sequence of SEQ ID NO:147;

d) a binding molecule comprising a heavy chain CDR1 region of SEQ ID NO:139, a heavy chain CDR2 region of SEQ ID NO:134, and a heavy chain CDR3 region of SEQ ID NO:145, a light chain CDR1 region having the amino acid sequence of SEQ ID NO:148, a light chain CDR2 region having the amino acid sequence of SEQ ID NO:149, and a light chain CDR3 region having the amino acid sequence of SEQ ID NO:150;

e) a binding molecule comprising a heavy chain CDR1 region of SEQ ID NO:139, a heavy chain CDR2 region of SEQ ID NO:151, and a heavy chain CDR3 region of SEQ ID NO:152, a light chain CDR1 region having the amino acid sequence of SEQ ID NO:153, a light chain CDR2 region having the amino acid sequence of SEQ ID NO:154, and a light chain CDR3 region having the amino acid sequence of SEQ ID NO:155;

f) a binding molecule comprising a heavy chain CDR1 region of SEQ ID NO:139, a heavy chain CDR2 region of SEQ ID NO:134, and a heavy chain CDR3 region of SEQ ID NO:152, a light chain CDR1 region having the amino acid sequence of SEQ ID NO:148, a light chain CDR2 region having the amino acid sequence of SEQ ID NO:149, and a light chain CDR3 region having the amino acid sequence of SEQ ID NO:150;

g) a binding molecule comprising a heavy chain CDR1 region of SEQ ID NO:139, a heavy chain CDR2 region of SEQ ID NO:134, and a heavy chain CDR3 region of SEQ ID NO:152, a light chain CDR1 region having the amino acid sequence of SEQ ID NO:156, a light chain CDR2 region having the amino acid sequence of SEQ ID NO:157, and a light chain CDR3 region having the amino acid sequence of SEQ ID NO:158;

h) a binding molecule comprising a heavy chain CDR1 region of SEQ ID NO:139, a heavy chain CDR2 region of SEQ ID NO:134, and a heavy chain CDR3 region of SEQ ID NO:152, a light chain CDR1 region having the amino acid sequence of SEQ ID NO:148, a light chain CDR2 region having the amino acid sequence of SEQ ID NO:159, and a light chain CDR3 region having the amino acid sequence of SEQ ID NO:160;

i) a binding molecule comprising a heavy chain CDR1 region of SEQ ID NO:139, a heavy chain CDR2 region of SEQ ID NO:151, and a heavy chain CDR3 region of SEQ ID NO:161, a light chain CDR1 region having the amino acid sequence of SEQ ID NO:142, a light chain CDR2 region having the amino acid sequence of SEQ ID NO:143, and a light chain CDR3 region having the amino acid sequence of SEQ ID NO:144;

j) a binding molecule comprising a heavy chain CDR1 region of SEQ ID NO:139, a heavy chain CDR2 region of SEQ ID NO:151, and a heavy chain CDR3 region of SEQ ID NO:162, a light chain CDR1 region having the amino acid sequence of SEQ ID NO:163, a light chain CDR2 region having the amino acid sequence of SEQ ID NO:164, and a light chain CDR3 region having the amino acid sequence of SEQ ID NO:165;

k) a binding molecule comprising a heavy chain CDR1 region of SEQ ID NO:139, a heavy chain CDR2 region of SEQ ID NO:134, and a heavy chain CDR3 region of SEQ ID NO:152, a light chain CDR1 region having the amino acid sequence of SEQ ID NO:166, a light chain CDR2 region having the amino acid sequence of SEQ ID NO:167, and a light chain CDR3 region having the amino acid sequence of SEQ ID NO:168;

l) a binding molecule comprising a heavy chain CDR1 region of SEQ ID NO:139, a heavy chain CDR2 region of SEQ ID NO:134, and a heavy chain CDR3 region of SEQ ID NO:152, a light chain CDR1 region having the amino acid sequence of SEQ ID NO:169, a light chain CDR2 region having the amino acid sequence of SEQ ID NO:149, and a light chain CDR3 region having the amino acid sequence of SEQ ID NO:150;

m) a binding molecule comprising a heavy chain CDR1 region of SEQ ID NO:139, a heavy chain CDR2 region of SEQ ID NO:134, and a heavy chain CDR3 region of SEQ ID NO:141, a light chain CDR1 region having the amino acid sequence of SEQ ID NO:163, a light chain CDR2 region having the amino acid sequence of SEQ ID NO:169, and a light chain CDR3 region having the amino acid sequence of SEQ ID NO:170;

n) a binding molecule comprising a heavy chain CDR1 region of SEQ ID NO:139, a heavy chain CDR2 region of SEQ ID NO:134, and a heavy chain CDR3 region of SEQ ID NO:152, a light chain CDR1 region having the amino acid sequence of SEQ ID NO:171, a light chain CDR2 region having the amino acid sequence of SEQ ID NO:164, and a light chain CDR3 region having the amino acid sequence of SEQ ID NO:172;

o) a binding molecule comprising a heavy chain CDR1 region of SEQ ID NO:139, a heavy chain CDR2 region of SEQ ID NO:134, and a heavy chain CDR3 region of SEQ ID NO:145, a light chain CDR1 region having the amino acid sequence of SEQ ID NO:142, a light chain CDR2 region having the amino acid sequence of SEQ ID NO:143, and a light chain CDR3 region having the amino acid sequence of SEQ ID NO:173; and p) a binding molecule comprising a heavy chain CDR1 region of SEQ ID NO:139, a heavy chain CDR2 region of SEQ ID NO:134, and a heavy chain CDR3 region of SEQ ID NO:152, a light chain CDR1 region having the amino acid sequence of SEQ ID NO:142, a light chain CDR2 region having the amino acid sequence of SEQ ID NO:143, and a light chain CDR3 region having the amino acid sequence of SEQ ID NO:144.

In another embodiment, the human binding molecules hereof are selected from the group consisting of:

a) a binding molecule comprising a heavy chain CDR1 region of SEQ ID NO:139, a heavy chain CDR2 region of SEQ ID NO:134, and a heavy chain CDR3 region of SEQ ID NO:145, a light chain CDR1 region having the amino acid sequence of SEQ ID NO:146, a light chain CDR2 region having the amino acid sequence of SEQ ID NO:174, and a light chain CDR3 region having the amino acid sequence of SEQ ID NO:147;

b) a binding molecule comprising a heavy chain CDR1 region of SEQ ID NO:139, a heavy chain CDR2 region of SEQ ID NO:134, and a heavy chain CDR3 region of SEQ ID NO:152, a light chain CDR1 region having the amino acid sequence of SEQ ID NO:171, a light chain CDR2 region having the amino acid sequence of SEQ ID NO:164, and a light chain CDR3 region having the amino acid sequence of SEQ ID NO:172;
c) a binding molecule comprising a heavy chain CDR1 region of SEQ ID NO:139, a heavy chain CDR2 region of SEQ ID NO:134, and a heavy chain CDR3 region of SEQ ID NO:145, a light chain CDR1 region having the amino acid sequence of SEQ ID NO:142, a light chain CDR2 region having the amino acid sequence of SEQ ID NO:143, and a light chain CDR3 region having the amino acid sequence of SEQ ID NO:173; and
d) a binding molecule comprising a heavy chain CDR1 region of SEQ ID NO:139, a heavy chain CDR2 region of SEQ ID NO:134, and a heavy chain CDR3 region of SEQ ID NO:152, a light chain CDR1 region having the amino acid sequence of SEQ ID NO:142, a light chain CDR2 region having the amino acid sequence of SEQ ID NO:143, and a light chain CDR3 region having the amino acid sequence of SEQ ID NO:144.

In another embodiment, the binding molecule according to this disclosure is selected from the group consisting of:
a) a binding molecule comprising a heavy chain variable region of SEQ ID NO:2;
b) a binding molecule comprising a heavy chain variable region of SEQ ID NO:6;
c) a binding molecule comprising a heavy chain variable region of SEQ ID NO:10;
d) a binding molecule comprising a heavy chain variable region of SEQ ID NO:14;
e) a binding molecule comprising a heavy chain variable region of SEQ ID NO:18;
f) a binding molecule comprising a heavy chain variable region of SEQ ID NO:22;
g) a binding molecule comprising a heavy chain variable region of SEQ ID NO:26;
h) a binding molecule comprising a heavy chain variable region of SEQ ID NO:30;
i) a binding molecule comprising a heavy chain variable region of SEQ ID NO:34;
j) a binding molecule comprising a heavy chain variable region of SEQ ID NO:38;
k) a binding molecule comprising a heavy chain variable region of SEQ ID NO:42;
l) a binding molecule comprising a heavy chain variable region of SEQ ID NO:46;
m) a binding molecule comprising a heavy chain variable region of SEQ ID NO:50;
n) a binding molecule comprising a heavy chain variable region of SEQ ID NO:54;
o) a binding molecule comprising a heavy chain variable region of SEQ ID NO:58; and
p) a binding molecule comprising a heavy chain variable region of SEQ ID NO:62.

In certain embodiments, the binding molecule hereof is selected from the group consisting of a binding molecule comprising a heavy chain variable region of SEQ ID NO:10, a binding molecule comprising a heavy chain variable region of SEQ ID NO:54, a binding molecule comprising a heavy chain variable region of SEQ ID NO:58, and a binding molecule comprising a heavy chain variable region of SEQ ID NO:62.

In a further embodiment, the binding molecules hereof comprise a light chain variable region comprising an amino acid sequence selected from the group consisting of SEQ ID NO:4, SEQ ID NO:8, SEQ ID NO:12, SEQ ID NO:16, SEQ ID NO:20, SEQ ID NO:24, SEQ ID NO:28, SEQ ID NO:32, SEQ ID NO:36, SEQ ID NO:40, SEQ ID NO:44, SEQ ID NO:48, SEQ ID NO:52, SEQ ID NO:56, SEQ ID NO:60, and SEQ ID NO:64.

In yet another embodiment, the binding molecule is selected from the group consisting of:
a) a binding molecule comprising a heavy chain variable region of SEQ ID NO:2 and a light chain variable region of SEQ ID NO:4;
b) a binding molecule comprising a heavy chain variable region of SEQ ID NO:6 and a light chain variable region of SEQ ID NO:8;
c) a binding molecule comprising a heavy chain variable region of SEQ ID NO:10 and a light chain variable region of SEQ ID NO:12;
d) a binding molecule comprising a heavy chain variable region of SEQ ID NO:14 and a light chain variable region of SEQ ID NO:16;
e) a binding molecule comprising a heavy chain variable region of SEQ ID NO:18 and a light chain variable region of SEQ ID NO:20;
f) a binding molecule comprising a heavy chain variable region of SEQ ID NO:22 and a light chain variable region of SEQ ID NO:24;
g) a binding molecule comprising a heavy chain variable region of SEQ ID NO:26 and a light chain variable region of SEQ ID NO:28;
h) a binding molecule comprising a heavy chain variable region of SEQ ID NO:30 and a light chain variable region of SEQ ID NO:32;
i) a binding molecule comprising a heavy chain variable region of SEQ ID NO:34 and a light chain variable region of SEQ ID NO:36;
j) a binding molecule comprising a heavy chain variable region of SEQ ID NO:38 and a light chain variable region of SEQ ID NO:40;
k) a binding molecule comprising a heavy chain variable region of SEQ ID NO:42 and a light chain variable region of SEQ ID NO:44;
l) a binding molecule comprising a heavy chain variable region of SEQ ID NO:46 and a light chain variable region of SEQ ID NO:48;
m) a binding molecule comprising a heavy chain variable region of SEQ ID NO:50 and a light chain variable region of SEQ ID NO:52;
n) a binding molecule comprising a heavy chain variable region of SEQ ID NO:54 and a light chain variable region of SEQ ID NO:56;
o) a binding molecule comprising a heavy chain variable region of SEQ ID NO:58 and a light chain variable region of SEQ ID NO:60; and
p) a binding molecule comprising a heavy chain variable region of SEQ ID NO:62 and a light chain variable region of SEQ ID NO:64.

In certain embodiments, the human binding molecules hereof are selected from the group consisting of: a binding molecule comprising a heavy chain variable region of SEQ ID NO:10 and a light chain variable region of SEQ ID NO:12; a binding molecule comprising a heavy chain variable region of SEQ ID NO:54 and a light chain variable region of SEQ ID NO:56; a binding molecule comprising a heavy chain variable region of SEQ ID NO:58 and a light chain variable region of SEQ ID NO:60; and a binding molecule comprising a heavy chain variable region of SEQ ID NO:62 and a light chain variable region of SEQ ID NO:64.

In certain embodiments, the binding molecules are for a use as a medicament, and preferably for use in the diagnostic, therapeutic, and/or prophylactic treatment of influenza infection caused by influenza A and/or B viruses. Preferably, the influenza virus that causes the influenza infection and that can be treated using the binding molecules hereof is an influenza A virus of phylogenetic group 1 and/or 2, and/or an influenza B virus. The disclosure also relates to a pharmaceutical composition comprising at least one binding molecule hereof and a pharmaceutically acceptable excipient.

In yet another embodiment, this disclosure relates to the use of a binding molecule hereof in the preparation of a medicament for the diagnosis, prophylaxis, and/or treatment of an influenza virus infection. Such infections can occur in small populations, but can also spread around the world in seasonal epidemics or, worse, in global pandemics where millions of individuals are at risk. Provided are binding molecules that can neutralize the infection of influenza strains that cause such seasonal epidemics, as well as potential pandemics. Importantly, protection and treatment can be envisioned now with the binding molecules hereof in relation to various influenza subtypes as it has been disclosed that the binding molecules hereof are capable of cross-neutralizing various influenza subtypes of both phylogenetic group 1, encompassing H1, H2, H5, H6, H8, H9 and H11 subtypes and phylogenetic group 2, encompassing subtypes H3, H4, H7 and H10 subtypes, as well as influenza B subtypes.

Another aspect hereof includes functional variants of the binding molecules as defined herein. Molecules are considered to be functional variants of a binding molecule hereof, if the variants are capable of competing for specifically binding to an influenza virus or a fragment thereof with the "parental" or "reference" binding molecules. In other words, molecules are considered to be functional variants of a binding molecule hereof when the functional variants are still capable of binding to the same or overlapping epitope of the influenza virus or a fragment thereof. For the sake of this application, "parental" and "reference" will be used as synonyms meaning that the information of the reference or parental molecule, or the physical molecule itself, may form the basis for the variation. Functional variants include, but are not limited to, derivatives that are substantially similar in primary structural sequence, including those that have modifications in the Fc receptor or other regions involved with effector functions, and/or that contain, e.g., in vitro or in vivo modifications, chemical and/or biochemical, that are not found in the parental binding molecule. Such modifications include inter alia acetylation, acylation, covalent attachment of a nucleotide or nucleotide derivative, covalent attachment of a lipid or lipid derivative, cross-linking, disulfide bond formation, glycosylation, hydroxylation, methylation, oxidation, pegylation, proteolytic processing, phosphorylation, and the like.

Alternatively, functional variants can be binding molecules, as defined in the disclosure, comprising an amino acid sequence containing substitutions, insertions, deletions or combinations thereof of one or more amino acids compared to the amino acid sequences of the parental binding molecules. Furthermore, functional variants can comprise truncations of the amino acid sequence at either or both the amino or carboxyl termini. Functional variants according to the disclosure may have the same or different, either higher or lower, binding affinities compared to the parental binding molecule but are still capable of binding to the influenza virus or a fragment thereof. For instance, functional variants according to the disclosure may have increased or decreased binding affinities for an influenza virus or a fragment thereof compared to the parental binding molecules. Preferably, the amino acid sequences of the variable regions, including, but not limited to, framework regions, hypervariable regions, in particular, the CDR3 regions, are modified. Generally, the light chain and the heavy chain variable regions comprise three hypervariable regions, comprising three CDRs, and more conserved regions, the so-called framework regions (FRs). The hypervariable regions comprise amino acid residues from CDRs and amino acid residues from hypervariable loops. Functional variants intended to fall within the scope of the disclosure have at least about 50% to about 99%, preferably at least about 60% to about 99%, more preferably at least about 70% to about 99%, even more preferably at least about 80% to about 99%, most preferably at least about 90% to about 99%, in particular, at least about 95% to about 99%, and in particular, at least about 97% to about 99% amino acid sequence identity and/or homology with the parental binding molecules as defined herein. Computer algorithms such as inter alia Gap or Bestfit known to a person skilled in the art can be used to optimally align amino acid sequences to be compared and to define similar or identical amino acid residues. Functional variants can be obtained by altering the parental binding molecules or parts thereof by general molecular biology methods known in the art including, but not limited to, error-prone PCR, oligo-nucleotide-directed mutagenesis, site-directed mutagenesis and heavy and/or light chain shuffling. In certain embodiments, the functional variants of the disclosure have neutralizing activity against influenza A viruses of group 1 and group 2, and/or influenza B viruses. The neutralizing activity may either be identical, or be higher or lower compared to the parental binding molecules. Henceforth, when the term (human) binding molecule is used, this also encompasses functional variants of the (human) binding molecule. Assays for verifying if a variant binding molecule has neutralizing activity are well known in the art (see *WHO Manual on Animal Influenza Diagnosis and Surveillance*, Geneva: World Health Organisation, 2005 version 2002.5).

In yet a further aspect, the disclosure includes immunoconjugates, i.e., molecules comprising at least one binding molecule as defined herein and further comprising at least one tag, such as inter alia a detectable moiety/agent. Also contemplated in the disclosure are mixtures of immunoconjugates according to the disclosure or mixtures of at least one immunoconjugate according to the disclosure and another molecule, such as a therapeutic agent or another binding molecule or immunoconjugate. In a further embodiment, the immunoconjugates of the disclosure may comprise more than one tag. These tags can be the same or distinct from each other and can be joined/conjugated non-covalently to the binding molecules. The tag(s) can also be joined/conjugated directly to the human binding molecules through covalent bonding. Alternatively, the tag(s) can be joined/conjugated to the binding molecules by means of one or more linking compounds. Techniques for conjugating tags to binding molecules are well known to the skilled artisan.

The tags of the immunoconjugates of the disclosure may be therapeutic agents, but they can also be detectable moieties/agents. Tags suitable in therapy and/or prevention may be toxins or functional parts thereof, antibiotics, enzymes, or other binding molecules that enhance phagocytosis or immune stimulation. Immunoconjugates comprising a detectable agent can be used diagnostically to, for example, assess if a subject has been infected with an influenza virus or to monitor the development or progression of an influenza virus infection as part of a clinical testing procedure to, e.g., determine the efficacy of a given treatment regimen. However, they may also be used for other detection and/or analytical and/or diagnostic purposes. Detectable moieties/agents include, but are not limited to, enzymes, prosthetic groups, fluorescent materials, luminescent materials, bioluminescent materials, radioactive materials, positron-emitting metals, and non-radioactive paramagnetic metal ions. The tags used to label the binding molecules for detection and/or analytical and/or diagnostic purposes depend on the specific detection/analysis/diagnosis techniques and/or methods used such as inter alia immunohistochemical staining of (tissue) samples, flow cytometric detection, scanning laser cytometric detection, fluorescent immunoassays, enzyme-linked immunosorbent assays (ELISAs), radioimmunoassays (RIAs), bioassays (e.g., phagocytosis assays), Western blotting applications, etc. Suitable labels for the detection/analysis/diagnosis techniques and/or methods known in the art are well within the reach of the skilled artisan.

Furthermore, the human binding molecules or immunoconjugates of this disclosure can also be attached to solid supports, which are particularly useful for in vitro immunoassays or purification of influenza viruses or fragments thereof. Such solid supports might be porous or nonporous, planar or non-planar. The binding molecules hereof can be fused to marker sequences, such as a peptide to facilitate purification. Examples include, but are not limited to, the hexa-histidine tag, the hemagglutinin (HA) tag, the myc tag or the flag tag. Alternatively, an antibody can be conjugated to a second antibody to form an antibody heteroconjugate. In another aspect, the binding molecules hereof may be conjugated/attached to one or more antigens. Preferably, these antigens are antigens that are recognized by the immune system of a subject to which the binding molecule-antigen conjugate is administered. The antigens may be identical, but may also differ from each other. Conjugation methods for attaching the antigens and binding molecules are well known in the art and include, but are not limited to, the use of cross-linking agents. The binding molecules hereof will bind to influenza virus HA and the antigens attached to the binding molecules will initiate a powerful T-cell attack on the conjugate, which will eventually lead to the destruction of the influenza virus.

Next to chemically producing immunoconjugates by conjugating, directly or indirectly, via, for instance, a linker, the immunoconjugates can be produced as fusion proteins comprising the binding molecules hereof and a suitable tag. Fusion proteins can be produced by methods known in the art such as, e.g., recombinantly by constructing nucleic acid molecules comprising nucleotide sequences encoding the binding molecules in frame with nucleotide sequences encoding the suitable tag(s) and then expressing the nucleic acid molecules.

It is another aspect to provide a nucleic acid molecule encoding at least a binding molecule, functional variant or immunoconjugate according to this disclosure. Such nucleic acid molecules can be used as intermediates for cloning purposes, e.g., in the process of affinity maturation as described above. In certain embodiments, the nucleic acid molecules are isolated or purified.

The skilled person will appreciate that functional variants of these nucleic acid molecules are also intended to be a part of the disclosure. Functional variants are nucleic acid sequences that can be directly translated, using the standard genetic code, to provide an amino acid sequence identical to that translated from the parental nucleic acid molecules.

Preferably, the nucleic acid molecules encode binding molecules comprising the CDR regions as described above. In a further embodiment the nucleic acid molecules encode binding molecules comprising two, three, four, five or even all six CDR regions of the binding molecules hereof.

In another embodiment, the nucleic acid molecules encode binding molecules comprising a heavy chain comprising the variable heavy chain sequences as described above. In another embodiment the nucleic acid molecules encode binding molecules comprising a light chain comprising the variable light chain sequences as described above. The nucleotide sequences and the amino acid sequences of the heavy and light chain variable regions of the binding molecules hereof are given below.

It is another aspect to provide vectors, i.e., nucleic acid constructs, comprising one or more nucleic acid molecules hereof. Vectors can be derived from plasmids, such as inter alia F, R1, RP1, Col, pBR322, TOL, Ti, etc.; cosmids; phages, such as lambda, lambdoid, M13, Mu, P1, P22, Qβ, T-even, T-odd, T2, T4, T7, etc.; and plant viruses. Vectors can be used for cloning and/or for expression of the binding molecules hereof and might even be used for gene therapy purposes. Vectors comprising one or more nucleic acid molecules, according to the disclosure, operably linked to one or more expression-regulating nucleic acid molecules are also covered by the disclosure. The choice of the vector is dependent on the recombinant procedures followed and the host used. Introduction of vectors in host cells can be effected by inter alia calcium phosphate transfection, virus infection, DEAE-dextran-mediated transfection, lipofectamin transfection or electroporation. Vectors may be autonomously replicating or may replicate together with the chromosome into which they have been integrated. Preferably, the vectors contain one or more selection markers. The choice of the markers may depend on the host cells of choice, although this is not critical to the disclosure, as is well known to persons skilled in the art. They include, but are not limited to, kanamycin, neomycin, puromycin, hygromycin, zeocin, thymidine kinase gene from Herpes simplex virus (HSV-TK), and dihydrofolate reductase gene from mouse (dhfr). Vectors comprising one or more nucleic acid molecules encoding the human binding molecules as described above, operably linked to one or more nucleic acid molecules encoding proteins or peptides that can be used to isolate the human binding molecules, are also covered by the disclosure. These proteins or peptides include, but are not limited to, glutathione-S-transferase, maltose binding protein, metal-binding polyhistidine, green fluorescent protein, luciferase and beta-galactosidase.

Hosts containing one or more copies of the vectors mentioned above are an additional subject hereof. Preferably, the hosts are host cells. Host cells include, but are not limited to, cells of mammalian, plant, insect, fungal or bacterial origin. Bacterial cells include, but are not limited to, cells from gram-positive bacteria or gram-negative bacteria, such as several species of the genera *Escherichia*, such as *E. coli*, and *Pseudomonas*. In the group of fungal cells, yeast cells are preferably used. Expression in yeast can be achieved by using yeast strains such as inter alia *Pichia pastoris, Saccharomyces cerevisiae* and *Hansenula polymorpha*. Furthermore, insect cells, such as cells from *Drosophila* and Sf9, can be used as host cells. Besides that, the host cells can be plant cells such as inter alia cells from crop plants such as forestry plants, or cells from plants providing food and raw materials such as cereal plants, or medicinal plants, or cells from ornamentals, or cells from flower bulb crops. Transformed (transgenic) plants or plant cells are produced by known methods, for example, *Agrobacterium*-mediated gene transfer, transformation of leaf discs, protoplast transformation by polyethylene glycol-induced DNA transfer, electroporation, sonication, microinjection or bolistic gene transfer. Additionally, a suitable expression system can be a baculovirus system. Expression systems using mammalian cells, such as Chinese Hamster Ovary (CHO) cells, COS cells, BHK cells, NSO cells or Bowes melanoma cells are preferred in the disclosure. Mammalian cells provide expressed proteins with post-translational modifications that are most similar to natural molecules of mammalian origin. Since the disclosure deals with molecules that may have to be administered to humans, a completely human expression system would be particularly preferred. Therefore, even more preferably, the host cells are human cells. Examples of human cells are inter alia HeLa, 911, AT1080, A549, 293 and HEK293T cells. In preferred embodiments, the human producer cells comprise at least a functional part of a nucleic acid sequence encoding an adenovirus E1 region in expressible format. In even more preferred embodiments, the host cells are derived from a human retina and immortalized with nucleic acids comprising adenoviral E1 sequences, such as 911 cells or the cell line deposited at the European Collection of Cell Cultures (ECACC), CAMR, Salisbury, Wiltshire SP4 OJG, Great Britain on 29 Feb. 1996 under number 96022940 and marketed under the trademark PER.C6® (PER.C6® is a registered trademark of Crucell Holland B.V.). For the purposes of this application "PER.C6® cells" refers to cells deposited under number 96022940 or ancestors, passages up-stream or downstream, as well as descendants from ancestors of deposited cells, as well as derivatives of any of the foregoing. Production of recombinant proteins in host cells can be performed according to methods well known in the art. The use of the cells marketed under the trademark PER.C6® as a production platform for proteins of interest has been described in WO 00/63403, the disclosure of which is incorporated herein in its entirety by this reference.

In yet another embodiment, binding molecules can also be produced in transgenic, non-human, mammals such as inter alia rabbits, goats or cows, and secreted into, for instance, the milk thereof.

In yet another alternative embodiment, the binding molecules may be generated by transgenic non-human mammals, such as, for instance, transgenic mice or rabbits that express human immunoglobulin genes. Preferably, the transgenic non-human mammals have a genome comprising a human heavy chain transgene and a human light chain transgene encoding all or a portion of the human binding molecules as described above. The transgenic non-human mammals can be immunized with a purified or enriched preparation of influenza virus or a fragment thereof. Protocols for immunizing non-human mammals are well established in the art. See *Using Antibodies: A Laboratory Manual*, edited by E. Harlow, D. Lane (1998), Cold Spring Harbor Laboratory, Cold Spring Harbor, New York; and *Current Protocols in Immunology*, edited by J. E. Coligan, A. M. Kruisbeek, D. H. Margulies, E. M. Shevach, and W. Strober (2001), John Wiley & Sons Inc., New York, the disclosures of which are incorporated herein in their entirety by this reference. Immunization protocols often include multiple immunizations, either with or without adjuvants, such as Freund's complete adjuvant and Freund's incomplete adjuvant, but may also include naked DNA immunizations. In another embodiment, the human binding molecules are produced by B cells, plasma and/or memory cells derived from the transgenic animals. In yet another embodiment, the human binding molecules are produced by hybridomas, which are prepared by fusion of B cells obtained from the above-described transgenic non-human mammals to immortalized cells. B cells, plasma cells and hybridomas, as obtainable from the above-described transgenic non-human mammals, and human binding molecules, as obtainable from the above-described transgenic non-human mammals, B cells, plasma and/or memory cells and hybridomas are also a part of the disclosure.

In yet a further aspect, provided are compositions comprising at least a binding molecule, preferably a human monoclonal antibody according to the disclosure, at least a functional variant thereof, at least an immunoconjugate according to the disclosure and/or a combination thereof. In addition to that, the compositions may comprise inter alia stabilizing molecules, such as albumin or polyethylene glycol, or salts. Preferably, the salts used are salts that retain the desired biological activity of the binding molecules and do not impart any undesired toxicological effects. If necessary, the human binding molecules hereof may be coated in or on a material to protect them from the action of acids or other natural or non-natural conditions that may inactivate the binding molecules.

In yet a further aspect, provided are compositions comprising at least a nucleic acid molecule as defined in the disclosure. The compositions may comprise aqueous solutions such as aqueous solutions containing salts (e.g., NaCl or salts as described above), detergents (e.g., SDS) and/or other suitable components.

Furthermore, the disclosure pertains to pharmaceutical compositions comprising at least a binding molecule such as a human monoclonal antibody of the disclosure (or functional fragment or variant thereof), at least an immunoconjugate according to the disclosure, at least a composition according to the disclosure, or combinations thereof. The pharmaceutical composition hereof further comprises at least one pharmaceutically acceptable excipient. Pharmaceutically acceptable excipients are well known to the skilled person. The pharmaceutical composition according to the disclosure may further comprise at least one other therapeutic agent. Suitable agents are also well known to the skilled artisan.

In a preferred embodiment, the pharmaceutical composition hereof comprises at least one additional binding molecule, i.e., the pharmaceutical composition can be a cocktail or mixture of binding molecules. The pharmaceutical composition may comprise at least two binding molecules hereof, or at least one binding molecule hereof and at least one further influenza virus binding and/or neutralizing molecule, such as another antibody directed against the HA protein or against other antigenic structures present on influenza viruses, such as M2. In another embodiment, the additional binding molecule may be formulated for simultaneous separate or sequential administration.

In certain embodiments, the pharmaceutical compositions may comprise two or more binding molecules that have neutralizing activity against influenza A viruses and/or influenza B viruses. In certain embodiments, the binding molecules exhibit synergistic neutralizing activity when used in combination. As used herein, the term "synergistic" means that the combined effect of the binding molecules when used in combination is greater than their additive effects when used individually. The synergistically acting binding molecules may bind to different structures on the same or distinct fragments of influenza virus. A way of calculating synergy is by means of the combination index. The concept of the combination index (CI) has been described by Chou and Talalay (1984). The compositions may, e.g., comprise one binding molecule having neutralizing activity and one non-neutralizing binding molecule. The non-neutralizing and neutralizing binding molecules may also act synergistically in neutralizing influenza virus.

In certain embodiments, the pharmaceutical composition may comprise at least one binding molecule hereof and at least one further influenza virus-neutralizing binding molecule. Preferably, the binding molecules in the pharmaceutical composition are capable of reacting with influenza viruses of different subtypes. The binding molecules should be of high affinity and should have a broad specificity. Preferably, both binding molecules are cross-neutralizing molecules in that they each neutralize influenza viruses of different subtypes. In addition, preferably, they neutralize as many strains of each of the different influenza virus subtypes as possible.

The pharmaceutical composition can further comprise at least one other therapeutic, prophylactic, and/or diagnostic agent. Preferably, the pharmaceutical composition comprises at least one other prophylactic and/or therapeutic agent. More preferably, therapeutic and/or prophylactic agents are agents capable of preventing and/or treating an influenza virus infection and/or a condition resulting from such an infection. Therapeutic and/or prophylactic agents include, but are not limited to, anti-viral agents. Such agents can be binding molecules, small molecules, organic or inorganic compounds, enzymes, polynucleotide sequences, anti-viral peptides, etc. Other agents that are currently used to treat patients infected with influenza viruses are M2 inhibitors (e.g., amantidine, rimantadine) and/or neuraminidase inhibitors (e.g., zanamivir, oseltamivir). These can be used in combination with the binding molecules hereof. "In combination" herein means simultaneously, as separate formulations, or as one single combined formulation, or according to a sequential administration regimen as separate formulations, in any order. Agents capable of preventing and/or treating an infection with influenza virus and/or a condition resulting from such an infection that are in the experimental phase might also be used as other therapeutic and/or prophylactic agents useful in the disclosure.

The binding molecules or pharmaceutical compositions of the disclosure can be tested in suitable animal model systems prior to use in humans. Such animal model systems include, but are not limited to, mouse, ferret and monkey.

Typically, pharmaceutical compositions must be sterile and stable under the conditions of manufacture and storage. The binding molecules, immunoconjugates, nucleic acid molecules or compositions hereof can be in powder form for reconstitution in the appropriate pharmaceutically acceptable excipient before or at the time of delivery. In the case of sterile powders for the preparation of sterile injectable solutions, the preferred methods of preparation are vacuum drying and freeze-drying (lyophilization) that yield a powder of the active ingredient plus any additional desired ingredient from a previously sterile-filtered solution thereof.

Alternatively, the binding molecules, immunoconjugates, nucleic acid molecules or compositions hereof can be in solution and the appropriate pharmaceutically acceptable excipient can be added and/or mixed before or at the time of delivery to provide a unit dosage injectable form. Preferably, the pharmaceutically acceptable excipient used herein is suitable for high drug concentration, can maintain proper fluidity and, if necessary, can delay absorption.

The choice of the optimal route of administration of the pharmaceutical compositions will be influenced by several factors including the physicochemical properties of the active molecules within the compositions, the urgency of the clinical situation and the relationship of the plasma concentrations of the active molecules to the desired therapeutic effect. For instance, if necessary, the binding molecules hereof can be prepared with carriers that will protect them against rapid release, such as a controlled release formulation, including implants, transdermal patches, and microencapsulated delivery systems. Biodegradable, biocompatible polymers can inter alia be used, such as ethylene vinyl acetate, polyanhydrides, polyglycolic acid, collagen, polyorthoesters, and polylactic acid. Furthermore, it may be necessary to coat the binding molecules with, or co-administer the binding molecules with, a material or compound that prevents the inactivation of the human binding molecules. For example, the binding molecules may be administered to a subject in an appropriate carrier, for example, liposomes or a diluent.

The routes of administration can be divided into two main categories, oral and parenteral administration. The preferred administration route is intravenous or by inhalation.

Oral dosage forms can be formulated inter alia as tablets, troches, lozenges, aqueous or oily suspensions, dispersible powders or granules, emulsions, hard capsules, soft gelatin capsules, syrups or elixirs, pills, dragees, liquids, gels, or slurries. These formulations can contain pharmaceutically acceptable excipients including, but not limited to, inert diluents, granulating and disintegrating agents, binding agents, lubricating agents, preservatives, coloring, flavoring or sweetening agents, vegetable or mineral oils, wetting agents, and thickening agents.

The pharmaceutical compositions hereof can also be formulated for parenteral administration. Formulations for parenteral administration can be inter alia in the form of aqueous or non-aqueous isotonic sterile non-toxic injection or infusion solutions or suspensions. The solutions or suspensions may comprise agents that are non-toxic to recipients at the dosages and concentrations employed such as 1,3-butanediol, Ringer's solution, Hank's solution, isotonic sodium chloride solution, oils, fatty acids, local anaesthetic agents, preservatives, buffers, viscosity or solubility increasing agents, water-soluble antioxidants, oil-soluble antioxidants and metal chelating agents.

In a further aspect, the binding molecules such as human monoclonal antibodies (functional fragments and variants thereof), immunoconjugates, compositions, or pharmaceutical compositions of the disclosure, can be used as a medicament. A method of diagnosis, treatment and/or prevention of an influenza virus infection using the binding molecules, immunoconjugates, compositions, or pharmaceutical compositions of the disclosure is another part of the disclosure. The above-mentioned molecules can inter alia be used in the diagnosis, prophylaxis, treatment, or combination thereof, of an influenza virus infection caused by influenza viruses comprising HA of the H1, H2, H3, H4, H5, H6, H7, H8, H9, H10 and/or H11 subtype. In certain embodiments, the above-mentioned molecules can also be used in the diagnosis, prophylaxis, treatment or combination thereof of an influenza virus infection caused by an influenza B virus. They are suitable for treatment of yet untreated patients suffering from an influenza virus infection and patients who have been or are treated for an influenza virus infection.

The above-mentioned molecules or compositions may be employed in conjunction with other molecules useful in diagnosis, prophylaxis and/or treatment. They can be used in vitro, ex vivo or in vivo. For instance, the binding molecules such as human monoclonal antibodies (or functional variants thereof), immunoconjugates, compositions or pharmaceutical compositions of the disclosure can be co-administered with a vaccine against influenza virus (if available). Alternatively, the vaccine may also be administered before or after administration of the molecules hereof. Instead of a vaccine, anti-viral agents can also be employed in conjunction with the binding molecules hereof. Suitable anti-viral agents are mentioned above.

The molecules are typically formulated in the compositions and pharmaceutical compositions hereof in a therapeutically or diagnostically effective amount. Alternatively, they may be formulated and administered separately. For instance, the other molecules such as the anti-viral agents may be applied systemically, while the binding molecules hereof may be applied intravenously.

Treatment may be targeted at patient groups that are susceptible to influenza infection. Such patient groups include, but are not limited to, e.g., the elderly (e.g., ≥50 years old, ≥60 years old, and preferably ≥65 years old), the young (e.g., ≤5 years old, ≤1 year old), hospitalized patients and already infected patients who have been treated with an antiviral compound but have shown an inadequate antiviral response.

Dosage regimens can be adjusted to provide the optimum desired response (e.g., a therapeutic response). A suitable dosage range may, for instance, be 0.01-100 mg/kg body weight, preferably 0.1-50 mg/kg body weight, preferably 0.01-15 mg/kg body weight. Furthermore, for example, a single bolus may be administered, several divided doses may be administered over time or the dose may be proportionally reduced or increased as indicated by the exigencies of the therapeutic situation. The molecules and compositions according to the disclosure are preferably sterile. Methods to render these molecules and compositions sterile are well known in the art. The other molecules useful in diagnosis, prophylaxis and/or treatment can be administered in a similar dosage regimen as proposed for the binding molecules hereof. If the other molecules are administered separately, they may be administered to a patient prior to (e.g., 2 minutes, 5 minutes, 10 minutes, 15 minutes, 30 minutes, 45 minutes, 60 minutes, 2 hours, 4 hours, 6 hours, 8 hours, 10 hours, 12 hours, 14 hours, 16 hours, 18 hours, 20 hours, 22 hours, 24 hours, 2 days, 3 days, 4 days, 5 days, 7 days, 2 weeks, 4 weeks or 6 weeks before), concomitantly with, or subsequent to (e.g., 2 minutes, 5 minutes, 10 minutes, 15 minutes, 30 minutes, 45 minutes, 60 minutes, 2 hours, 4 hours, 6 hours, 8 hours, 10 hours, 12 hours, 14 hours, 16 hours, 18 hours, 20 hours, 22 hours, 24 hours, 2 days, 3 days, 4 days, 5 days, 7 days, 2 weeks, 4 weeks or 6 weeks after) the administration of one or more of the human binding molecules or pharmaceutical compositions of the disclosure. The exact dosing regimen is usually sorted out during clinical trials in human patients.

Human binding molecules and pharmaceutical compositions comprising the human binding molecules are particularly useful, and often preferred, when they are to be administered to human beings as in vivo therapeutic agents, since recipient immune response to the administered antibody will often be substantially less than that occasioned by administration of a monoclonal murine, chimeric or humanized binding molecule.

In another aspect, the disclosure concerns the use of the binding molecules such as neutralizing human monoclonal antibodies (functional fragments and variants thereof), immunoconjugates, nucleic acid molecules, compositions or pharmaceutical compositions according to the disclosure in the preparation of a medicament for the diagnosis, prophylaxis, treatment, or combination thereof, of an influenza virus infection, in particular, an influenza virus infection caused by influenza viruses comprising HA of the H1, H2, H3, H4, H5, H6, H7, H8, H9, H10, and/or H11 subtype and/or influenza B viruses.

Next to that, kits comprising at least a binding molecule such as a neutralizing human monoclonal antibody (functional fragments and variants thereof), at least an immunoconjugate, at least a nucleic acid molecule, at least a composition, at least a pharmaceutical composition, at least a vector, at least a host according to the disclosure, or a combination thereof, are also a part of the disclosure. Optionally, the above-described components of the kits of the disclosure are packed in suitable containers and labeled for diagnosis, prophylaxis and/or treatment of the indicated conditions. The above-mentioned components may be stored in unit or multi-dose containers as an aqueous, preferably sterile, solution or as a lyophilized, preferably sterile, formulation for reconstitution. The containers may be formed from a variety of materials such as glass or plastic and may have a sterile access port (for example, the container may be an intravenous solution bag or a vial having a stopper pierceable by a hypodermic injection needle). The kit may further comprise more containers comprising a pharmaceutically acceptable buffer. It may further include other materials desirable from a commercial and user standpoint, including other buffers, diluents, filters, needles, syringes, culture medium for one or more of the suitable hosts and, possibly, even at least one other therapeutic, prophylactic or diagnostic agent. Associated with the kits can be instructions customarily included in commercial packages of therapeutic, prophylactic or diagnostic products that contain information about, for example, the indications, usage, dosage, manufacture, administration, contra-indications and/or warnings concerning the use of such therapeutic, prophylactic or diagnostic products.

The binding molecules hereof can also be advantageously used as a diagnostic agent in an in vitro method for the detection of influenza virus. The disclosure thus further pertains to a method of detecting influenza virus phylogenetic group 1 or group 2, or influenza B subtype influenza virus in a sample, wherein the method comprises the steps of (a) contacting a sample with a diagnostically effective amount of a binding molecule (functional fragments and variants thereof) or an immunoconjugate according to the disclosure, and (b) determining whether the binding molecule or immunoconjugate specifically binds to a molecule of the sample. The sample may be a biological sample including, but not limited to, blood, serum, stool, sputum, nasopharyngeal aspirates, bronchial lavages, urine, tissue or other biological material from (potentially) infected subjects, or a non-biological sample such as water, drink, etc. The (potentially) infected subjects may be human subjects, but also animals that are suspected as carriers of influenza virus might be tested for the presence of the virus using the human binding molecules or immunoconjugates of the disclosure. The sample may first be manipulated to make it more suitable for the method of detection. Manipulation means inter alia treating the sample suspected to contain and/or containing the virus in such a way that the virus will disintegrate into antigenic components such as proteins, (poly)peptides or other antigenic fragments. Preferably, the human binding molecules or immunoconjugates of the disclosure are contacted with the sample under conditions that allow the formation of an immunological complex between the human binding molecules and the virus or antigenic components thereof that may be present in the sample. The formation of an immunological complex, if any, indicating the presence of the virus in the sample, is then detected and measured by suitable means. Such methods include, inter alia, homogeneous and heterogeneous binding immunoassays, such as radio-immunoassays (RIA), ELISA, immunofluorescence, immunohistochemistry, FACS, BIACORE and Western blot analyses.

Preferred assay techniques, especially for large-scale clinical screening of patient sera and blood and blood-derived products, are ELISA and Western blot techniques. ELISA tests are particularly preferred. For use as reagents in these assays, the binding molecules or immunoconjugates of the disclosure are conveniently bonded to the inside surface of microtiter wells. The binding molecules or immunoconjugates of the disclosure may be directly bonded to the microtiter well. However, maximum binding of the binding molecules or immunoconjugates of the disclosure to the wells might be accomplished by pre-treating the wells with polylysine prior to the addition of the binding molecules or immunoconjugates of the disclosure. Furthermore, the binding molecules or immunoconjugates of the disclosure may be covalently attached by known means to the wells. Generally, the binding molecules or immunoconjugates are used in a concentration between 0.01 to 100 µg/ml for coating, although higher as well as lower amounts may also be used. Samples are then added to the wells coated with the binding molecules or immunoconjugates of the disclosure.

Furthermore, binding molecules hereof can be used to identify specific binding structures of influenza virus. The binding structures can be epitopes on proteins and/or polypeptides. They can be linear, but also structural and/or conformational. In one embodiment, the binding structures can be analyzed by means of PEPSCAN analysis (see inter alia WO 84/03564, WO 93/09872, Slootstra et al., 1996). Alternatively, a random peptide library comprising peptides from a protein of influenza virus can be screened for peptides capable of binding to the binding molecules hereof.

The disclosure is further illustrated in the following examples and figures. The examples are not intended to limit the scope of the disclosure in any way.

EXAMPLES

Example 1

Construction of scFv Phage Display Libraries Using RNA Extracted from Peripheral Blood Mononuclear Cells Peripheral blood was collected from normal healthy donors by venapuncture in EDTA anti-coagulation sample tubes. scFv phage display libraries were obtained as described in WO 2008/028946, which is incorporated by reference herein. RNA was isolated from peripheral blood mononuclear cells and cDNA prepared. A two round PCR amplification approach was applied using the primer sets shown in Tables 1 and 2 to isolate the immunoglobulin VH and VL regions from the respective donor repertoire.

First round amplification on the respective cDNA using the primer sets mentioned in Table 1 yielded seven, six, and nine products of about 650 base pairs for, respectively, VH, Vkappa and Vlambda regions. For IgM VH region amplification, the OCM constant primer was used in combination with OH1 to OH7. The thermal cycling program for first round amplifications was: 2 minutes 96° C. (denaturation step), 30 cycles of 30 seconds 96° C., 30 seconds 60° C., 60 seconds 72° C., 10 minutes 72° C. final elongation and 6° C. refrigeration. The products were loaded on and isolated from a 1% agarose gel using gel-extraction columns (Macherey-Nagel) and eluted in 50 μl 5 mM Tris-HCl pH 8.0. Ten percent of first round products (3 to 5 μl) was subjected to second round amplification using the primers mentioned in Table 2. These primers were extended with restriction sites enabling the directional cloning of the respective VL and VH regions into phage display vector PDV-006. The PCR program for second round amplifications was as follows: 2 minutes 96° C. (denaturation step), 30 cycles of 30 seconds 96° C., 30 seconds 60° C., 60 seconds 72° C., 10 minutes 72° C. final elongation and 6° C. refrigeration.

The second round products (~350 base pairs) were first pooled according to natural occurrence of J segments found in immunoglobulin gene products, resulting in seven, six, and nine pools for, respectively, the VH, Vkappa and Vlambda variable regions (see Tables 3 and 4). To obtain a normalized distribution of immunoglobulin sequences in the immune library, the six Vkappa and nine Vlambda light chain pools were mixed according to the percentages mentioned in Table 3. This single final VL pool (3 μg) was digested overnight with SalI and NotI restriction enzymes, loaded on and isolated from a 1% agarose gel (~350 base pairs) using Macherey-Nagel gel-extraction columns and ligated in SalI-NotI cut PDV-006 vector (~5000 base pairs) as follows: 10 μl PDV-006 vector (50 ng/μl), 7 μl VL insert (10 ng/μl), 5 μl 10× ligation buffer (NEB), 2.5 T4 DNA Ligase (400 U/μl) (NEB), 25.5 μl ultrapure water (vector to insert ratio was 1:2). Ligation was performed overnight in a water bath of 16° C. Next, the volume was doubled with water, extracted with an equal volume of phenol-chloroform-isoamylalcohol (75:24:1) (Invitrogen) followed by chloroform (Merck) extraction and precipitated with 1 μl PELLET PAINT® (Novagen), 10 μl sodium acetate (3 M pH 5.0) and 100 μl isopropanol for 2 hours at −20° C. The obtained sample was subsequently centrifuged at 20,000×g for 30 minutes at 4° C. The obtained precipitate was washed with 70% ethanol and centrifuged for 10 minutes at 20,000×g at room temperature. Ethanol was removed by vacuum aspiration and the pellet was air dried for several minutes and then dissolved in 50 μl buffer containing 10 mM Tris-HCl, pH 8.0. 2 μl ligation mixture was used for the transformation of 40 μl TG-1 electro-competent cells (Agilent) in a chilled 0.1 cm electroporation cuvette (Biorad) using a GENE PULSER® II apparatus (Biorad) set at 1.7 kV, 200 Ohm, 25 μF (time constant ~4.5 msec). Directly after pulse, the bacteria were flushed from the cuvette with 1000 μl SOC medium (Invitrogen) containing 5% (w/v) glucose (Sigma) at 37° C. and transferred to a 15 ml round bottom culture tube. Another 500 μl SOC/glucose was used to flush residual bacteria from the cuvette and was added to the culture tube. Bacteria were recovered by culturing for exactly one hour at 37° C. in a shaker incubator at 220 rpm. The transformed bacteria were plated over large 240 mm square petridishes (NUNC®) containing 150 ml 2TY agar (16 g/l bacto-tryptone, 10 g/l bacto-yeast extract, 5 g/l NaCl, 15 g/l agar, pH 7.0) supplemented with 50 μg/ml ampicillin and 5% (w/v) glucose (Sigma). A 1 to 1000 dilution was plated for counting purposes on 15 cm petridishes containing the same medium. This transformation procedure was repeated sequentially ten times and the complete each transformation was plated on a separate square petridish and grown overnight in a 37° C. culture stove. Typically, around $1\times10^7$ cfu ($1\times10^6$ per petridish) were obtained using the above protocol. The intermediate VL light chain library was harvested from the plates by mildly scraping the bacteria into 10 ml 2TY medium per plate. The cell mass was determined by OD600 measurement and two times 500 OD of bacteria was used for maxi plasmid DNA preparation using two P500 maxiprep columns (Macherey-Nagel) according to manufacturer's instructions.

Analogous to the VL variable regions, the second round VH-JH products were first mixed together to obtain the normal J segment usage distribution (see Table 4), resulting in seven VH subpools called PH1 to PH7. The pools were mixed to acquire a normalized sequence distribution using the percentages depicted in Table 4, obtaining one VH fraction that was digested with SfiI and XhoI restriction enzymes and ligated in SfiI-XhoI cut PDV-VL intermediate library obtained as described above. The ligation set-up, purification method, subsequent transformation of TG1 and harvest of bacteria was essentially as described for the VL intermediate library (see above) with the exception that twenty transformations and twenty square petridishes were used. The final library (approximately $1\times10^7$ cfu) was checked for insert frequency with a colony PCR using a primer set flanking the inserted VH-VL regions. 90% of the colonies showed a correct length insert. The colony PCR products were used for subsequent DNA sequence analysis to check sequence variation and to assess the percentage of colonies showing a complete ORF. This was 76%. Finally, the library was rescued and amplified by using CT helper phages (see WO 02/103012) and was used for phage antibody selection by panning methods as described below.

Example 2

Selection of Phages Carrying Single Chain Fv Fragments Against Influenza A and Influenza B Heamagglutinin Antibody fragments were selected using antibody phage display libraries constructed essentially as described above and general phage display technology and MABSTRACT® technology essentially as described in U.S. Pat. No. 6,265,150 and in WO 98/15833 (both of which are incorporated by reference herein). Furthermore, the methods and helper phages as described in WO 02/103012 (which is incorporated by reference herein) were used in the disclosure.

Selection was performed against recombinant hemagglutinin (HA) of influenza A subtype H1 (A/New Caledonia/20/99), H3 (A/Wisconsin/67/2005), H4 (A/Duck/Hong Kong/24/1976), H5 (A/Chicken/Vietnam/28/2003), H7 (A/Netherlands/219/2003) and H9 (A/HongKong/1073/99). HA antigens were diluted in PBS (5.0 µg/ml), added to MAXISORP™ NUNC®-Immuno Tubes (NUNC®) and incubated overnight at 4° C. on a rotating wheel. The immunotubes were emptied and washed three times in block buffer (2% non-fat dry milk (ELK) in PBS). Subsequently, the immunotubes were filled completely with block buffer and incubated for 1 to 2 hours at room temperature. Aliquots of phage display library (500-1000 µl, $0.5\times10^{13}$-$1\times10^{13}$ cfu, amplified using CT helper phage (see WO 02/103012)) were blocked in blocking buffer supplemented with 10% non-heat inactivated fetal bovine serum and 2% mouse serum for 1 to 2 hours at room temperature. The blocked phage library was added to the immunotubes, incubated for 2 hours at room temperature, and washed with wash buffer (0.05% (v/v) TWEEN®-20 in PBS) to remove unbound phages. Bound phages were eluted from the respective antigen by incubation with 1 ml of 100 mM triethylamine (TEA) for 10 minutes at room temperature. Subsequently, the eluted phages were mixed with 0.5 ml of 1 M Tris-HCl pH 7.5 to neutralize the pH. This mixture was used to infect 5 ml of an XL1-Blue *E. coli* culture that had been grown at 37° C. to an OD 600 nm of approximately 0.3. The phages were allowed to infect the XL1-Blue bacteria for 30 minutes at 37° C. Then, the mixture was centrifuged for 10 minutes at 3000×g at room temperature and the bacterial pellet was resuspended in 0.5 ml 2-trypton yeast extract (2TY) medium. The obtained bacterial suspension was divided over two 2TY agar plates supplemented with tetracycline, ampicillin and glucose. After incubation overnight of the plates at 37° C., the colonies were scraped from the plates and used to prepare an enriched phage library, essentially as described by De Kruif et al. (1995) and WO 02/103012. Briefly, scraped bacteria were used to inoculate 2TY medium containing ampicillin, tetracycline and glucose and grown at a temperature of 37° C. to an OD 600 nm of ~0.3. CT helper phages were added and allowed to infect the bacteria after which the medium was changed to 2TY containing ampicillin, tetracycline and kanamycin. Incubation was continued overnight at 30° C. The next day, the bacteria were removed from the 2TY medium by centrifugation after which the phages in the medium were precipitated using polyethylene glycol (PEG) 6000/NaCl. Finally, the phages were dissolved in 2 ml of PBS with 1% bovine serum albumin (BSA), filter-sterilized and used for the next round of selection. The second round of selection is performed either on the same HA subtype and/or on HA of a different subtype.

Two consecutive rounds of selections were performed before isolation of individual single-chain phage antibodies. After the second round of selection, individual *E. coli* colonies were used to prepare monoclonal phage antibodies. Essentially, individual colonies were grown to log-phase in 96-well plate format and infected with VCS-M13 helper phages after which phage antibody production was allowed to proceed overnight. Phagemids were sequence analyzed and all unique phagemids were used for further analysis. The supernatants containing phage antibodies were used directly in ELISA for binding to HA antigens. Alternatively, phage antibodies were PEG/NaCl-precipitated and filter-sterilized for both ELISA and flow cytometry analysis.

Example 3

Validation of the HA-Specific Single-Chain Phage Antibodies

Selected supernatants containing single-chain phage antibodies that were obtained in the screenings described above were validated in ELISA for specificity, i.e., binding to different HA antigens. For this purpose, baculovirus expressed recombinant H1 (A/New Caledonia/20/99), H3 (A/Wisconsin/67/2005), H5 (A/Vietnam/1203/04) H7 (A/Netherlands/219/2003), and B (B/Ohio/01/2005) HAs (Protein Sciences, CT, USA) were coated to MAXISORP™ ELISA plates. After coating, the plates were washed three times with PBS containing 0.1% v/v TWEEN®-20 and blocked in PBS containing 3% BSA or 2% ELK for 1 hour at room temperature. The selected single-chain phage antibodies were incubated for 1 hour in an equal volume of PBS containing 4% ELK to obtain blocked phage antibodies. The plates were emptied, washed three times with PBS/0.1% TWEEN®-20 and the blocked single-chain phage antibodies were added to the wells. Incubation was allowed to proceed for one hour, the plates were washed with PBS/0.1% TWEEN®-20 and bound phage antibodies were detected (using OD 492 nm measurement) using an anti-M13 antibody conjugated to peroxidase. As a control, the procedure was performed simultaneously without single-chain phage antibody and with an unrelated negative control single-chain phage antibody. From the selections on the different HA antigens with the phage libraries, 13 unique single-chain phage antibodies specifically binding recombinant influenza A H1, H3, H5, H7 and influenza B HA were obtained (SC09-003, SC09-004, SC09-005, SC09-006, SC09-007, SC09-008, SC09-009, SC09-010, SC09-011, SC09-030, SC09-112, SC09-113 and SC09-114). See Table 5.

Alternatively, PEG/NaCl-precipitated and filter-sterilized phage antibodies were used to validate binding and specificity by FACS analysis. For this purpose, full-length recombinant influenza A subtypes H1 (A/New Caledonia/20/1999), H3 (A/Wisconsin/67/2005) and H7 (A/Netherlands/219/2003) HAs were expressed on the surface of PER.C6® cells. The cells were incubated with single-chain phage antibodies for 1 hour followed by three wash steps with PBS+0.1% BSA. Bound phages were detected using FITC conjugated M13-antibody. From the selections on the different HA antigens with the phage libraries, 14 single-chain phage antibodies specifically binding influenza A subtypes H1, H3 and H7 HA were found (SC09-003, SC09-004, SC09-005, SC09-006, SC09-007, SC09-008, SC09-009, SC09-010, SC09-011, SC09-012, SC09-030, SC09-112, SC09-113 and SC09-114). See Table 6.

All 16 phage antibodies, SC09-003, SC09-004, SC09-005, SC09-006, SC09-007, SC09-008, SC09-009, SC09-010, SC09-011, SC09-012, SC09-029, SC09-030, SC09-031, SC09-112, SC09-113 and SC09-114, were used for construction of fully human immunoglobulins.

Example 4

Construction of Fully Human Immunoglobulin Molecules (Human Monoclonal Antibodies) from the Selected Single Chain Fvs From the selected specific single-chain phage antibody (scFv) clones, plasmid DNA was obtained and nucleotide and amino acid sequences were determined according to standard techniques. Heavy and light chain variable regions of the scFvs were cloned directly by restriction digest for expression in the IgG expression vectors pIg-C911-HCgammal (see SEQ ID NO:175), pIG-C909-Ckappa (see SEQ ID NO:176), or pIg-C910-Clambda (see SEQ ID NO:177). The VH and VL gene identity (see I. M. Tomlinson et al. (1997), *V BASE Sequence Directory*, Cambridge United Kingdom: MRC Centre for Protein Engineering) of the scFvs were determined (see Table 7).

Nucleotide sequences for all constructs were verified according to standard techniques known to the skilled artisan. The resulting expression constructs encoding the human IgG1 heavy and light chains were transiently expressed in combination in 293T cells and supernatants containing human IgG1 antibodies were obtained and produced using standard purification procedures.

The amino acid sequence of the CDRs of the heavy and light chains of the selected immunoglobulin molecules is given in Table 7.

The number of amino-acid differences and the % identity of all heavy and light chain variable domains are given in Table 8.

Example 5

Cross-Binding Reactivity of IgGs

A panel of five of the IgG antibodies described above, CR9005, CR9030, CR9112, CR9113 and CR9114, was validated in ELISA for binding specificity, i.e., binding to different HA antigens. For this purpose, baculovirus-expressed recombinant H1 (A/New Caledonia/20/1999), H3 (A/Wisconsin/67/2005), H5 (A/Vietnam/1203/04), H7 (A/Netherlands/219/2003) and H9 (A/HongKong/1073/99) HAs (Protein Sciences, CT, USA) were coated to MAXISORP™ ELISA plates. After coating, the plates were washed three times with PBS containing 0.1% v/v TWEEN®-20 and blocked in PBS containing 3% BSA or 2% ELK for 1 hour at room temperature. The plates were emptied, washed three times with PBS/0.1% TWEEN®-20 and the IgG antibodies were added to the wells. Incubation was allowed to proceed for one hour, the plates were washed with PBS/0.1% TWEEN®-20 and bound antibodies were detected (using OD 492 nm measurement) using an anti-human IgG antibody conjugated to peroxidase. As a control, an unrelated IgG CR4098 was used.

CR9005, CR9030, CR9112, CR9113 and CR9114 were shown to have heterosubtypic cross-binding activity to all the recombinant HAs tested. See Table 9.

Additionally, the selected antibodies were used to test heterosubtypic binding by FACS analysis. For this purpose, full-length recombinant influenza A subtypes H1 (A/New Caledonia/20/1999), H3 (A/Wisconsin/67/2005) and H7 (A/Netherlands/219/2003) HAs were expressed on the surface of PER.C6® cells. The cells were incubated with IgG antibodies for 1 hour followed by three wash steps with PBS+0.1% BSA. Bound antibodies were detected using PE-conjugated anti-human antibody. As a control, untransfected PER.C6® cells were used. CR9005, CR9030, CR9112, CR9113 and CR9114 show cross-binding activity to influenza A subtypes H1, H3 and H7 HA but not wild-type PER.C6® cells. See Table 9.

Example 6

Cross-Neutralizing Activity of IgGs

In order to determine whether the selected IgGs were capable of blocking multiple influenza A strains, additional in vitro virus neutralization assays (VNA) were performed. The VNA were performed on MDCK cells (ATCC CCL-34). MDCK cells were cultured in MDCK cell culture medium (MEM medium supplemented with antibiotics, 20 mM Hepes and 0.15% (w/v) sodium bicarbonate (complete MEM medium), supplemented with 10% (v/v) fetal bovine serum). The H1 (A/WSN/33, A/New Caledonia/20/1999, A/Solomon Islands/IVR-145 (high-growth reassortant of A/Solomon Islands/3/2006), A/Brisbane/59/2007, A/NYMC/X-181 (high-growth reassortant of A/California/07/2009)), H2 (A/Env/MPU3156/05), H3 (A/Hong Kong/1/68, A/Johannesburg/33/94, A/Panama/2000/1999, A/Hiroshima/52/2005, A/Wisconsin/67/2005 and A/Brisbane/10/2007), H4 (A/WF/HK/MPA892/06), H5 (PR8-H5N1-HK97 (6:2 reassortant of A/Hong Kong/156/97 and A/PR/8/34) and A/Eurasian Wigeon/MPF461/07)), H6 (A/Eurasian Wigeon/MPD411/07), H7 (NIBRG-60 (6:2 reassortant of A/Mallard/Netherlands/12/2000) and PR8-H7N7-NY (7:1 reassortant of A/New York/107/2003 (H7N7) and A/PR/8/34)), H8 (A/Eurasian Wigeon/MPH571/08), H9 (A/Hong Kong/1073/99 and A/Chick/HK/SSP176/09), H10 (A/Chick/Germany/N/49) and H14 (PR8-H14N5 (6:2 reassortant of A/mallard/Astrakhan/263/1982 (H14N5) and A/PR/8/34)) strains that were used in the assay were all diluted to a titer of $5.7\times10^3$ TCID50/ml (50% tissue culture infective dose per ml), with the titer calculated according to the method of Spearman and Karber. The IgG preparations (200 µg/ml) were serially two-fold diluted (1:2-1:512) in complete MEM medium in quadruplicate wells. 25 µl of the respective IgG dilution was mixed with 25 µl of virus suspension (100 TCID50/25 µl) and incubated for one hour at 37° C. The suspension was then transferred in quadruplicate onto 96-well plates containing confluent MDCK cultures in 50 µl complete MEM medium. Prior to use, MDCK cells were seeded at $3 \times 10^4$ cells per well in MDCK cell culture medium, grown until cells had reached confluence, washed with 300-350 µl PBS, pH 7.4 and finally 50 µl complete MEM medium was added to each well. The inoculated cells were cultured for 3-4 days at 37° C. and observed daily for the development of cytopathogenic effect (CPE). CPE was compared to the positive control.

CR9005, CR9112, CR9113 and CR9114 show heterosubtypic cross-neutralizing activity to representative strains of all tested influenza A subtypes HE H2, 113, H4, H5, H6, H7, H8, H9 and H10 viruses. See Table 10.

Example 7

Pan-Influenza Antibodies Bind to the Pre-Fusion Conformation of HA

In order to determine whether the selected IgGs were capable of binding the pre- or post-fusion conformation of the HA molecule, an in vitro pH-shift experiment was performed. For this purpose, full-length recombinant influenza A subtypes H1 (A/New Caledonia/20/99), H3 (A/Wisconsin/67/2005), H5 (A/Vietnam/1203/04), H7 (A/Netherlands/219/03) and H9 (A/Hong Kong/1073/99) HA were expressed on the surface of PER.C6® cells. To measure mAb binding to different structural HA conformations, cells were detached from the plastic support using PBS-EDTA and subsequently treated with trypsin (TRYPLE™SELECT, Gibco) for 5 minutes at RT, washed (1% BSA in PBS) and incubated for 15 minutes in citric acid—sodium phosphate buffer (pH 4.9). Cell samples were set aside after each processing step (untrypsinized/HA0; trypsinized/HA1-HA2; pH 4.9/fusion HA) and fractions of each treatment were incubated with mAb CR9114 for 1 hour. Cells were then incubated for 30 minutes with phycoerythrin-conjugated anti-human IgG (Southern Biotech) in 1% BSA. Stained cells were analyzed using a FACS Canto with FACS Diva software (Becton Dickinson).

FACS binding of IgG1s to surface-expressed HA was after sequential treatment with trypsin and pH 4.9 buffered medium and expressed as percentage binding to untreated HA (FIG. 1A). See FIG. 1A.

Antibody CR9114 shows a marked decrease in binding after pH-shift indicating specificity for an epitope present only before the low pH-induced conformational change of the HA molecule.

Figure 1B:
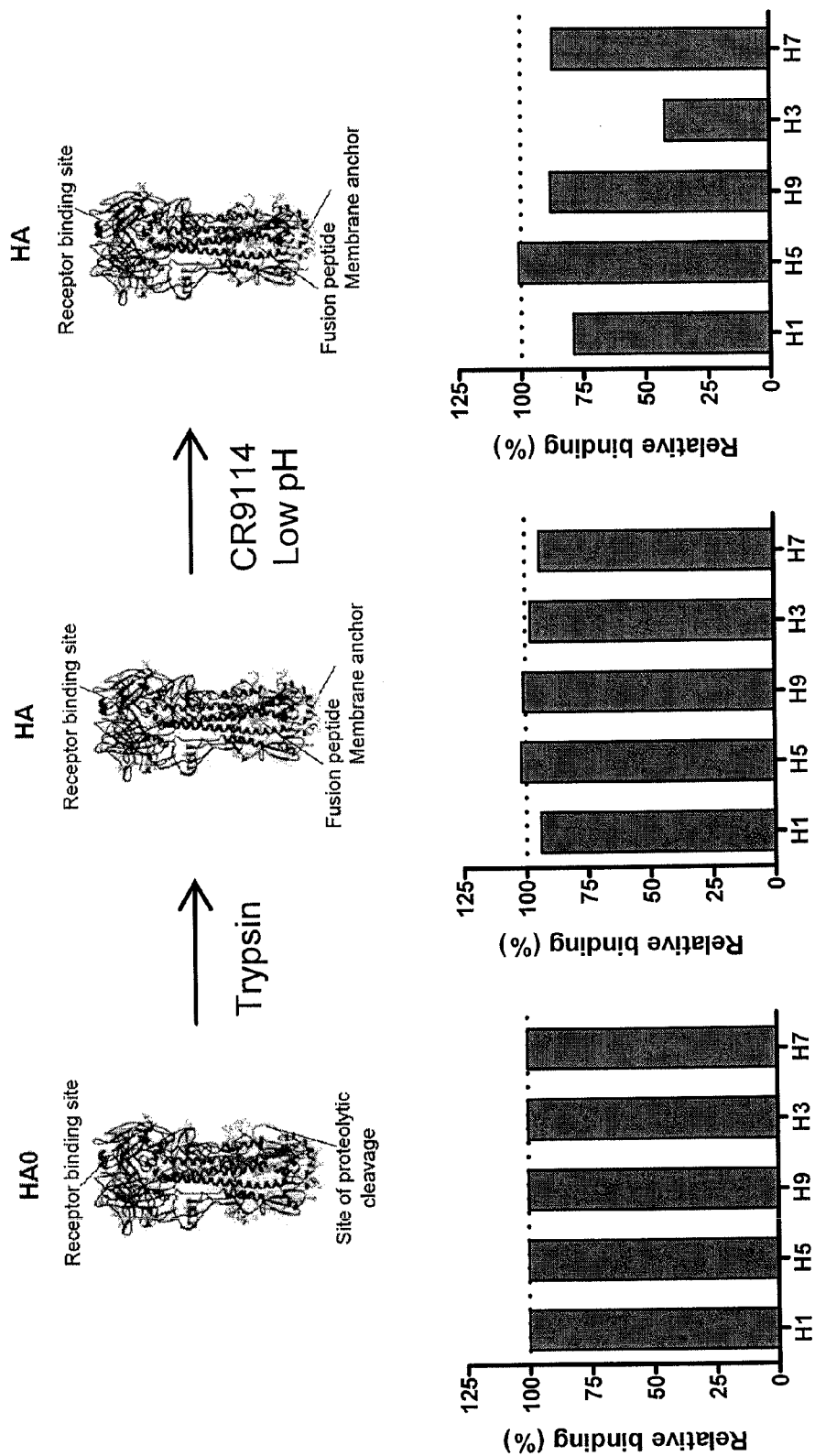
FIG. 1B: FACS binding of CR9114 to surface-expressed HA as above, except that mAb CR9114 was added before exposure of the cleaved HAs to a pH of 4.9.

Alternatively, to test whether the IgGs can block the low pH-induced conformational change of HA, antibody CR9114 was added before the low pH step. Samples of consecutive treatments were split and stained with phycoerythrin-conjugated anti-human IgG (Southern Biotech). Stained cells were analyzed using a FACS Canto with FACS Diva software (Becton Dickinson). See FIG. 1B.

Antibody CR9114 shows a high level of residual binding to the various HAs after pH shift, indicating that when these antibodies are bound to the HA molecule, the low pH-induced conformational change does not occur.

Example 8

Affinity Measurements of Fabs on Various Influenza A and B HAs

Recombinant soluble HA of A/New Caledonia/20/1999 (H1), A/Brisbane/59/2007 (H1), A/Wisconsin/67/2005 (H3), A/Brisbane/10/2007 (H3), B/Florida/4/2006 (FIG. 1B), B/Brisbane/60/2008 (FIG. 1B) and B/Malaysia/2506/2004 (FIG. 1B) produced using baculovirus vectors in insect cells were purchased from Protein Sciences Corp (CT, USA) and biotinylated at room temperature (RT) for 40 minutes using EZ-LINK® sulfo-NHS-LC-LC-biotin (Pierce). Buffer exchange step to PBS was performed using AMICON® Ultra 0.5 ml Centrifugal Filters (Millipore). Biotinylated HA was bound to Streptavidin sensors at 37° C. for 1200 seconds. Association of Fab fragment of CR9005, CR9112, CR9113 and CR9114 to HA was measured on OCTET® QK (ForteBio) for 700 seconds at 37° C. by exposing the sensors to 100 nM antibody in 1× kinetic buffer (ForteBio). Dissociation of the Fab fragments was assessed by exposing the sensors to 1× kinetic buffer for 9000 seconds at 37° C. Fab fragments of CR9005, CR9112, CR9113 and CR9114 all bind with micro- to pico-molar affinities to H1, H3 and influenza B HA.

Example 9

Competition for Binding with Other Stem Binding Antibodies

Recombinant soluble HA of A/New Caledonia/20/1999 (H1N1) and A/Wisconsin/67/2005 (H3N2) produced using baculovirus vectors in insect cells were purchased from Protein Sciences Corp (CT, USA) and biotinylated at room temperature (RT) for 40 minutes using EZ-LINK® sulfo-NHS-LC-LC-biotin (Pierce). Buffer exchange step to PBS was performed using AMICON® Ultra 0.5 ml Centrifugal Filters (Millipore). Biotinylated HA was bound to Streptavidin sensors at 37° C. for 1200 seconds. Association of antibodies CR9114 and CR6261 to H1 HA was measured on OCTET® QK (ForteBio) for 700 seconds at 37° C. by exposing the sensors to 100 nM antibody in 1× kinetic buffer (ForteBio), after which the degree of additional binding was assessed by exposing the sensors to a second antibody (100 nM in 1× kinetic buffer) in the presence of the first antibody (100 nM) for 700 seconds at 37° C. As a control, mAb CR9020, binding to the globular head of H1 was taken along. Association of antibodies CR9114 and CR8020 to H3 HA was measured on OCTET® QK (ForteBio) for 900 seconds at 37° C. by exposing the sensors to 100 nM antibody in 1× kinetic buffer (ForteBio) after which the degree of additional binding was assessed by exposing the sensors to a second antibody (100 nM in 1× kinetic buffer) in the presence of the first antibody (100 nM) for 900 seconds at 37° C. As a control, mAb CR8057, binding to the globular head of H3 was taken along.

Figure 2:
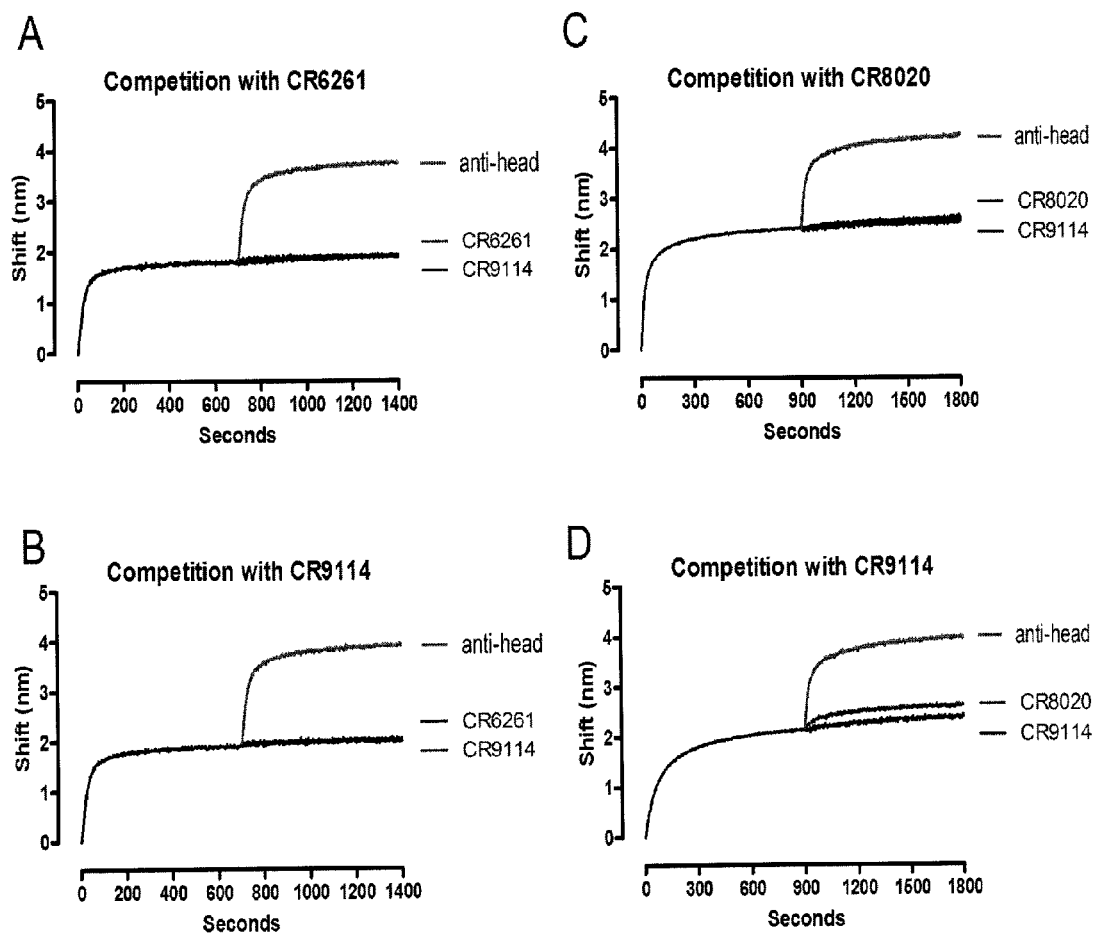
FIG. 2 shows that MAb CR9114 competes with CR6261 and CR8020 for binding to H1 and H3, respectively. Additional degree of binding of indicated mAbs to immobilized HA of A/New Caledonia/20/1999 (H1N1) saturated with 100 nM of CR6261 or CR9114 (Panels A and B), or to immobilized HA of A/Wisconsin/67/2005 (H3N2) saturated with 100 nM of CR8020 or CR9114 (Panels C and D), measured using biolayer interferometry.

CR9114 competes for binding to H1 HA with CR6261 and to H3 HA with CR8020. CR9114, therefore, likely binds an epitope overlapping with both the epitopes of CR6261 and CR8020 in the stem-region of HA. (See FIG. 2.)

Example 10

Prophylactic Activity of Human IgG Monoclonal Antibody CR9114 Against Lethal Influenza B Challenge In Vivo A study was performed to test the prophylactic effect of the monoclonal antibody CR9114 against a lethal challenge with influenza B virus in vivo. MAb CR9114 was tested for prophylactic efficacy in a mouse lethal challenge model with mouse-adapted influenza B/Florida/04/2006 virus (Central Veterinary Institute (CVI), Lelystad, The Netherlands). The B/Florida/04/2006 virus was adapted to mice after five lung-to-lung passages. The mouse-adapted influenza B passage 5 virus was propagated in embryonated chicken eggs in CVI's laboratory. All mice (Balb/c, female, age 6-8 weeks, n=10 per group) were acclimatized and maintained for a period of at least 4 days prior to the start of the experiment. MAb CR9114 was dosed at 15 mg/kg intravenously in the tail vein (vena coccygeus) at day −1 before challenge, assuming an average weight of 18 g per mouse and a fixed dose volume of 0.2 mL. A control group was taken along dosed with vehicle control. The mice were then challenged at day 0 with 25 $LD_{50}$ B/Florida/04/2006 influenza B virus by intranasal inoculation. Clinical signs and body weights were determined daily from day −1 before challenge until day 8. Clinical signs were scored with a scoring system (0=no clinical signs; 1=rough coat; 2=rough coat, less reactive during handling; 3=rough coat, rolled up, labored breathing, less reactive during handling; 4=rough coat, rolled up, labored breathing, inactive response to manipulation/handlings). At a score of 4, the animal was euthanized.

Figure 3:
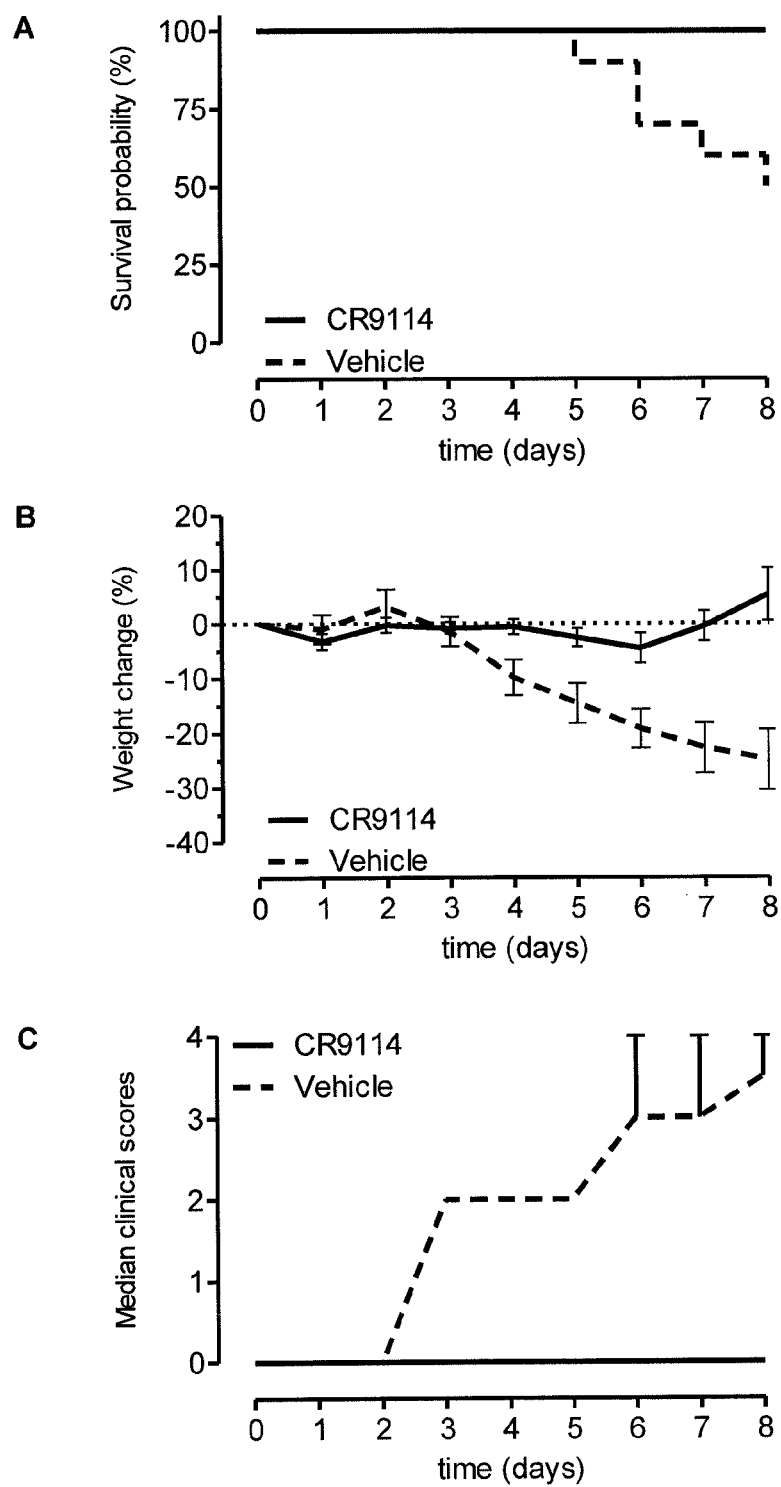
FIG. 3 demonstrates the prophylactic efficacy of CR9114 in the mouse lethal challenge model with influenza B (B/Florida/04/2006) virus. Panel A: Kaplan-Meier survival curves of mice treated intravenously with either 15 mg/kg CR9114 or vehicle control on day −1 before challenge, followed by a challenge at day 0 of 25 LD B/Florida/04/2006. Panel B: Mean bodyweight change (%) relative to day 0. Bars represent 95% CI of the mean. If a mouse died or was euthanized during the study, the last observed bodyweight was carried forward. Panel C: Median Clinical scores. Bars represent interquartile ranges. Clinical score explanation: 0=no clinical signs; 1=rough coat; 2=rough coat, less reactive during handling; 3=rough coat, rolled up, labored breathing, less reactive during handling; 4=rough coat, rolled up, labored breathing, inactive response to manipulation/handlings.

All mice were active and appeared healthy without showing signs of disease during the acclimatization period. FIG. 3, Panel A, shows the survival rates of the mice following mAb administration. Mice dosed with 15 mg/kg mAb CR9114 showed a survival rate of 100%, whereas in the control mAb group, 50% survived.

In FIG. 3, Panel B, the mean body weight change of the mice during the eight-day study period following mAb administration is shown. In the mAb CR9114 group, the mice did not lose weight over the eight-day study period, whereas in the vehicle control group, weight loss was observed. Median clinical scores of the mice are depicted in FIG. 3, Panel C. Of the mice treated with 15 mg/kg mAb CR9114 at day −1 pre-challenge, all survived and none of the animals showed any clinical signs during the observation period (from day 0 to day 8 post-infection). These results show that the human anti-influenza antibody CR9114, identified and developed as disclosed herein, is able to provide protection against a lethal dose of influenza B virus in vivo. When administered one day prior to infection at a dose of 15 mg/kg or higher, mAb CR9114 was able to completely prevent clinical manifestation of influenza B infection in mice.

TABLE 1

First round Vkappa, Vlambda and VH amplifications

| Primer name | Primer nucleotide sequence | SEQ ID NO: |
|---|---|---|
| OK1 (HuVK1B) | GAC ATC CAG WTG ACC CAG TCT CC | 65 |
| OK2 (HuVK2) | GAT GTT GTG ATG ACT CAG TCT CC | 66 |
| OK3 (HuVK2B2) | GAT ATT GTG ATG ACC CAG ACT CC | 67 |
| OK4 (HuVK3B) | GAA ATT GTG WTG ACR CAG TCT CC | 68 |
| OK5 (HuVK5) | GAA ACG ACA CTC ACG CAG TCT CC | 69 |
| OK6 (HuVK6) | GAA ATT GTG CTG ACT CAG TCT CC | 70 |
| OCK (HuCK) | ACA CTC TCC CCT GTT GAA GCT CTT | 71 |
| OL1 (HuVL1A)* | CAG TCT GTG CTG ACT CAG CCA CC | 72 |
| OL1 (HuVL1B)* | CAG TCT GTG YTG ACG CAG CCG CC | 73 |
| OL1 (HuVL1C)* | CAG TCT GTC GTG ACG CAG CCG CC | 74 |
| OL2 (HuVL2B) | CAG TCT GCC CTG ACT CAG CC | 75 |
| OL3 (HuVL3A) | TCC TAT GWG CTG ACT CAG CCA CC | 76 |
| OL4 (HuVL3B) | TCT TCT GAG CTG ACT CAG GAC CC | 77 |
| OL5 (HuVL4B) | CAG CYT GTG CTG ACT CAA TC | 78 |
| OL6 (HuVL5) | CAG GCT GTG CTG ACT CAG CCG TC | 79 |
| OL7 (HuVL6) | AAT TTT ATG CTG ACT CAG CCC CA | 80 |
| OL8 (HuVL7/8) | CAG RCT GTG GTG ACY CAG GAG CC | 81 |
| OL9 (HuVL9)# | CWG CCT GTG CTG ACT CAG CCM CC | 82 |
| OL9 (HuVL10)# | CAG GCA GGG CTG ACT CAG | 83 |
| OCL (HuCL2)X | TGA ACA TTC TGT AGG GGC CAC TG | 84 |
| OCL (HuCL7)X | AGA GCA TTC TGC AGG GGC CAC TG | 85 |
| OH1(HuVH1B7A)+ | CAG RTG CAG CTG GTG CAR TCT GG | 86 |
| OH1 (HuVH1C)+ | SAG GTC CAG CTG GTR CAG TCT GG | 87 |
| OH2 (HuVH2B) | CAG RTC ACC TTG AAG GAG TCT GG | 88 |
| OH3 (HuVH3A) | GAG GTG CAG CTG GTG GAG | 89 |
| OH4 (HuVH3C) | GAG GTG CAG CTG GTG GAG WCY GG | 90 |
| OHS (HuVH4B) | CAG GIG CAG CTA CAG CAG TGG GG | 91 |
| OH6 (HuVH4C) | CAG STG CAG CTG CAG GAG TCS GG | 92 |
| OH7 (HuVH6A) | CAG GTA CAG CTG CAG CAG TCA GG | 93 |
| OCM (HuCIgM) | TGG AAG AGG CAC GTT CTT TTC TTT | 94 |

\* Mix in 1:1:1 ratio
\# Mix in 1:1 ratio
X Mix in 1:1 ratio
+ Mix in 1:1 ratio

TABLE 2

Second round Vkappa, Vlambda and VH amplifications

| Primer name | Primer nucleotide sequence | SEQ ID NO |
|---|---|---|
| OK1S (HuVK1B-SAL) | TGA GCA CAC AGG TCG ACG GAC ATC CAG WTG ACC CAG TCT CC | 95 |
| OK2S (HuVK2-SAL) | TGA GCA CAC AGG TCG ACG GAT GTT GTG ATG ACT CAG TCT CC | 96 |

TABLE 2-continued

Second round Vkappa, Vlambda and VH amplifications

| Primer name | Primer nucleotide sequence | SEQ ID NO |
|---|---|---|
| OK3S (HuVK2B2-SAL) | TGA GCA CAC AGG TCG ACG GAT ATT GTG ATG ACC CAG ACT CC | 97 |
| OK4S (HuVK3B-SAL) | TGA GCA CAC AGG TCG ACG GAA ATT GTG WTG ACR CAG TCT CC | 98 |
| OK5S (HuVK5-SAL) | TGA GCA CAC AGG TCG ACG GAA ACG ACA CTC ACG CAG TCT CC | 99 |
| OK6S (HuVK6-SAL) | TGA GCA CAC AGG TCG ACG GAA ATT GTG CTG ACT CAG TCT CC | 100 |
| OJK1 (HuJK1-NOT) | GAG TCA TTC TCG ACT TGC GGC CGC ACG TTT GAT TTC CAC CTT GGT CCC | 101 |
| OJK2 (HuJK2-NOT) | GAG TCA TTC TCG ACT TGC GGC CGC ACG TTT GAT CTC CAG CTT GGT CCC | 102 |
| OJK3 (HuJK3-NOT) | GAG TCA TTC TCG ACT TGC GGC CGC ACG TTT GAT ATC CAC TTT GGT CCC | 103 |
| OJK4 (HuJK4-NOT) | GAG TCA TTC TCG ACT TGC GGC CGC ACG TTT GAT CTC CAC CTT GGT CCC | 104 |
| OJK5 (HuJK5-NOT) | GAG TCA TTC TCG ACT TGC GGC CGC ACG TTT AAT CTC CAG TCG TGT CCC | 105 |
| OL1S (HuVL1A-SAL)* | TGA GCA CAC AGG TCG ACG CAG TCT GTG CTG ACT CAG CCA CC | 106 |
| OL1S (HuVL1B-SAL)* | TGA GCA CAC AGG TCG ACG CAG TCT GTG YTG ACG CAG CCG CC | 107 |
| OL1S (HuVL1C-SAL)* | TGA GCA CAC AGG TCG ACG CAG TCT GTC GTG ACG CAG CCG CC | 108 |
| OL2S (HuVL2B-SAL) | TGA GCA CAC AGG TCG ACG CAG TCT GCC CTG ACT CAG CC | 109 |
| OL3S (HuVL3A-SAL) | TGA GCA CAC AGG TCG ACG TCC TAT GWG CTG ACT CAG CCA CC | 110 |
| OL4S (HuVL3B-SAL) | TGA GCA CAC AGG TCG ACG TCT TCT GAG CTG ACT CAG GAC CC | 111 |
| OL5S (HuVL4B-SAL) | TGA GCA CAC AGG TCG ACG CAG CYT GTG CTG ACT CAA TC | 112 |
| OL6S (HuVL5-SAL) | TGA GCA CAC AGG TCG ACG CAG GCT GTG CTG ACT CAG CCG TC | 113 |
| OL7S (HuVL6-SAL) | TGA GCA CAC AGG TCG ACG AAT TTT ATG CTG ACT CAG CCC CA | 114 |
| OL8S (HuVL7/8-SAL) | TGA GCA CAC AGG TCG ACG CAG RCT GTG GTG ACY CAG GAG CC | 115 |
| OL9S (HuVL9-SAL)# | TGA GCA CAC AGG TCG ACG CWG CCT GTG CTG ACT CAG CCM CC | 116 |
| OL9S (HuVL10-SAL)# | TGA GCA CAC AGG TCG ACG CAG GCA GGG CTG ACT CAG | 117 |
| OJL1 (HuJL1-NOT) | GAG TCA TTC TCG ACT TGC GGC CGC ACC TAG GAC GGT GAC CTT GGT CCC | 118 |
| OJL2 (HuJL2/3-NOT) | GAG TCA TTC TCG ACT TGC GGC CGC ACC TAG GAC GGT CAG CTT GGT CCC | 119 |
| OJL3 (HuJL7-NOT) | GAG TCA TTC TCG ACT TGC GGC CGC ACC GAG GAC GGT CAG CTG GGT GCC | 120 |
| OH1S (HuVH1B-SFI)+ | GTC CTC GCA ACT GCG GCC CAG CCG GCC ATG GCC CAG RTG CAG CTG GTG CAR TCT GG | 121 |

TABLE 2-continued

Second round Vkappa, Vlambda and VH amplifications

| Primer name | Primer nucleotide sequence | SEQ ID NO |
|---|---|---|
| OH1S (HuVH1C-SFI)+ | GTC CTC GCA ACT GCG GCC CAG CCG GCC ATG GCC SAG GTC CAG CTG GTR CAG TCT GG | 122 |
| OH2S (HuVH2B-SFI) | GTC CTC GCA ACT GCG GCC CAG CCG GCC ATG GCC CAG RTC ACC TTG AAG GAG TCT GG | 123 |
| OH3S (HuVH3A-SFI) | GTC CTC GCA ACT GCG GCC CAG CCG GCC ATG GCC GAG GTG CAG CTG GTG GAG | 124 |
| OH4S (HuVH3C-SFI) | GTC CTC GCA ACT GCG GCC CAG CCG GCC ATG GCC GAG GTG CAG CTG GTG GAG WCY GG | 125 |
| OH5S (HuVH4B-SFI) | GTC CTC GCA ACT GCG GCC CAG CCG GCC ATG GCC CAG GTG CAG CTA CAG CAG TGG GG | 126 |
| OH6S (HuVH4C-SFI) | GTC CTC GCA ACT GCG GCC CAG CCG GCC ATG GCC CAG STG CAG CTG CAG GAG TCS GG | 127 |
| OH7S (HuVH6A-SFI) | GTC CTC GCA ACT GCG GCC CAG CCG GCC ATG GCC CAG GTA CAG CTG CAG CAG TCA GG | 128 |
| OJH1 (HuJH1/2-XHO) | GAG TCA TTC TCG ACT CGA GAC RGT GAC CAG GGT GCC | 129 |
| OJH2 (HuJH3-XHO) | GAG TCA TTC TCG ACT CGA GAC GGT GAC CAT TGT CCC | 130 |
| OJH3 (HuJH4/5-XHO) | GAG TCA TTC TCG ACT CGA GAC GGT GAC CAG GGT TCC | 131 |
| OJH4 (HuJH6-XHO) | GAG TCA TTC TCG ACT CGA GAC GGT GAC CGT GGT CCC | 132 |

\* Mix in 1:1:1 ratio
\# Mix in 1:1 ratio
+ Mix in 1:1 ratio

TABLE 3

Second round VL regions amplification overview

| Template | 5' primer | 3' primer | Product | Share in PK/PL (%) | Pool | Share in VL (%) |
|---|---|---|---|---|---|---|
| K1 | OK1S | OJK1 | K1J1 | 25 | PK1 | 30 |
|  | OK1S | OJK2 | K1J2 | 25 |  |  |
|  | OK1S | OJK3 | K1J3 | 10 |  |  |
|  | OK1S | OJK4 | K1J4 | 25 |  |  |
|  | OK1S | OJK5 | K1J5 | 15 |  |  |
| K2 | OK2S | OJK1 | K2J1 | 25 | PK2 | 4 |
|  | OK2S | OJK2 | K2J2 | 25 |  |  |
|  | OK2S | OJK3 | K2J3 | 10 |  |  |
|  | OK2S | OJK4 | K2J4 | 25 |  |  |
|  | OK2S | OJK5 | K2J5 | 15 |  |  |
| K3 | OK3S | OJK1 | K3J1 | 25 | PK3 | 1 |
|  | OK3S | OJK2 | K3J2 | 25 |  |  |
|  | OK3S | OJK3 | K3J3 | 10 |  |  |
|  | OK3S | OJK4 | K3J4 | 25 |  |  |
|  | OK3S | OJK5 | K3J5 | 15 |  |  |
| K4 | OK4S | OJK1 | K4J1 | 25 | PK4 | 19 |
|  | OK4S | OJK2 | K4J2 | 25 |  |  |
|  | OK4S | OJK3 | K4J3 | 10 |  |  |
|  | OK4S | OJK4 | K4J4 | 25 |  |  |
|  | OK4S | OJK5 | K4J5 | 15 |  |  |
| K5 | OK5S | OJK1 | K5J1 | 25 | PK5 | 1 |
|  | OK5S | OJK2 | K5J2 | 25 |  |  |
|  | OK5S | OJK3 | K5J3 | 10 |  |  |
|  | OK5S | OJK4 | K5J4 | 25 |  |  |
|  | OK5S | OJK5 | K5J5 | 15 |  |  |
| K6 | OK6S | OJK1 | K6J1 | 25 | PK6 | 5 |
|  | OK6S | OJK2 | K6J2 | 25 |  |  |
|  | OK6S | OJK3 | K6J3 | 10 |  |  |
|  | OK6S | OJK4 | K6J4 | 25 |  |  |
|  | OK6S | OJK5 | K6J5 | 15 |  |  |
| L1 | OL1S | OJL1 | L1J1 | 30 | PL1 | 14 |
|  | OL1S | OJL2 | L1J2 | 60 |  |  |
|  | OL1S | OJL3 | L1J3 | 10 |  |  |
| L2 | OL2S | OJL1 | L2J1 | 30 | PL2 | 10 |
|  | OL2S | OJL2 | L2J2 | 60 |  |  |
|  | OL2S | OJL3 | L2J3 | 10 |  |  |
| L3 | OL3S | OJL1 | L3J1 | 30 | PL3 | 10 |
|  | OL3S | OJL2 | L3J2 | 60 |  |  |
|  | OL3S | OJL3 | L3J3 | 10 |  |  |
| L4 | OL4S | OJL1 | L4J1 | 30 | PL4 | 1 |
|  | OL4S | OJL2 | L4J2 | 60 |  |  |
|  | OL4S | OJL3 | L4J3 | 10 |  |  |
| L5 | OL5S | OJL1 | L5J1 | 30 | PL5 | 1 |
|  | OL5S | OJL2 | L5J2 | 60 |  |  |
|  | OL5S | OJL3 | L5J3 | 10 |  |  |
| L6 | OL6S | OJL1 | L6J1 | 30 | PL6 | 1 |
|  | OL6S | OJL2 | L6J2 | 60 |  |  |
|  | OL6S | OJL3 | L6J3 | 10 |  |  |
| L7 | OL7S | OJL1 | L7J1 | 30 | PL7 | 1 |
|  | OL7S | OJL2 | L7J2 | 60 |  |  |
|  | OL7S | OJL3 | L7J3 | 10 |  |  |
| L8 | OL8S | OJL1 | L8J1 | 30 | PL8 | 1 |
|  | OL8S | OJL2 | L8J2 | 60 |  |  |
|  | OL8S | OJL3 | L8J3 | 10 |  |  |
| L9 | OL9S | OJL1 | L9J1 | 30 | PL9 | 1 |
|  | OL9S | OJL2 | L9J2 | 60 |  |  |
|  | OL9S | OJL3 | L9J3 | 10 |  |  |
|  |  |  |  |  | VL | 100% |

TABLE 4

Second round VH regions amplification overview

| Template | 5' primer | 3' primer | Product | Share in PK/PL (%) | Pool | Share in VH (%) |
|---|---|---|---|---|---|---|
| H1 | OH1S | OJH1 | H1J1 | 10 | PH1 | 25 |
|    | OH1S | OJH2 | H1J2 | 10 |     |    |
|    | OH1S | OJH3 | H1J3 | 60 |     |    |
|    | OH1S | OJH4 | H1J4 | 20 |     |    |
| H2 | OH2S | OJH1 | H2J1 | 10 | PH2 | 2  |
|    | OH2S | OJH2 | H2J2 | 10 |     |    |
|    | OH2S | OJH3 | H2J3 | 60 |     |    |
|    | OH2S | OJH4 | H2J4 | 20 |     |    |
| H3 | OH3S | OJH1 | H3J1 | 10 | PH3 | 25 |
|    | OH3S | OJH2 | H3J2 | 10 |     |    |
|    | OH3S | OJH3 | H3J3 | 60 |     |    |
|    | OH3S | OJH4 | H3J4 | 20 |     |    |
| H4 | OH4S | OJH1 | H4J1 | 10 | PH4 | 25 |
|    | OH4S | OJH2 | H4J2 | 10 |     |    |
|    | OH4S | OJH3 | H4J3 | 60 |     |    |
|    | OH4S | OJH4 | H4J4 | 20 |     |    |
| H5 | OH5S | OJH1 | H5J1 | 10 | PH5 | 2  |
|    | OH5S | OJH2 | H5J2 | 10 |     |    |
|    | OH5S | OJH3 | H5J3 | 60 |     |    |
|    | OH5S | OJH4 | H5J4 | 20 |     |    |
| H6 | OH6S | OJH1 | H6J1 | 10 | PH6 | 20 |
|    | OH6S | OJH2 | H6J2 | 10 |     |    |
|    | OH6S | OJH3 | H6J3 | 60 |     |    |
|    | OH6S | OJH4 | H6J4 | 20 |     |    |
| H7 | OH7S | OJH1 | H7J1 | 10 | PH7 | 1  |
|    | OH7S | OJH2 | H7J2 | 10 |     |    |
|    | OH7S | OJH3 | H7J3 | 60 |     |    |
|    | OH7S | OJH4 | H7J4 | 20 |     |    |
|    |      |      |      |    | VH  | 100% |

TABLE 5

Cross-binding activity of PEG/NACl-precipitated and filter-sterilized single-chain phage antibodies to HA of different subtypes, as measured by ELISA. + = binding (>4x background); +/− = low binding (2-4x background) − = no detectable binding; H1 = HA of influenza A H1 subtype; H3 = HA of influenza A H3 subtype; H5 = HA of influenza A H5 subtype; H7 = HA of influenza A H7 subtype; B = HA of influenza virus B; Rabies = Glycoprotein of Rabies virus (negative control).

| | Phage midi Elisa | | | | | |
|---|---|---|---|---|---|---|
| | H1 | H3 | H5 | H7 | B | Rabies |
| sc09-003 | + | + | + | + | + | − |
| sc09-004 | + | + | + | + | + | − |
| sc09-005 | + | + | + | + | + | − |
| sc09-006 | + | + | + | + | + | − |
| sc09-007 | + | +/− | + | + | +/− | − |
| sc09-008 | + | +/− | + | + | +/− | − |
| sc09-009 | + | +/− | + | + | +/− | − |
| sc09-010 | + | + | + | + | +/− | − |
| sc09-011 | + | + | + | + | + | − |
| sc09-012 | + | + | + | + | − | − |
| sc09-029 | + | +/− | + | + | − | − |
| sc09-030 | + | + | + | + | + | − |
| sc09-031 | + | +/− | + | + | − | − |
| sc09-112 | + | + | + | + | + | − |
| sc09-113 | + | + | + | + | + | − |
| sc09-114 | + | + | + | + | + | − |

TABLE 6

FACS analysis of PEG/NACl-precipitated and filter-sterilized phage antibodies.

| | Phage midi Facs (% gated UL) | | | |
|---|---|---|---|---|
| | PER.C6 ® | mH1 | mH3 | mH7 |
| sc09-003 | − | + | + | + |
| sc09-004 | − | + | + | + |
| sc09-005 | − | + | + | + |
| sc09-006 | − | + | + | + |
| sc09-007 | − | + | +/− | + |
| sc09-008 | − | + | +/− | + |
| sc09-009 | − | + | +/− | + |
| sc09-010 | − | + | + | + |
| sc09-011 | − | + | + | + |
| sc09-012 | − | + | + | + |
| sc09-029 | − | + | − | +/− |
| sc09-030 | − | + | + | + |
| sc09-031 | − | + | − | +/− |
| sc09-112 | − | + | + | + |
| sc09-113 | − | + | + | + |
| sc09-114 | − | + | + | + |

+ = binding (>4x background);
+/− = low binding (2-4x background)
− = no detectable binding;
PER.C6 ® = untransfected PER.C6 ® cells (control);
mH1, mH3, mH7 = membrane bound HA of the subtypes H1, H3 and H7 subtypes, respectively.

TABLE 7

Data of the CDR regions of the HA specific immunoglobulins. The SEQ ID NO is given between brackets.

| IgG# | VH | HC CDR1 | HC CDR2 | HC CDR3 |
|---|---|---|---|---|
| CR9003 | IGHV1-69*06 | GGTSNNFG (133) | ISPIFGST (134) | ARHGNYYFYSGMDL (135) |
| CR9004 | IGHV1-69*06 | GGTSNNYA (139) | VSPIFGST (140) | ARHGNYYYNSGMDV (141) |
| CR9005 | IGHV1-69*06 | GGTSNNYA (139) | ISPIFGST (134) | ARHGNYYYSGMDL (145) |
| CR9006 | IGHV1-69*06 | GGTSNNYA (139) | ISPIFGST (134) | ARHGNYYYSGMDL (145) |
| CR9007 | IGHV1-69*06 | GGTSNNYA (139) | ISPIFGSA (151) | ARHGNYYYSGMDV (152) |
| CR9008 | IGHV1-69*06 | GGTSNNYA (139) | ISPIFGST (134) | ARHGNYYYSGMDV (152) |
| CR9009 | IGHV1-69*06 | GGTSNNYA (139) | ISPIFGST (134) | ARHGNYYYSGMDV (152) |
| CR9010 | IGHV1-69*06 | GGTSNNYA (139) | ISPIFGST (134) | ARHGNYYYSGMDV (152) |
| CR9011 | IGHV1-69*06 | GGTSNNYA (139) | ISPIFGSA (151) | ARHGNYYYSGTDV (161) |
| CR9012 | IGHV1-69*06 | GGTSNNYA (139) | ISPIFGSA (151) | ARHGTYYYSGMDV (162) |
| CR9029 | IGHV1-69*06 | GGTSNNYA (139) | ISPIFGST (134) | ARHGNYYYSGMDV (152) |
| CR9030 | IGHV1-69*06 | GGTSNNYA (139) | ISPIFGST (134) | ARHGNYYYSGMDV (152) |
| CR9031 | IGHV1-69*06 | GGTSNNYA (139) | ISPIFGST (134) | ARHGNYYYNSGMDV (141) |
| CR9112 | IGHV1-69*06 | GGTSNNYA (139) | ISPIFGST (134) | ARHGNYYYSGMDV (152) |

TABLE 7-continued

Data of the CDR regions of the HA specific immunoglobulins. The SEQ ID NO is given between brackets.

| | | | | |
|---|---|---|---|---|
| CR9113 | IGHV1-69*06 | GGTSNNYA (139) | ISPIFGST (134) | ARHGNYYYYSGMDL (145) |
| CR9114 | IGHV1-69*06 | GGTSNNYA (139) | ISPIFGST (134) | ARHGNYYYYSGMDV (152) |
| IgG# | VL | LC CDR1 | LC CDR2 | LC CDR3 |
| CR9003 | IGLV3-21*02 | NVGSNS (136) | DDR (137) | QVWDSSSDHRV (138) |
| CR9004 | IGLV1-44*01 | DSNIGRRS (142) | SND (143) | AAWDDSLKGAV (144) |
| CR9005 | IGLV2-14*01 | SSDVGGYNY (146) | DVS (174) | CSYAGSAKGV (147) |
| CR9006 | IGLV3-21*02 | NIGSKT (148) | GDS (149) | QVWDSSSDHPGAV (150) |
| CR9007 | IGLV1-44*01 | SSNIGSNT (153) | GDD (154) | ATWDDSLNGHV (155) |
| CR9008 | IGLV3-21*02 | NIGSKT (148) | GDS (149) | QVWDSSSDHPGAV (150) |
| CR9009 | IGKV1-12*01 | QHISSW (156) | SAS (157) | QQANSFPLT (158) |
| CR9010 | IGLV3-21*02 | NIGSKT (148) | VDS (159) | QVWDSNSDHPGAV (160) |
| CR9011 | IGLV1-44*01 | DSNIGRRS (142) | SND (143) | AAWDDSLKGAV (144) |
| CR9012 | IGLV1-40*02 | SSNIGAGYD (163) | GNN (164) | QSYDQNLSEGV (165) |
| CR9029 | IGKV3-20*01 | QSVSSY (166) | GAS (167) | QQYGSSPFA (168) |
| CR9030 | IGLV3-21*02 | NIGSKS (169) | GDS (149) | QVWDSSSDHPGAV (150) |
| CR9031 | IGLV1-40*01 | SSNIGAGYD (163) | DNN (169) | QSYDSGLSASPYV (170) |
| CR9112 | IGLV1-40*01 | SANIGAGYD (171) | GNN (164) | QSYDSSLSGAL (172) |
| CR9113 | IGLV1-44*01 | DSNIGRRS (142) | SND (143) | AAWDASLSGPV (173) |
| CR9114 | IGLV1-44*01 | DSNIGRRS (142) | SND (143) | AAWDDSLKGAV (144) |

TABLE 8

Identity cross-tables of the amino acid sequences of the heavy and light chain variable domains.

A.

Amino acid differences in Heavy Chain

| | | SC09-007 | SC09-011 | SC09-112 | SC09-004 | SC09-010 | SC09-113 | SC09-029 | SC09-008 | SC09-030 | SC09-114 | SC09-009 | SC09-031 | SC09-005 | SC09-006 | SC09-012 | SC09-113 | SC09-003 |
|---|---|---|---|---|---|---|---|---|---|---|---|---|---|---|---|---|---|---|
| Percentage identity | SC09-007 | | 2 | 3 | 2 | 5 | 5 | 5 | 6 | 5 | 4 | 5 | 6 | 7 | 9 | 3 | 11 | 15 |
| | SC09-011 | 98.4 | | 5 | 2 | 5 | 5 | 5 | 6 | 7 | 6 | 7 | 8 | 9 | 9 | 3 | 13 | 15 |
| | SC09-112 | 97.5 | 95.9 | | | | | 2 | 3 | 2 | 1 | 2 | 3 | 4 | 6 | 6 | 8 | 12 |
| | SC09-004 | 95.9 | 95.9 | 98.4 | | | | | | | 3 | 4 | 5 | 6 | 4 | 6 | 10 | 10 |
| | SC09-010 | 95.9 | 95.9 | 98.4 | 95.5 | | | | 3 | 4 | 3 | 4 | 5 | 6 | 4 | 6 | 10 | 10 |
| | SC09-113 | 95.9 | 95.9 | 98.4 | 85.5 | 100.0 | | | 3 | 4 | 2 | 3 | 5 | 5 | 5 | 7 | 9 | 11 |
| | SC09-029 | 95.0 | 95.0 | 97.5 | 75.7 | 97.5 | 97.5 | | | | 1 | 2 | 4 | 4 | 6 | 8 | 6 | 12 |
| | SC09-008 | 95.0 | 95.0 | 98.4 | 78.4 | 97.5 | 97.5 | 96.7 | | | | | 5 | 3 | 5 | 7 | 7 | 11 |
| | SC09-030 | 95.0 | 94.2 | 99.2 | 71.7 | 96.7 | 96.7 | 96.7 | 98.4 | | | | 4 | 4 | 6 | 8 | 8 | 12 |
| | SC09-114 | 96.7 | 95.0 | 98.4 | 69.9 | 96.7 | 96.7 | 97.5 | 97.5 | 99.2 | | | 5 | 3 | 8 | 7 | 10 | 14 |
| | SC09-009 | 95.9 | 94.2 | 98.4 | 60.4 | 95.9 | 95.9 | 97.5 | 95.9 | 98.4 | 99.2 | | 3 | | 7 | 8 | 10 | 14 |
| | SC09-004 | 95.9 | 94.2 | 97.5 | 58.0 | 96.7 | 95.9 | 96.7 | 95.0 | 96.7 | 97.5 | 96.7 | | | 2 | 9 | 11 | 15 |
| | SC09-031 | 95.0 | 93.4 | 96.7 | 58.0 | 95.9 | 95.9 | 96.7 | 95.9 | 95.9 | 96.7 | 95.9 | 95.9 | | 5 | 8 | 6 | 10 |
| | SC09-005 | 94.2 | 92.6 | 96.7 | 59.8 | 94.2 | 93.4 | 96.7 | 95.9 | 96.7 | 95.9 | 95.0 | 93.4 | 94.2 | | | 8 | 8 |
| | SC09-006 | 92.6 | 92.6 | 95.0 | 53.6 | 95.0 | 95.0 | 95.0 | 94.2 | 94.2 | 94.2 | 93.4 | 93.4 | 93.4 | 98.4 | | 8 | 14 |
| | SC09-012 | 97.5 | 97.5 | 95.0 | 57.7 | 91.7 | 91.7 | 91.7 | 92.6 | 93.4 | 94.2 | 93.4 | 92.6 | 94.2 | 93.4 | 93.4 | | |
| | SC09-113 | 90.9 | 89.3 | 93.4 | 45.1 | 91.7 | 91.7 | 91.7 | 92.6 | 93.4 | 94.2 | 93.4 | 92.6 | 95.0 | 93.4 | 93.4 | 90.1 | |
| | SC09-003 | 87.6 | 87.6 | 90.1 | 43.4 | 91.7 | 91.7 | 91.7 | 90.9 | 90.1 | 90.9 | 90.1 | 87.6 | 88.4 | 91.7 | 93.4 | 88.4 | 93.4 | 8 |

B.

Amino acid differences in Light Chain

| | | SC09-011 | SC09-114 | SC09-004 | SC09-113 | SC09-007 | SC09-012 | SC09-112 | SC09-031 | SC09-005 | SC09-006 | SC09-008 | SC09-030 | SC09-010 | SC09-003 | SC09-009 | SC09-029 |
|---|---|---|---|---|---|---|---|---|---|---|---|---|---|---|---|---|---|
| Percentage identity | SC09-011 | | 0 | 2 | 7 | 14 | 29 | 26 | 34 | 44 | 47 | 47 | 45 | 52 | 47 | 62 | 64 |
| | SC09-114 | 100.0 | | 2 | 7 | 14 | 29 | 26 | 34 | 44 | 47 | 47 | 45 | 52 | 47 | 62 | 64 |
| | SC09-004 | 98.2 | 98.2 | | 5 | 16 | 27 | 24 | 32 | 42 | 49 | 49 | 47 | 54 | 49 | 62 | 64 |
| | SC09-113 | 93.6 | 93.6 | 95.5 | | 17 | 25 | 22 | 29 | 41 | 46 | 46 | 44 | 51 | 47 | 62 | 64 |
| | SC09-007 | 87.3 | 87.3 | 85.5 | 84.6 | | 26 | 25 | 32 | 42 | 41 | 41 | 41 | 47 | 43 | 61 | 61 |
| | SC09-012 | 73.9 | 73.9 | 75.7 | 77.5 | 76.6 | | 9 | 13 | 39 | 48 | 48 | 47 | 52 | 48 | 61 | 62 |
| | SC09-112 | 76.6 | 76.6 | 78.4 | 80.2 | 77.5 | 91.9 | | 13 | 37 | 45 | 45 | 44 | 51 | 45 | 60 | 60 |
| | SC09-031 | 69.9 | 69.9 | 71.7 | 74.3 | 71.7 | 88.5 | 88.5 | | 37 | 50 | 50 | 49 | 53 | 46 | 64 | 62 |
| | SC09-005 | 60.4 | 60.4 | 62.2 | 63.1 | 62.2 | 64.9 | 66.7 | 67.3 | | 55 | 55 | 54 | 56 | 46 | 64 | 63 |
| | SC09-006 | 58.0 | 58.0 | 56.3 | 58.9 | 63.4 | 57.5 | 60.2 | 55.8 | 51.3 | | 0 | 3 | 7 | 17 | 64 | 61 |
| | SC09-008 | 58.0 | 58.0 | 56.3 | 58.9 | 63.4 | 57.5 | 60.2 | 55.8 | 51.3 | 100.0 | | 3 | 7 | 17 | 64 | 61 |
| | SC09-030 | 59.8 | 59.8 | 58.0 | 60.7 | 63.4 | 58.4 | 61.1 | 56.6 | 52.2 | 97.3 | 97.3 | | 10 | 14 | 62 | 59 |
| | SC09-010 | 53.6 | 53.6 | 51.8 | 54.5 | 58.0 | 54.0 | 54.9 | 53.1 | 50.4 | 93.6 | 93.6 | 90.9 | | 22 | 67 | 67 |
| | SC09-003 | 57.7 | 57.7 | 55.9 | 57.7 | 61.3 | 57.1 | 59.8 | 59.3 | 58.6 | 84.6 | 84.6 | 87.3 | 80.0 | | 62 | 56 |
| | SC09-009 | 45.1 | 45.1 | 45.1 | 45.1 | 46.0 | 46.5 | 47.4 | 47.4 | 43.4 | 42.9 | 42.9 | 44.6 | 40.2 | 44.1 | | 34 |
| | SC09-029 | 43.4 | 43.4 | 43.4 | 43.4 | 46.0 | 45.6 | 47.4 | 45.6 | 44.3 | 45.5 | 45.5 | 47.3 | 40.2 | 49.6 | 68.2 | |

TABLE 9

Cross-binding reactivity of IgGs, as measured by ELISA and FACS.

| | IgG Elisa | | | | | | | IgG Facs | | | |
|---|---|---|---|---|---|---|---|---|---|---|---|
| | H1 | H3 | H5 | H7 | H9 | B | Rabies | PerC6 | mH1 | mH3 | mH7 |
| CR9005 | + | + | + | + | + | + | − | − | + | + | + |
| CR9030 | + | + | + | + | + | +/− | − | − | + | + | + |
| CR9112 | + | + | + | + | + | + | − | − | + | + | + |
| CR9113 | + | + | + | + | + | + | − | − | + | + | + |
| CR9114 | + | + | + | + | + | + | − | − | + | + | + |
| CR4098 | − | − | − | − | − | − | + | − | − | − | − |

H1 = soluble recombinant A/New Caledonia/20/1999 H1 HA;
H3 = soluble recombinant A/Wisconsin/67/2005 H3 HA;
H5 = soluble recombinant A/Vietnam/1203/04 H5 HA;
H7 = soluble recombinant A/Netherlands/219/2003 H7 HA;
H9 = soluble recombinant A/Hong Kong/1073/99 H9 HA;
B = soluble recombinant B/Ohio/01/05 influenza B HA;
Rabies = rabies glycoprotein; PER.C6 ® = untransfected PER.C6 ® cells (control);
mH1 = PER.C6 ® expressed A/New Caledonia/20/1999 H1 HA;
mH3 = PER.C6 ® expressed A/Wisconsin/67/2005 H3 HA;
mH7 = PER.C6 ® expressed A/Netherlands/219/2003 H7 HA;
ND = not done.
+ = binding (>10x background);
+/− = low binding (2-10x background) − = no detectable binding.

TABLE 10

Cross-neutralizing activity of IgGs; Titers (indicated in µg/ml) are geomean IC50 values as determined according to the Spearman-Karber method of at least duplicate experiments; >100 = not neutralizing at highest tested concentration (100 µg/ml).

| | Subtype | Strain | CR9005 | CR9112 | CR9113 | CR9114 |
|---|---|---|---|---|---|---|
| Group I | H1 | A/WSN/33 | 1.1 | 0.9 | 1.1 | 1.1 |
| | | A/New Caledonia/20/99 | 2.6 | 1.9 | 4.4 | 3.7 |
| | | A/Solomon Islands/3/2006 | 1.4 | 1.3 | 2.2 | 1.8 |
| | | A/Brisbane/59/2007 | 3.4 | 2 | 3.1 | 2.6 |
| | | A/California/7/2009 | 0.7 | 0.5 | 0.3 | 0.3 |
| | H2 | A/Env/MPU3156/05 | 8.8 | 6.3 | 8.8 | 8.8 |
| | H5 | A/Hong Kong/156/97 | 0.8 | 0.7 | 0.9 | 0.4 |
| | | A/EW/MPF461/07 | 10.5 | 10.5 | 8.8 | 10.5 |
| | H6 | A/EW/MPD411/07 | 29.7 | 10.5 | 17.7 | 10.5 |
| | H8 | A/EW/MPH571/08 | 8.8 | 8.8 | 8.8 | 8.8 |
| | H9 | A/Hong Kong/1073/99 | 6.3 | 3.7 | 3.7 | 4.4 |
| | | A/Ck/HK/SSP176/09 | 4.4 | 4.4 | 6.3 | 6.3 |
| Group II | H3 | A/Hong Kong/1/68 | 42 | 27.6 | 22.3 | 19 |
| | | A/Johannesburg/33/94 | 17.7 | 13.8 | 32.4 | 21.9 |
| | | A/Panama/2007/1999 | 28.2 | 47.5 | 47.5 | 39.9 |
| | | A/Hiroshima/52/2005 | 22.9 | 10.5 | 13.6 | 12.5 |
| | | A/Wisconsin/67/2005 | 35.4 | 29.7 | 35.4 | 32.4 |
| | | A/Brisbane/10/2007 | 11.2 | 5.6 | 9.4 | 5.6 |
| | H4 | A/WF/MPA 892/06 | 1.2 | 0.8 | 1.3 | 0.8 |
| | H7 | A/Mallard/Netherlands/12/2000 | 9.6 | 6.3 | 6.3 | 4.8 |
| | | A/New York/107/2003 | >100 | >100 | >100 | >100 |
| | H10 | A/Chick/Germany/N/49 | 29.6 | 26.5 | 19.8 | 15.7 |
| | H14 | A/Mallard/Astrakhan/263/1982 | >100 | >100 | >100 | >100 |

REFERENCES

Air M. A. (1981), Sequence relationships among the hemagglutinin genes of 12 subtypes of influenza A virus. *Proc. Natl. Acad. Sci. U.S.A.* 78(12):7639-7643.

De Kruif J. et al. (1995), Rapid selection of cell subpopulation-specific human monoclonal antibodies from a synthetic phage antibody library. *Proc. Natl. Acad. Sci. U.S.A.* 92:3938.

Ferguson et al. (2003), *Nature* 422:428-443.

Fouchier A. M. et al. (2005), Characterization of a novel influenza A virus hemagglutinin subtype (H16) obtained from black-headed gulls. *J. Virol.* 79(5):2814-2822.

The World Health Organization Global Influenza Program Surveillance Network (2005), Evolution of H5N1 Avian Influenza Viruses in Asia. *Emerg. Infect. Dis.* 11:1515-1521.

What is claimed is:

1. A polynucleotide encoding a binding molecule, wherein the binding molecule is selected from the group consisting of:
   a binding molecule comprising a heavy chain CDR1 region of SEQ ID NO:139, a heavy chain CDR2 region of SEQ ID NO:134, and a heavy chain CDR3 region of SEQ ID NO:145, and a light chain CDR1 region of SEQ ID NO: 146, a light chain CDR2 region of SEQ ID NO: 174, and a light chain CDR3 region of SEQ ID NO: 147;
   a binding molecule comprising a heavy chain CDR1 region of SEQ ID NO:139, a heavy chain CDR2 region of SEQ ID NO:134, and a heavy chain CDR3 region of SEQ ID NO:145, and a light chain CDR1 region of SEQ ID NO: 148, a light chain CDR2 region of SEQ ID NO: 149, and a light chain CDR3 region of SEQ ID NO: 150;
   a binding molecule comprising a heavy chain CDR1 region of SEQ ID NO:139, a heavy chain CDR2 region of SEQ ID NO:134, and a heavy chain CDR3 region of SEQ ID NO:145, and a light chain CDR1 region of SEQ ID NO: 142, a light chain CDR2 region of SEQ ID NO: 143, and a light chain CDR3 region of SEQ ID NO: 173;
   a binding molecule comprising a heavy chain CDR1 region of SEQ ID NO:139, a heavy chain CDR2 region of SEQ ID NO:134, and a heavy chain CDR3 region of SEQ ID NO:152, and a light chain CDR1 region of SEQ ID NO: 148, a light chain CDR2 region of SEQ ID NO: 149, and a light chain CDR3 region of SEQ ID NO: 150;
   a binding molecule comprising a heavy chain CDR1 region of SEQ ID NO:139, a heavy chain CDR2 region of SEQ ID NO:134, and a heavy chain CDR3 region of SEQ ID NO:152, and a light chain CDR1 region of SEQ ID NO: 156, a light chain CDR2 region of SEQ ID NO: 157, and a light chain CDR3 region of SEQ ID NO: 158;
   a binding molecule comprising a heavy chain CDR1 region of SEQ ID NO:139, a heavy chain CDR2 region of SEQ ID NO:134, and a heavy chain CDR3 region of SEQ ID NO:152, and a light chain CDR1 region of SEQ ID NO: 171, a light chain CDR2 region of SEQ ID NO: 164, and a light chain CDR3 region of SEQ ID NO: 172; and
   a binding molecule comprising a heavy chain CDR1 region of SEQ ID NO:139, a heavy chain CDR2 region of SEQ ID NO:134, and a heavy chain CDR3 region of SEQ ID NO:152, and a light chain CDR1 region of SEQ ID NO: 142, a light chain CDR2 region of SEQ ID NO: 143, and a light chain CDR3 region of SEQ ID NO: 144.

2. The polynucleotide of claim 1, wherein the encoded binding molecule comprises a heavy chain CDR1 region of SEQ ID NO:139, a heavy chain CDR2 region of SEQ ID NO:134, and a heavy chain CDR3 region of SEQ ID NO:145, and a light chain CDR1 region of SEQ ID NO: 146, a light chain CDR2 region of SEQ ID NO: 174, and a light chain CDR3 region of SEQ ID NO: 147.

3. The polynucleotide of claim 1, wherein the encoded binding molecule comprises a heavy chain CDR1 region of SEQ ID NO:139, a heavy chain CDR2 region of SEQ ID NO:134, and a heavy chain CDR3 region of SEQ ID NO:145, and a light chain CDR1 region of SEQ ID NO: 148, a light chain CDR2 region of SEQ ID NO: 149, and a light chain CDR3 region of SEQ ID NO: 150.

4. The polynucleotide of claim 1, wherein the encoded binding molecule comprises a heavy chain CDR1 region of SEQ ID NO:139, a heavy chain CDR2 region of SEQ ID NO:134, and a heavy chain CDR3 region of SEQ ID NO:145, and a light chain CDR1 region of SEQ ID NO: 142, a light chain CDR2 region of SEQ ID NO: 143, and a light chain CDR3 region of SEQ ID NO: 173.

5. The polynucleotide of claim 1, wherein the encoded binding molecule comprises a heavy chain CDR1 region of SEQ ID NO:139, a heavy chain CDR2 region of SEQ ID NO:134, and a heavy chain CDR3 region of SEQ ID NO:152, and a light chain CDR1 region of SEQ ID NO: 148, a light chain CDR2 region of SEQ ID NO: 149, and a light chain CDR3 region of SEQ ID NO: 150.

6. The polynucleotide of claim 1, wherein the encoded binding molecule comprises a heavy chain CDR1 region of SEQ ID NO:139, a heavy chain CDR2 region of SEQ ID NO:134, and a heavy chain CDR3 region of SEQ ID NO:152, and a light chain CDR1 region of SEQ ID NO: 156, a light chain CDR2 region of SEQ ID NO: 157, and a light chain CDR3 region of SEQ ID NO: 158.

7. The polynucleotide of claim 1, wherein the encoded binding molecule comprises a heavy chain CDR1 region of SEQ ID NO:139, a heavy chain CDR2 region of SEQ ID NO:134, and a heavy chain CDR3 region of SEQ ID NO:152, and a light chain CDR1 region of SEQ ID NO: 171, a light chain CDR2 region of SEQ ID NO: 164, and a light chain CDR3 region of SEQ ID NO: 172.

8. The polynucleotide of claim 1, wherein the encoded binding molecule comprises a heavy chain CDR1 region of SEQ ID NO:139, a heavy chain CDR2 region of SEQ ID NO:134, and a heavy chain CDR3 region of SEQ ID NO:152, and a light chain CDR1 region of SEQ ID NO: 142, a light chain CDR2 region of SEQ ID NO: 143, and a light chain CDR3 region of SEQ ID NO: 144.

* * * * *

SEQUENCE LISTING

<160> NUMBER OF SEQ ID NOS: 177

<210> SEQ ID NO 1
<211> LENGTH: 354
<212> TYPE: DNA
<213> ORGANISM: Artificial
<220> FEATURE:
<223> OTHER INFORMATION: SC09-003 VH DNA

<400> SEQUENCE: 1

```
gaggtgcagc tggtggagtc tggggctgag gtcaagaagg ctgggtcctc ggtgaaagtc     60
tcctgcaagt cttctggagg cacctccaac aactttggta tcagctgggt acgacaggcc    120
cctggccaag ccttgagtg gatgggcggg atcagcccaa tctttggttc gacagtctac     180
gcacagaaat tcagggcag agtcactatt ccgcgacaga tattttcaca cactgcctac    240
atggagatga acagcctgac atctgaggac acggccgtct atttctgtgc gaggcacgga    300
aattattatt ctactccgg tatggacctc tggggccaag ggaccacggt cacc           354
```

<210> SEQ ID NO 2
<211> LENGTH: 118
<212> TYPE: PRT
<213> ORGANISM: Artificial
<220> FEATURE:
<223> OTHER INFORMATION: SC09-003 VH PROTEIN

<400> SEQUENCE: 2

```
Glu Val Gln Leu Val Glu Ser Gly Ala Glu Val Lys Lys Ala Gly Ser
1               5                   10                  15

Ser Val Lys Val Ser Cys Lys Ser Ser Gly Gly Thr Ser Asn Asn Phe
            20                  25                  30

Gly Ile Ser Trp Val Arg Gln Ala Pro Gly Gln Gly Leu Glu Trp Met
        35                  40                  45

Gly Gly Ile Ser Pro Ile Phe Gly Ser Thr Val Tyr Ala Gln Lys Phe
    50                  55                  60

Gln Gly Arg Val Thr Ile Ser Ala Asp Ile Phe Ser His Thr Ala Tyr
65                  70                  75                  80

Met Glu Met Asn Ser Leu Thr Ser Glu Asp Thr Ala Val Tyr Phe Cys
                85                  90                  95

Ala Arg His Gly Asn Tyr Tyr Phe Tyr Ser Gly Met Asp Leu Trp Gly
            100                 105                 110

Gln Gly Thr Thr Val Thr
        115
```

<210> SEQ ID NO 3
<211> LENGTH: 325
<212> TYPE: DNA
<213> ORGANISM: Artificial
<220> FEATURE:
<223> OTHER INFORMATION: SC09-003 VL DNA

<400> SEQUENCE: 3

```
tcctatgtgc tgactcagcc accctcggtg tcagtggccc caggacagac ggccacgatt     60
tcctgtgggg gagacaacgt tggaagtaac agtgtgcact ggtaccagca gaagccaggc    120
caggcccctg tgctggtcgt ctatgatgat cgcgaccgac cctcagggat ccctgagcga    180
ttctctggct ccaactctgg gaacacggcc accctgacca tcagcagggt cgaagccggg    240
gatgaggccg actattactg tcaggtgtgg gatagtagta tgatcatcg agtcttcgga    300
actgggacca aggtcaccgt cctag                                         325
```

<210> SEQ ID NO 4
<211> LENGTH: 108
<212> TYPE: PRT
<213> ORGANISM: Artificial
<220> FEATURE:
<223> OTHER INFORMATION: SC09-003 VL PROTEIN

<400> SEQUENCE: 4

Ser Tyr Val Leu Thr Gln Pro Pro Ser Val Ser Val Ala Pro Gly Gln
1               5                   10                  15

Thr Ala Thr Ile Ser Cys Gly Gly Asp Asn Val Gly Ser Asn Ser Val
            20                  25                  30

His Trp Tyr Gln Gln Lys Pro Gly Gln Ala Pro Val Leu Val Val Tyr
        35                  40                  45

Asp Asp Arg Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Asp His
                85                  90                  95

Arg Val Phe Gly Thr Gly Thr Lys Val Thr Val Leu
            100                 105

<210> SEQ ID NO 5
<211> LENGTH: 354
<212> TYPE: DNA
<213> ORGANISM: Artificial
<220> FEATURE:
<223> OTHER INFORMATION: SC09-004 VH DNA

<400> SEQUENCE: 5
caggtccagc tggtacagtc tggggctgag gtgaagaagc ctgggtcctc ggtgaaagtc      60
tcctgcaagt cttctggcgg cacctccaat aactatgcca tcagctgggt gcgacaggcc    120
cctggacaag gccttgactg gatgggcggg gtcagcccta tctttggttc gacagcctac    180
gcacagaagt tccagggcag agtcactatt ccgcggaca tattttcgaa cacagcctac     240
atggagctga acagtctgac atctgaggac acggccgtct attattgtgc gagacacggg    300
aattattatt acaactccgg tatggacgtc tggggccaag ggaccacggt cacc           354

<210> SEQ ID NO 6
<211> LENGTH: 118
<212> TYPE: PRT
<213> ORGANISM: Artificial
<220> FEATURE:
<223> OTHER INFORMATION: SC09-004 VH PROTEIN

<400> SEQUENCE: 6

Gln Val Gln Leu Val Gln Ser Gly Ala Glu Val Lys Lys Pro Gly Ser
1               5                   10                  15

Ser Val Lys Val Ser Cys Lys Ser Ser Gly Gly Thr Ser Asn Asn Tyr
            20                  25                  30

Ala Ile Ser Trp Val Arg Gln Ala Pro Gly Gln Gly Leu Asp Trp Met
        35                  40                  45

Gly Gly Val Ser Pro Ile Phe Gly Ser Thr Ala Tyr Ala Gln Lys Phe
    50                  55                  60

Gln Gly Arg Val Thr Ile Ser Ala Asp Ile Phe Ser Asn Thr Ala Tyr
65                  70                  75                  80

```
Met Glu Leu Asn Ser Leu Thr Ser Glu Asp Thr Ala Val Tyr Tyr Cys
             85                  90                  95

Ala Arg His Gly Asn Tyr Tyr Tyr Asn Ser Gly Met Asp Val Trp Gly
            100                 105                 110

Gln Gly Thr Thr Val Thr
        115

<210> SEQ ID NO 7
<211> LENGTH: 331
<212> TYPE: DNA
<213> ORGANISM: Artificial
<220> FEATURE:
<223> OTHER INFORMATION: SC09-004 VL DNA

<400> SEQUENCE: 7
cagtctgtgc tgacgcagcc gcccgcagtg tctgggaccc ccgggcagag ggtcaccatc      60
tcgtgttctg gaagtgattc aaacatcggg agaagaagtg taaactggta ccagcagttc     120
ccaggaacgg ccccccaaact cctcatctat agtaacgatc agcggccctc agtggtccct    180
gaccgattct ctggctccaa gtccggcacc tcagcctccc tggccatcag tgggctccag    240
tctgaagatg aggccgaata ttactgtgca gcatgggatg acagcctgaa gggggctgtg    300
ttcggaggag gcacccagct gaccgtcctc g                                   331

<210> SEQ ID NO 8
<211> LENGTH: 110
<212> TYPE: PRT
<213> ORGANISM: Artificial
<220> FEATURE:
<223> OTHER INFORMATION: SC09-004 VL PROTEIN

<400> SEQUENCE: 8

Gln Ser Val Leu Thr Gln Pro Pro Ala Val Ser Gly Thr Pro Gly Gln
1               5                   10                  15

Arg Val Thr Ile Ser Cys Ser Gly Ser Asp Ser Asn Ile Gly Arg Arg
            20                  25                  30

Ser Val Asn Trp Tyr Gln Gln Phe Pro Gly Thr Ala Pro Lys Leu Leu
        35                  40                  45

Ile Tyr Ser Asn Asp Gln Arg Pro Ser Val Val Pro Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Glu Tyr Tyr Cys Ala Ala Trp Asp Asp Ser Leu
                85                  90                  95

Lys Gly Ala Val Phe Gly Gly Gly Thr Gln Leu Thr Val Leu
            100                 105                 110

<210> SEQ ID NO 9
<211> LENGTH: 354
<212> TYPE: DNA
<213> ORGANISM: Artificial
<220> FEATURE:
<223> OTHER INFORMATION: SC09-005 VH DNA

<400> SEQUENCE: 9
caggtgcagc tggtgcaatc tggggctgag gtcaagaggc ctgggtcctc ggtgaaagtc      60
tcctgcaagt cttctggagg cacctccaat aactatgcta ttagtttggg tgcgacaggcc   120 cctggacaag gccttgactg gatgggcggg atcagcccta tctttggttc gacagtctac    180
gcacagaaat tccagggcag agtcactatt tccgcggaca tattttcgaa cacagcctac    240
```

```
atggagctga acagcctgac atctgaggac acggccgtat atttctgtgc gaggcacggg    300
aactattatt actactccgg tatggacctc tggggccaag ggaccacggt cacc          354
```

<210> SEQ ID NO 10
<211> LENGTH: 118
<212> TYPE: PRT
<213> ORGANISM: Artificial
<220> FEATURE:
<223> OTHER INFORMATION: SC09-005 VH PROTEIN

<400> SEQUENCE: 10

```
Gln Val Gln Leu Val Gln Ser Gly Ala Glu Val Lys Arg Pro Gly Ser
1               5                   10                  15

Ser Val Lys Val Ser Cys Lys Ser Ser Gly Gly Thr Ser Asn Asn Tyr
            20                  25                  30

Ala Ile Ser Trp Val Arg Gln Ala Pro Gly Gln Gly Leu Asp Trp Met
        35                  40                  45

Gly Gly Ile Ser Pro Ile Phe Gly Ser Thr Val Tyr Ala Gln Lys Phe
    50                  55                  60

Gln Gly Arg Val Thr Ile Ser Ala Asp Ile Phe Ser Asn Thr Ala Tyr
65                  70                  75                  80

Met Glu Leu Asn Ser Leu Thr Ser Glu Asp Thr Ala Val Tyr Phe Cys
                85                  90                  95

Ala Arg His Gly Asn Tyr Tyr Tyr Ser Gly Met Asp Leu Trp Gly
            100                 105                 110

Gln Gly Thr Thr Val Thr
        115
```

<210> SEQ ID NO 11
<211> LENGTH: 331
<212> TYPE: DNA
<213> ORGANISM: Artificial
<220> FEATURE:
<223> OTHER INFORMATION: SC09-005 VL DNA

<400> SEQUENCE: 11

```
cagtctgccc tgactcagcc tgcctccgtg tctgggtctc ctggacagtc gatcaccatc    60
tcctgcactg gaaccagcag tgacgtcggt ggttataact atgtctcctg gtaccaacaa   120
cacccaggca aagcccccaa actcctgatt tttgatgtca gtgatcggcc ctcagggggtt  180 tctgatcgct tctctggctc caagtctgcg gacacggcct ccctgaccat ctctggactc   240
caggctcagg acgaggctga ttattactgc tgctcatatg caggtagtgc caagggcgtc   300
ttcggaactg ggaccaaggt caccgtccta g                                   331
```

<210> SEQ ID NO 12
<211> LENGTH: 110
<212> TYPE: PRT
<213> ORGANISM: Artificial
<220> FEATURE:
<223> OTHER INFORMATION: SC09-005 VL PROTEIN

<400> SEQUENCE: 12

```
Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45
```

```
Leu Ile Phe Asp Val Ser Asp Arg Pro Ser Gly Val Ser Asp Arg Phe
    50                  55                  60

Ser Gly Ser Lys Ser Ala Asp Thr Ala Ser Leu Thr Ile Ser Gly Leu
65                  70                  75                  80

Gln Ala Gln Asp Glu Ala Asp Tyr Tyr Cys Cys Ser Tyr Ala Gly Ser
                85                  90                  95

Ala Lys Gly Val Phe Gly Thr Gly Thr Lys Val Thr Val Leu
            100                 105                 110

<210> SEQ ID NO 13
<211> LENGTH: 354
<212> TYPE: DNA
<213> ORGANISM: Artificial
<220> FEATURE:
<223> OTHER INFORMATION: SC09-006 VH DNA

<400> SEQUENCE: 13
gaggtgcagc tggtggagtc tggggctgag gtcaagaggc ctgggtcctc ggtgaaagtc    60
tcctgcaagt cttctggagg cacctccaat aactatgcta ttagttgggt gcgacaggcc   120
cctggacaag gccttgactg gatgggcggg atcagcccta tctttggttc gacagtctac   180
gcacagaaat tccagggcag agtcactatt ccgcggaca tattttcgaa cacagcctac    240
atggagctga acagcctgac atctgaggac acggccgtat atttctgtgc gaggcacggg   300
aactattatt actactccgg tatggacctc tggggccaag ggaccacggt cacc          354

<210> SEQ ID NO 14
<211> LENGTH: 118
<212> TYPE: PRT
<213> ORGANISM: Artificial
<220> FEATURE:
<223> OTHER INFORMATION: SC09-006 VH PROTEIN

<400> SEQUENCE: 14

Glu Val Gln Leu Val Glu Ser Gly Ala Glu Val Lys Arg Pro Gly Ser
1               5                   10                  15

Ser Val Lys Val Ser Cys Lys Ser Ser Gly Gly Thr Ser Asn Asn Tyr
            20                  25                  30

Ala Ile Ser Trp Val Arg Gln Ala Pro Gly Gln Gly Leu Asp Trp Met
        35                  40                  45

Gly Gly Ile Ser Pro Ile Phe Gly Ser Thr Val Tyr Ala Gln Lys Phe
    50                  55                  60

Gln Gly Arg Val Thr Ile Ser Ala Asp Ile Phe Ser Asn Thr Ala Tyr
65                  70                  75                  80

Met Glu Leu Asn Ser Leu Thr Ser Glu Asp Thr Ala Val Tyr Phe Cys
                85                  90                  95

Ala Arg His Gly Asn Tyr Tyr Tyr Tyr Ser Gly Met Asp Leu Trp Gly
            100                 105                 110

Gln Gly Thr Thr Val Thr
        115

<210> SEQ ID NO 15
<211> LENGTH: 331
<212> TYPE: DNA
<213> ORGANISM: Artificial
<220> FEATURE:
<223> OTHER INFORMATION: SC09-006 VL DNA

<400> SEQUENCE: 15
```

```
tcctatgtgc tgactcagcc accctcggtg tcagtggccc caggacagac ggccaggatt    60
acctgtgggg gaaacaacat tggaagtaaa actgtgcatt ggtaccagca gaactcaggc   120
caggcccctg tgctggtcgt ctatggtgat agcgaccggc cctcagggat ccctgagcga   180
ttctctggct ccaactctgg gaccacggcc accctgacca tcagcagggt cgaagccggg   240
gatgaggccg actattactg tcaggtgtgg gatagtagta gtgatcatcc cggtgctgtg   300
ttcggaggag gcacccagct gaccgtcctc g                                  331
```

<210> SEQ ID NO 16
<211> LENGTH: 110
<212> TYPE: PRT
<213> ORGANISM: Artificial
<220> FEATURE:
<223> OTHER INFORMATION: SC09-006 VL PROTEIN

<400> SEQUENCE: 16

```
Ser Tyr Val Leu Thr Gln Pro Pro Ser Val Ser Val Ala Pro Gly Gln
1               5                   10                  15

Thr Ala Arg Ile Thr Cys Gly Gly Asn Asn Ile Gly Ser Lys Thr Val
            20                  25                  30

His Trp Tyr Gln Gln Asn Ser Gly Gln Ala Pro Val Leu Val Val Tyr
        35                  40                  45

Gly Asp Ser Asp Arg Pro Ser Gly Ile Pro Glu Arg Phe Ser Gly Ser
    50                  55                  60

Asn Ser Gly Thr Thr Ala Thr Leu Thr Ile Ser Arg Val Glu Ala Gly
65                  70                  75                  80

Asp Glu Ala Asp Tyr Tyr Cys Gln Val Trp Asp Ser Ser Ser Asp His
                85                  90                  95

Pro Gly Ala Val Phe Gly Gly Gly Thr Gln Leu Thr Val Leu
            100                 105                 110
```

<210> SEQ ID NO 17
<211> LENGTH: 363
<212> TYPE: DNA
<213> ORGANISM: Artificial
<220> FEATURE:
<223> OTHER INFORMATION: SC09-007 VH DNA

<400> SEQUENCE: 17

```
caggtgcagc tggtgcaatc tggagctgag gtcaagaagc ctgggtcctc ggtgaaggtc    60
tcctgcaagt cttctggagg cacctccaat aactatgcta tcagctgggt gcgacaggcc   120
cctggacaag gccttgactg gatgggaggg atcagcccta tctttggttc agcagcctac   180
gcacagaagt tccagggcag agtcactatt accgcggaca tattttcgaa cacagtgtac   240
atggagctga acagcctgac atctgaggac acggccgtgt attactgtgc gagacacggg   300
aattattatt actactccgg tatggacgtc tggggccaag gaccacggt caccgtctcg    360 agc                                                                 363
```

<210> SEQ ID NO 18
<211> LENGTH: 121
<212> TYPE: PRT
<213> ORGANISM: Artificial
<220> FEATURE:
<223> OTHER INFORMATION: SC09-007 VH PROTEIN

<400> SEQUENCE: 18

```
Gln Val Gln Leu Val Gln Ser Gly Ala Glu Val Lys Lys Pro Gly Ser
1               5                   10                  15
```

```
Ser Val Lys Val Ser Cys Lys Ser Gly Gly Thr Ser Asn Asn Tyr
        20                  25                  30

Ala Ile Ser Trp Val Arg Gln Ala Pro Gly Gln Gly Leu Asp Trp Met
            35                  40                  45

Gly Gly Ile Ser Pro Ile Phe Gly Ser Ala Ala Tyr Ala Gln Lys Phe
 50                  55                  60

Gln Gly Arg Val Thr Ile Thr Ala Asp Ile Phe Ser Asn Thr Val Tyr
65                  70                  75                  80

Met Glu Leu Asn Ser Leu Thr Ser Glu Asp Thr Ala Val Tyr Tyr Cys
                85                  90                  95

Ala Arg His Gly Asn Tyr Tyr Tyr Ser Gly Met Asp Val Trp Gly
            100                 105                 110

Gln Gly Thr Thr Val Thr Val Ser Ser
        115                 120

<210> SEQ ID NO 19
<211> LENGTH: 331
<212> TYPE: DNA
<213> ORGANISM: Artificial
<220> FEATURE:
<223> OTHER INFORMATION: SC09-007 VL DNA

<400> SEQUENCE: 19
tcctatgtgc tgactcagcc accctcagcg tctgggaccc ccgggcagag ggtcaccatc    60
tcttgttctg gaagcagctc aacatcgga agtaatactg taaactggta ccagcaggtc   120
cccggaacgg cccccaaact cctcatctat ggtgatgatc agcggccctc agggggtccct  180 gaccgattct ctggctccaa gtctggcacc tcagcctccc tggccatcag tgggctccag   240
tctgaggatg aggctgatta ttactgtgca acatgggatg acagcctgaa tggtcatgtg   300
ttcggaggag gcacccagct gaccgtcctc g                                  331

<210> SEQ ID NO 20
<211> LENGTH: 110
<212> TYPE: PRT
<213> ORGANISM: Artificial
<220> FEATURE:
<223> OTHER INFORMATION: SC09-007 VL PROTEIN

<400> SEQUENCE: 20

Ser Tyr Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Ser Asn
            20                  25                  30

Thr Val Asn Trp Tyr Gln Gln Val Pro Gly Thr Ala Pro Lys Leu Leu
        35                  40                  45

Ile Tyr Gly Asp Asp Gln Arg Pro Ser Gly Val Pro Asp Arg Phe Ser
 50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Thr Trp Asp Asp Ser Leu
                85                  90                  95

Asn Gly His Val Phe Gly Gly Gly Thr Gln Leu Thr Val Leu
            100                 105                 110

<210> SEQ ID NO 21
<211> LENGTH: 363
<212> TYPE: DNA
```

<213> ORGANISM: Artificial
<220> FEATURE:
<223> OTHER INFORMATION: SC09-008 VH DNA

<400> SEQUENCE: 21

```
gaggtccagc tggtgcagtc tggggctgag gtcaagaagc ctgggtcctc ggtgagagtc      60
tcctgtaagt cttctggagg cacctccaat aactatgcta tcagctgggt gcgacaggcc     120
cctggacaag gccttgactg gatgggcggg atcagcccta tctttggttc gacagcctac     180
gcacagaagt tccagggcag agtcactatt ccgcggaca tattttcgaa cacagcctac     240
atggagctga acagcctgac atctgaggac acggccgtat atttctgtgc gaggcacggg     300
aattattatt actactccgg tatggacgtc tggggccaag ggaccacggt caccgtctcg     360
agc                                                                    363
```

<210> SEQ ID NO 22
<211> LENGTH: 121
<212> TYPE: PRT
<213> ORGANISM: Artificial
<220> FEATURE:
<223> OTHER INFORMATION: SC09-008 VH PROTEIN

<400> SEQUENCE: 22

Glu Val Gln Leu Val Gln Ser Gly Ala Glu Val Lys Lys Pro Gly Ser
1               5                   10                  15

Ser Val Arg Val Ser Cys Lys Ser Ser Gly Gly Thr Ser Asn Asn Tyr
            20                  25                  30

Ala Ile Ser Trp Val Arg Gln Ala Pro Gly Gln Gly Leu Asp Trp Met
        35                  40                  45

Gly Gly Ile Ser Pro Ile Phe Gly Ser Thr Ala Tyr Ala Gln Lys Phe
    50                  55                  60

Gln Gly Arg Val Thr Ile Ser Ala Asp Ile Phe Ser Asn Thr Ala Tyr
65                  70                  75                  80

Met Glu Leu Asn Ser Leu Thr Ser Glu Asp Thr Ala Val Tyr Phe Cys
                85                  90                  95

Ala Arg His Gly Asn Tyr Tyr Tyr Tyr Ser Gly Met Asp Val Trp Gly
            100                 105                 110

Gln Gly Thr Thr Val Thr Val Ser Ser
        115                 120

<210> SEQ ID NO 23
<211> LENGTH: 331
<212> TYPE: DNA
<213> ORGANISM: Artificial
<220> FEATURE:
<223> OTHER INFORMATION: SC09-008 VL DNA

<400> SEQUENCE: 23

```
tcctatgtgc tgactcagcc accctcggtg tcagtggccc caggacagac ggccaggatt      60
acctgtgggg gaaacaacat tggaagtaaa actgtgcatt ggtaccagca gaactcaggc     120
caggcccctg tgctggtcgt ctatggtgat agcgaccggc cctcagggat ccctgagcga     180
ttctctggct ccaactctgg gaccacggcc accctgacca tcagcagggt cgaagccggg     240
gatgaggccg actattactg tcaggtgtgg gatagtagta gtgatcatcc cggtgctgtg     300
ttcggaggag gcacccagct gaccgtcctc g                                    331
```

<210> SEQ ID NO 24
<211> LENGTH: 110

<212> TYPE: PRT
<213> ORGANISM: Artificial
<220> FEATURE:
<223> OTHER INFORMATION: SC09-008 VL PROTEIN

<400> SEQUENCE: 24

Ser Tyr Val Leu Thr Gln Pro Pro Ser Val Ser Val Ala Pro Gly Gln
1               5                   10                  15

Thr Ala Arg Ile Thr Cys Gly Gly Asn Asn Ile Gly Ser Lys Thr Val
            20                  25                  30

His Trp Tyr Gln Gln Asn Ser Gly Gln Ala Pro Val Leu Val Val Tyr
        35                  40                  45

Gly Asp Ser Asp Arg Pro Ser Gly Ile Pro Glu Arg Phe Ser Gly Ser
    50                  55                  60

Asn Ser Gly Thr Thr Ala Thr Leu Thr Ile Ser Arg Val Glu Ala Gly
65                  70                  75                  80

Asp Glu Ala Asp Tyr Tyr Cys Gln Val Trp Asp Ser Ser Ser Asp His
                85                  90                  95

Pro Gly Ala Val Phe Gly Gly Gly Thr Gln Leu Thr Val Leu
            100                 105                 110

<210> SEQ ID NO 25
<211> LENGTH: 363
<212> TYPE: DNA
<213> ORGANISM: Artificial
<220> FEATURE:
<223> OTHER INFORMATION: SC09-009 VH DNA

<400> SEQUENCE: 25
caggtgcagc tggtgcaatc tggggctgag gtcaagaagc ctgggtcctc ggtgaaagtc     60
tcctgcaagt cttctggagg cacctccaat aactatgcta tcagctgggt gcgacaggcc    120
cctggacaag gccttgactg gatgggcggg atcagcccta tctttggttc gacagcctac    180
gcacagaaat tccagggcag agtcactatt tccgcggaca tattttcgaa cacagcctac    240
atggagctga acagcctggc atctgaggac acggccgtat atttctgtgc gaggcacggg    300
aattattatt actactccgg tatggacgtc tggggccaag ggaccacggt caccgtctcg    360
agc                                                                   363

<210> SEQ ID NO 26
<211> LENGTH: 121
<212> TYPE: PRT
<213> ORGANISM: Artificial
<220> FEATURE:
<223> OTHER INFORMATION: SC09-009 VH PROTEIN

<400> SEQUENCE: 26

Gln Val Gln Leu Val Gln Ser Gly Ala Glu Val Lys Lys Pro Gly Ser
1               5                   10                  15

Ser Val Lys Val Ser Cys Lys Ser Ser Gly Gly Thr Ser Asn Asn Tyr
            20                  25                  30

Ala Ile Ser Trp Val Arg Gln Ala Pro Gly Gln Gly Leu Asp Trp Met
        35                  40                  45

Gly Gly Ile Ser Pro Ile Phe Gly Ser Thr Ala Tyr Ala Gln Lys Phe
    50                  55                  60

Gln Gly Arg Val Thr Ile Ser Ala Asp Ile Phe Ser Asn Thr Ala Tyr
65                  70                  75                  80

Met Glu Leu Asn Ser Leu Ala Ser Glu Asp Thr Ala Val Tyr Phe Cys
                85                  90                  95

Ala Arg His Gly Asn Tyr Tyr Tyr Ser Gly Met Asp Val Trp Gly
            100                 105                 110

Gln Gly Thr Thr Val Thr Val Ser Ser
        115                 120

<210> SEQ ID NO 27
<211> LENGTH: 322
<212> TYPE: DNA
<213> ORGANISM: Artificial
<220> FEATURE:
<223> OTHER INFORMATION: SC09-009 VL DNA

<400> SEQUENCE: 27
gacatccaga tgacccagtc tccatcttcc gtgtctgcat ctgtaggaga cagagtcacc      60
atcacttgtc gggcgagtca gcatattagc agttggttag cctggtatca gcagaagcca    120
gggaaaggcc ctcagctcct gatctattct gcatcccgtt tgcaaagtgg ggtcccatca    180
aggttcagcg gcagtggatc tgggacagat ttcactctca ccatcagcag cctgcagcct    240
gaagattttg caacttacta ttgtcaacag gctaacagtt ccccctcac tttcggccct     300 gggaccaaag tggatatcaa ac                                             322

<210> SEQ ID NO 28
<211> LENGTH: 107
<212> TYPE: PRT
<213> ORGANISM: Artificial
<220> FEATURE:
<223> OTHER INFORMATION: SC09-009 VL PROTEIN

<400> SEQUENCE: 28

Asp Ile Gln Met Thr Gln Ser Pro Ser Ser Val Ser Ala Ser Val Gly
1               5                   10                  15

Asp Arg Val Thr Ile Thr Cys Arg Ala Ser Gln His Ile Ser Ser Trp
            20                  25                  30

Leu Ala Trp Tyr Gln Gln Lys Pro Gly Lys Pro Gln Leu Leu Ile
        35                  40                  45

Tyr Ser Ala Ser Arg Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asn Ser Phe Pro Leu
                85                  90                  95

Thr Phe Gly Pro Gly Thr Lys Val Asp Ile Lys
            100                 105

<210> SEQ ID NO 29
<211> LENGTH: 363
<212> TYPE: DNA
<213> ORGANISM: Artificial
<220> FEATURE:
<223> OTHER INFORMATION: SC09-010 VH DNA

<400> SEQUENCE: 29
gaggtgcagc tggtggagtc cgggggctgag gtcaagaagc ctgggtcctc ggtgaaagtc     60
tcctgcaagt cttctggagg cacctccaat aattatgcta tcagctgggt gcgacaggcc    120
cctggacaag gccttgactg gatgggcggg atcagcccta tctttggttc gacagcctac    180
gcacagaagt tccagggcag agtcactatt tccgcggaca tattttccaa cacagcctac    240
atggagctga acagcctgac atctgaggac acggccgtat attactgtgc gaggcacggg    300

```
aattattatt actactccgg tatggacgtc tggggccaag ggaccacggt caccgtctcg      360
agc                                                                   363
```

<210> SEQ ID NO 30
<211> LENGTH: 121
<212> TYPE: PRT
<213> ORGANISM: Artificial
<220> FEATURE:
<223> OTHER INFORMATION: SC09-010 VH PROTEIN

<400> SEQUENCE: 30

```
Glu Val Gln Leu Val Glu Ser Gly Ala Glu Val Lys Lys Pro Gly Ser
1               5                   10                  15

Ser Val Lys Val Ser Cys Lys Ser Ser Gly Gly Thr Ser Asn Asn Tyr
            20                  25                  30

Ala Ile Ser Trp Val Arg Gln Ala Pro Gly Gln Gly Leu Asp Trp Met
        35                  40                  45

Gly Gly Ile Ser Pro Ile Phe Gly Ser Thr Ala Tyr Ala Gln Lys Phe
    50                  55                  60

Gln Gly Arg Val Thr Ile Ser Ala Asp Ile Phe Ser Asn Thr Ala Tyr
65                  70                  75                  80

Met Glu Leu Asn Ser Leu Thr Ser Glu Asp Thr Ala Val Tyr Tyr Cys
                85                  90                  95

Ala Arg His Gly Asn Tyr Tyr Tyr Ser Gly Met Asp Val Trp Gly
            100                 105                 110

Gln Gly Thr Thr Val Thr Val Ser Ser
        115                 120
```

<210> SEQ ID NO 31
<211> LENGTH: 331
<212> TYPE: DNA
<213> ORGANISM: Artificial
<220> FEATURE:
<223> OTHER INFORMATION: SC09-010 VL DNA

<400> SEQUENCE: 31

```
tcctatgtgc tgactcagcc accctcggtg tcagtggccc caggacagac ggccaggatt      60
acctgtgggg gaaacaacat yggaagtaaa actgtgcatt ggtaccagca gaactcaggc     120
caggcccctg tgctggtcgt ctttgttgat agcgaccgtc cctcagggat ccatgagcga     180
ttctgtggct ccaactctgg gtccacggcc accctgacca tcagcagcgt cgaagccggg     240
gatgaggccg actattactg tcaggtgtgg gatagtaata gcgatcatcc cggtgctgtg     300
ttcggaggag gcacccagct gaccgtcctc g                                    331
```

<210> SEQ ID NO 32
<211> LENGTH: 110
<212> TYPE: PRT
<213> ORGANISM: Artificial
<220> FEATURE:
<223> OTHER INFORMATION: SC09-010 VL PROTEIN

<400> SEQUENCE: 32

```
Ser Tyr Val Leu Thr Gln Pro Pro Ser Val Ser Val Ala Pro Gly Gln
1               5                   10                  15

Thr Ala Arg Ile Thr Cys Gly Gly Asn Asn Ile Gly Ser Lys Thr Val
            20                  25                  30

His Trp Tyr Gln Gln Asn Ser Gly Gln Ala Pro Val Leu Val Val Phe
        35                  40                  45
```

Val Asp Ser Asp Arg Pro Ser Gly Ile His Glu Arg Phe Cys Gly Ser
 50                  55                  60

Asn Ser Gly Ser Thr Ala Thr Leu Thr Ile Ser Ser Val Glu Ala Gly
 65                  70                  75                  80

Asp Glu Ala Asp Tyr Tyr Cys Gln Val Trp Asp Ser Asn Ser Asp His
                 85                  90                  95

Pro Gly Ala Val Phe Gly Gly Gly Thr Gln Leu Thr Val Leu
            100                 105                 110

<210> SEQ ID NO 33
<211> LENGTH: 363
<212> TYPE: DNA
<213> ORGANISM: Artificial
<220> FEATURE:
<223> OTHER INFORMATION: SC09-011 VH DNA

<400> SEQUENCE: 33

```
gaggtccagc tggtacagtc tggggctgag gtcaagaagc ctgggtcctc ggtgaaggtc      60
tcctgcaagt cttctggagg cacctccaat aactatgcta tcagctgggt gcggcaggcc     120
cctggacaag gccttgactg gatgggaggg atcagcccta tctttggttc agcagcctac     180
gcacagaagt tccagggcag agtcactatt accgcggaca tattttcgaa cacagtgtac     240
atggagctga acagcctgac atctgaggac acggccgtgt attactgtgc gagacacggg     300
aattattatt actactccgg tacggacgtc tggggccaag ggaccacggt caccgtctcg     360
agc                                                                    363
```

<210> SEQ ID NO 34
<211> LENGTH: 121
<212> TYPE: PRT
<213> ORGANISM: Artificial
<220> FEATURE:
<223> OTHER INFORMATION: SC09-011 VH PROTEIN

<400> SEQUENCE: 34

Glu Val Gln Leu Val Gln Ser Gly Ala Glu Val Lys Lys Pro Gly Ser
 1               5                  10                  15

Ser Val Lys Val Ser Cys Lys Ser Ser Gly Gly Thr Ser Asn Asn Tyr
                 20                  25                  30

Ala Ile Ser Trp Val Arg Gln Ala Pro Gly Gln Gly Leu Asp Trp Met
             35                  40                  45

Gly Gly Ile Ser Pro Ile Phe Gly Ser Ala Ala Tyr Ala Gln Lys Phe
         50                  55                  60

Gln Gly Arg Val Thr Ile Thr Ala Asp Ile Phe Ser Asn Thr Val Tyr
 65                  70                  75                  80

Met Glu Leu Asn Ser Leu Thr Ser Glu Asp Thr Ala Val Tyr Tyr Cys
                 85                  90                  95

Ala Arg His Gly Asn Tyr Tyr Tyr Ser Gly Thr Asp Val Trp Gly
            100                 105                 110

Gln Gly Thr Thr Val Thr Val Ser Ser
        115                 120

<210> SEQ ID NO 35
<211> LENGTH: 331
<212> TYPE: DNA
<213> ORGANISM: Artificial
<220> FEATURE:
<223> OTHER INFORMATION: SC09-011 VL DNA -continued

<400> SEQUENCE: 35

```
tcctatgtgc tgactcagcc acccgcagtg tctgggaccc ccgggcagag ggtcaccatc    60
tcgtgttctg gaagtgattc caacatcggg agaagaagtg taaactggta ccagcagttc   120
ccaggaacgg cccccaaact cctcatctat agtaacgatc agcggccctc agtggtccct   180
gaccgattct ctggctccaa gtccggcacc tcagcctccc tggccatcag tgggctccag   240
tctgaagatg aggccgaata ttactgtgca gcatgggatg acagcctgaa gggggctgtg   300
ttcggaggag gcacccagct gaccgtcctc g                                  331
```

<210> SEQ ID NO 36
<211> LENGTH: 110
<212> TYPE: PRT
<213> ORGANISM: Artificial
<220> FEATURE:
<223> OTHER INFORMATION: SC09-011 VL PROTEIN

<400> SEQUENCE: 36

```
Ser Tyr Val Leu Thr Gln Pro Pro Ala Val Ser Gly Thr Pro Gly Gln
1               5                   10                  15
Arg Val Thr Ile Ser Cys Ser Gly Ser Asp Ser Asn Ile Gly Arg Arg
            20                  25                  30
Ser Val Asn Trp Tyr Gln Gln Phe Pro Gly Thr Ala Pro Lys Leu Leu
        35                  40                  45
Ile Tyr Ser Asn Asp Gln Arg Pro Ser Val Val Pro Asp Arg Phe Ser
    50                  55                  60
Gly Ser Lys Ser Gly Thr Ser Ala Ser Leu Ala Ile Ser Gly Leu Gln
65                  70                  75                  80
Ser Glu Asp Glu Ala Glu Tyr Tyr Cys Ala Ala Trp Asp Asp Ser Leu
                85                  90                  95
Lys Gly Ala Val Phe Gly Gly Gly Thr Gln Leu Thr Val Leu
            100                 105                 110
```

<210> SEQ ID NO 37
<211> LENGTH: 363
<212> TYPE: DNA
<213> ORGANISM: Artificial
<220> FEATURE:
<223> OTHER INFORMATION: SC09-012 VH DNA

<400> SEQUENCE: 37

```
gaggtccagc tggtacagtc tggggctgag gtcaagaagc ctgggtcctc ggtgaaggtc    60
tcctgcaagt cttctggagg cacctccaat aattatgcta tcagctgggt gcgacaggcc   120
cctggacaag ccttgactg gatgggaggg atcagcccta ttttggttc agcagtctac   180
gcacagaagt tccagggcag agtcactatt accgcggaca tatttcgaa cacagtgtac   240
atggagctga acagcctgac atctgaggac acggccgtgt attactgtgc gagacacggg   300
acttattatt actactccgg tatggacgtc tggggccaag ggaccacggt caccgtctcg   360
agc                                                                 363
```

<210> SEQ ID NO 38
<211> LENGTH: 121
<212> TYPE: PRT
<213> ORGANISM: Artificial
<220> FEATURE:
<223> OTHER INFORMATION: SC09-012 VH PROTEIN

<400> SEQUENCE: 38

Glu Val Gln Leu Val Gln Ser Gly Ala Glu Val Lys Lys Pro Gly Ser
1               5                   10                  15

Ser Val Lys Val Ser Cys Lys Ser Gly Gly Thr Ser Asn Asn Tyr
            20                  25                  30

Ala Ile Ser Trp Val Arg Gln Ala Pro Gly Gln Gly Leu Asp Trp Met
        35                  40                  45

Gly Gly Ile Ser Pro Ile Phe Gly Ser Ala Val Tyr Ala Gln Lys Phe
50                  55                  60

Gln Gly Arg Val Thr Ile Thr Ala Asp Ile Phe Ser Asn Thr Val Tyr
65                  70                  75                  80

Met Glu Leu Asn Ser Leu Thr Ser Glu Asp Thr Ala Val Tyr Tyr Cys
                85                  90                  95

Ala Arg His Gly Thr Tyr Tyr Tyr Ser Gly Met Asp Val Trp Gly
            100                 105                 110

Gln Gly Thr Thr Val Thr Val Ser Ser
            115                 120

<210> SEQ ID NO 39
<211> LENGTH: 334
<212> TYPE: DNA
<213> ORGANISM: Artificial
<220> FEATURE:
<223> OTHER INFORMATION: SC09-012 VL DNA

<400> SEQUENCE: 39
cagtctgtcg tgacgcagcc gccctcagtg tctggggccc cagggcagag ggtcaccatc        60
tcctgcactg ggagcagctc caacatcggg gcaggttatg atgtacactg gtaccagcag       120
cttccaggga cagcccccaa actcctcatc tatggtaaca acaatcggcc ctcaggggtc       180
cctgaccgat tctctggctc caagtctggc acctcagcct ccctggccat cactgggctc       240
caggttgagg atgaggctga ttattactgc cagtcctatg accagaacct gagtgagggg       300
gtcttcggcg agggaccaa gctgaccgtc ctag                                    334

<210> SEQ ID NO 40
<211> LENGTH: 111
<212> TYPE: PRT
<213> ORGANISM: Artificial
<220> FEATURE:
<223> OTHER INFORMATION: SC09-012 VL PROTEIN

<400> SEQUENCE: 40

Gln Ser Val Val Thr Gln Pro Pro Ser Val Ser Gly Ala Pro Gly Gln
1               5                   10                  15

Arg Val Thr Ile Ser Cys Thr Gly Ser Ser Ser Asn Ile Gly Ala Gly
            20                  25                  30

Tyr Asp Val His Trp Tyr Gln Gln Leu Pro Gly Thr Ala Pro Lys Leu
        35                  40                  45

Leu Ile Tyr Gly Asn Asn Asn Arg Pro Ser Gly Val Pro Asp Arg Phe
50                  55                  60

Ser Gly Ser Lys Ser Gly Thr Ser Ala Ser Leu Ala Ile Thr Gly Leu
65                  70                  75                  80

Gln Val Glu Asp Glu Ala Asp Tyr Tyr Cys Gln Ser Tyr Asp Gln Asn
                85                  90                  95

Leu Ser Glu Gly Val Phe Gly Gly Gly Thr Lys Leu Thr Val Leu
            100                 105                 110

<210> SEQ ID NO 41

```
<211> LENGTH: 363
<212> TYPE: DNA
<213> ORGANISM: Artificial
<220> FEATURE:
<223> OTHER INFORMATION: SC09-029 VH DNA

<400> SEQUENCE: 41
gaggtgcagc tggtggagtc cgggggctgag gtcaagaagc ctgggtcctc ggtgaaagtc      60
tcctgcaagt cttctggagg cacctccaat aactatgcta tcagctgggt gcgacaggcc     120
cctggacaag gccttgactg gatgggcggg atcagcccta tctttggttc gacagcctac     180
gcacagaagt tccagggcag agtcactatt ccgcggaca tattttcgaa cacagcctac     240
atggagctga acagcctgac atctgaggac acggccgtat attactgtgc gaggcacggg     300
aattattatt actactccgg tatggacgtc tggggccaag ggaccacggt caccgtctcg     360
agc                                                                     363

<210> SEQ ID NO 42
<211> LENGTH: 121
<212> TYPE: PRT
<213> ORGANISM: Artificial
<220> FEATURE:
<223> OTHER INFORMATION: SC09-029 VH PROTEIN

<400> SEQUENCE: 42

Glu Val Gln Leu Val Glu Ser Gly Ala Glu Val Lys Lys Pro Gly Ser
1               5                   10                  15

Ser Val Lys Val Ser Cys Lys Ser Ser Gly Gly Thr Ser Asn Asn Tyr
            20                  25                  30

Ala Ile Ser Trp Val Arg Gln Ala Pro Gly Gln Gly Leu Asp Trp Met
        35                  40                  45

Gly Gly Ile Ser Pro Ile Phe Gly Ser Thr Ala Tyr Ala Gln Lys Phe
    50                  55                  60

Gln Gly Arg Val Thr Ile Ser Ala Asp Ile Phe Ser Asn Thr Ala Tyr
65                  70                  75                  80

Met Glu Leu Asn Ser Leu Thr Ser Glu Asp Thr Ala Val Tyr Tyr Cys
                85                  90                  95

Ala Arg His Gly Asn Tyr Tyr Tyr Ser Gly Met Asp Val Trp Gly
            100                 105                 110

Gln Gly Thr Thr Val Thr Val Ser Ser
        115                 120

<210> SEQ ID NO 43
<211> LENGTH: 321
<212> TYPE: DNA
<213> ORGANISM: Artificial
<220> FEATURE:
<223> OTHER INFORMATION: SC09-029 VL DNA

<400> SEQUENCE: 43
gaaattgtga tgacgcagtc tccaggcacc ctgtctttgt ctcctgggga agaggcacc      60 ctctcctgca gggccagtca gagtgttagc agctacttag cctggtacca acagaaacct    120
ggccaggctc ccaggctcct catctatggt gcatccacca gggccactgg catcccagac    180
aggttcactg gcagtgggtc tgggacagac ttcactctca ccatcagcag actggagcct   240
gaagattttg cagtgtatta ctgtcagcag tatgggagct caccattcgc tttcggccct   300
gggaccaagg tggagatcaa a                                                321
```

-continued

<210> SEQ ID NO 44
<211> LENGTH: 107
<212> TYPE: PRT
<213> ORGANISM: Artificial
<220> FEATURE:
<223> OTHER INFORMATION: SC09-029 VL PROTEIN

<400> SEQUENCE: 44

```
Glu Ile Val Met Thr Gln Ser Pro Gly Thr Leu Ser Leu Ser Pro Gly
1               5                   10                  15

Glu Arg Gly Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Asp Arg Phe Thr Gly
    50                  55                  60

Ser Gly Ser Gly Thr Asp Phe Thr Leu Thr Ile Ser Arg Leu Glu Pro
65                  70                  75                  80

Glu Asp Phe Ala Val Tyr Tyr Cys Gln Gln Tyr Gly Ser Ser Pro Phe
                85                  90                  95

Ala Phe Gly Pro Gly Thr Lys Val Glu Ile Lys
            100                 105
```

<210> SEQ ID NO 45
<211> LENGTH: 363
<212> TYPE: DNA
<213> ORGANISM: Artificial
<220> FEATURE:
<223> OTHER INFORMATION: SC09-030 VH DNA

<400> SEQUENCE: 45

```
cagatgcagc tggtgcagtc tggggctgag gtcaagaagc ctgggtcctc ggtgaaagtc      60
tcctgcaagt cttctggagg cacctccaat aactatgcta tcagctgggt gcgacaggcc    120
cctggacaag gccttgactg gatgggcggg atcagcccta tctttggttc gacagcctac    180
gcacagaagt tccagggcag agtcactatt ccgcggaca tattttcgaa cacagcctac    240
atggagctga caagcctgac atctgaggac acggccgtat atttctgtgc gaggcacggg    300
aattattatt actactccgg tatggacgtc tggggccaag ggaccacggt caccgtctcg    360
agc                                                                  363
```

<210> SEQ ID NO 46
<211> LENGTH: 121
<212> TYPE: PRT
<213> ORGANISM: Artificial
<220> FEATURE:
<223> OTHER INFORMATION: SC09-030 VH PROTEIN

<400> SEQUENCE: 46

```
Gln Met Gln Leu Val Gln Ser Gly Ala Glu Val Lys Lys Pro Gly Ser
1               5                   10                  15

Ser Val Lys Val Ser Cys Lys Ser Ser Gly Gly Thr Ser Asn Asn Tyr
            20                  25                  30

Ala Ile Ser Trp Val Arg Gln Ala Pro Gly Gln Gly Leu Asp Trp Met
        35                  40                  45

Gly Gly Ile Ser Pro Ile Phe Gly Ser Thr Ala Tyr Ala Gln Lys Phe
    50                  55                  60

Gln Gly Arg Val Thr Ile Ser Ala Asp Ile Phe Ser Asn Thr Ala Tyr
65                  70                  75                  80
```

```
Met Glu Leu Asn Ser Leu Thr Ser Glu Asp Thr Ala Val Tyr Phe Cys
                85                  90                  95

Ala Arg His Gly Asn Tyr Tyr Tyr Ser Gly Met Asp Val Trp Gly
            100                 105                 110

Gln Gly Thr Thr Val Thr Val Ser Ser
        115                 120
```

<210> SEQ ID NO 47
<211> LENGTH: 331
<212> TYPE: DNA
<213> ORGANISM: Artificial
<220> FEATURE:
<223> OTHER INFORMATION: SC09-030 VL DNA

<400> SEQUENCE: 47

```
tcctatgtgc tgactcagcc accctcggtg tcagtggccc caggacagac ggccaggatt    60
acctgtgggg gaaacaacat tggaagtaaa agtgtgcact ggtaccagca gaagccaggc   120
caggcccctg tgctggtcgt ctatggtgat agcgaccggc cctcaggat ccctgagcga    180 ttctctggct ccaactctgg gaccacggcc accctgacca tcagcagggt cgaagccggg   240
gatgaggccg actattactg tcaggtgtgg gatagtagta gtgatcatcc cggtgctgtg   300
ttcggaggag gcacccagct gaccgtcctc g                                  331
```

<210> SEQ ID NO 48
<211> LENGTH: 110
<212> TYPE: PRT
<213> ORGANISM: Artificial
<220> FEATURE:
<223> OTHER INFORMATION: SC09-030 VL PROTEIN

<400> SEQUENCE: 48

```
Ser Tyr Val Leu Thr Gln Pro Pro Ser Val Ser Val Ala Pro Gly Gln
 1               5                  10                  15

Thr Ala Arg Ile Thr Cys Gly Gly Asn Asn Ile Gly Ser Lys Ser Val
            20                  25                  30

His Trp Tyr Gln Gln Lys Pro Gly Gln Ala Pro Val Leu Val Val Tyr
        35                  40                  45

Gly Asp Ser Asp Arg Pro Ser Gly Ile Pro Glu Arg Phe Ser Gly Ser
    50                  55                  60

Asn Ser Gly Thr Thr Ala Thr Leu Thr Ile Ser Arg Val Glu Ala Gly
65                  70                  75                  80

Asp Glu Ala Asp Tyr Tyr Cys Gln Val Trp Asp Ser Ser Ser Asp His
                85                  90                  95

Pro Gly Ala Val Phe Gly Gly Gly Thr Gln Leu Thr Val Leu
            100                 105                 110
```

<210> SEQ ID NO 49
<211> LENGTH: 362
<212> TYPE: DNA
<213> ORGANISM: Artificial
<220> FEATURE:
<223> OTHER INFORMATION: SC09-031 VH DNA

<400> SEQUENCE: 49

```
caggtccagc tggtacagtc tggggctgag gtcgagaggc ctggtcctc ggtgaaagtc     60 tcctgcaagt cttctggcgg cacctccaat aactatgcca tcagctgggt gcgacaggcc   120
cctggacaag gccttgactg gatgggcggg atcagcccta tctttggttc gacagcctac   180
gcacagaagt tccagggcag agtcactatt ccgcggaca tattttcgaa cacagcctac    240
```

```
atggagctga acagtctgac atctgaggac acggccgtct attattgtgc gagacacggg    300
aattattatt acaactccgg tatggacgtc tggggccaag ggaccacggt caccgtctcg    360
ag                                                                  362
```

<210> SEQ ID NO 50
<211> LENGTH: 121
<212> TYPE: PRT
<213> ORGANISM: Artificial
<220> FEATURE:
<223> OTHER INFORMATION: SC09-031 VH PROTEIN

<400> SEQUENCE: 50

```
Gln Val Gln Leu Val Gln Ser Gly Ala Glu Val Glu Arg Pro Gly Ser
1               5                   10                  15

Ser Val Lys Val Ser Cys Lys Ser Ser Gly Thr Ser Asn Asn Tyr
            20                  25                  30

Ala Ile Ser Trp Val Arg Gln Ala Pro Gly Gln Gly Leu Asp Trp Met
        35                  40                  45

Gly Gly Ile Ser Pro Ile Phe Gly Ser Thr Ala Tyr Ala Gln Lys Phe
    50                  55                  60

Gln Gly Arg Val Thr Ile Ser Ala Asp Ile Phe Ser Asn Thr Ala Tyr
65                  70                  75                  80

Met Glu Leu Asn Ser Leu Thr Ser Glu Asp Thr Ala Val Tyr Tyr Cys
                85                  90                  95

Ala Arg His Gly Asn Tyr Tyr Tyr Asn Ser Gly Met Asp Val Trp Gly
            100                 105                 110

Gln Gly Thr Thr Val Thr Val Ser Ser
        115                 120
```

<210> SEQ ID NO 51
<211> LENGTH: 340
<212> TYPE: DNA
<213> ORGANISM: Artificial
<220> FEATURE:
<223> OTHER INFORMATION: SC09-031 VL DNA

<400> SEQUENCE: 51

```
cagtctgtgt tgacgcagcc gccctcagtg tctggggccc cagggcagag ggtcaccatc    60
tcctgcactg ggagcagctc caacatcggg gcaggttatg atgtacactg gtaccagcag    120
cttccagaaa cagccccccaa actcctcatt tatgataaca acaatcgtcc ctcagggggtt   180 tctgaccgat tctctggctc caagtctggc acttcagcct ccctggccat cactgggctc    240
caggctgagg atgaggctga ttattactgc cagtcctatg acagcggcct gagtgcttcg    300
ccttatgtct tcggagctgg gaccaaggtc accgtcctag                          340
```

<210> SEQ ID NO 52
<211> LENGTH: 113
<212> TYPE: PRT
<213> ORGANISM: Artificial
<220> FEATURE:
<223> OTHER INFORMATION: SC09-031 VL PROTEIN

<400> SEQUENCE: 52

```
Gln Ser Val Leu Thr Gln Pro Pro Ser Val Ser Gly Ala Pro Gly Gln
1               5                   10                  15

Arg Val Thr Ile Ser Cys Thr Gly Ser Ser Ser Asn Ile Gly Ala Gly
            20                  25                  30
```

Tyr Asp Val His Trp Tyr Gln Gln Leu Pro Glu Thr Ala Pro Lys Leu
            35                  40                  45

Leu Ile Tyr Asp Asn Asn Arg Pro Ser Gly Val Ser Asp Arg Phe
 50                  55                  60

Ser Gly Ser Lys Ser Gly Thr Ser Ala Ser Leu Ala Ile Thr Gly Leu
 65                  70                  75                  80

Gln Ala Glu Asp Glu Ala Asp Tyr Tyr Cys Gln Ser Tyr Asp Ser Gly
                 85                  90                  95

Leu Ser Ala Ser Pro Tyr Val Phe Gly Ala Gly Thr Lys Val Thr Val
             100                 105                 110

Leu

<210> SEQ ID NO 53
<211> LENGTH: 363
<212> TYPE: DNA
<213> ORGANISM: Artificial
<220> FEATURE:
<223> OTHER INFORMATION: SC09-112 VH DNA

<400> SEQUENCE: 53
caggtgcagc tggtgcagtc tggggctgag gtcaagaagc ctgggtcctc ggtgaaagtc     60
tcctgcaagt cttctggagg cacctccaat aactatgcta tcagctgggt gcgacaggcc    120
cctggacaag gccttgactg gatgggcggg atcagcccta tctttggttc gacagcctac    180
gcacagaagt tccagggcag agtcactatt tccgcggaca tatttcgaa cacagcctac     240 atggagctga acagcctgac atctgaggac acggccgtat attactgtgc gaggcacggg    300
aattattatt actactccgg tatggacgtc tggggccaag ggaccacggt caccgtctcg    360
agc                                                                  363

<210> SEQ ID NO 54
<211> LENGTH: 121
<212> TYPE: PRT
<213> ORGANISM: Artificial
<220> FEATURE:
<223> OTHER INFORMATION: SC09-112 VH PROTEIN

<400> SEQUENCE: 54

Gln Val Gln Leu Val Gln Ser Gly Ala Glu Val Lys Lys Pro Gly Ser
 1               5                  10                  15

Ser Val Lys Val Ser Cys Lys Ser Ser Gly Gly Thr Ser Asn Asn Tyr
                 20                  25                  30

Ala Ile Ser Trp Val Arg Gln Ala Pro Gly Gln Gly Leu Asp Trp Met
             35                  40                  45

Gly Gly Ile Ser Pro Ile Phe Gly Ser Thr Ala Tyr Ala Gln Lys Phe
 50                  55                  60

Gln Gly Arg Val Thr Ile Ser Ala Asp Ile Phe Ser Asn Thr Ala Tyr
 65                  70                  75                  80

Met Glu Leu Asn Ser Leu Thr Ser Glu Asp Thr Ala Val Tyr Tyr Cys
                 85                  90                  95

Ala Arg His Gly Asn Tyr Tyr Tyr Ser Gly Met Asp Val Trp Gly
             100                 105                 110

Gln Gly Thr Thr Val Thr Val Ser Ser
            115                 120

<210> SEQ ID NO 55
<211> LENGTH: 334
<212> TYPE: DNA

<213> ORGANISM: Artificial
<220> FEATURE:
<223> OTHER INFORMATION: SC09-112 VL DNA

<400> SEQUENCE: 55

```
cagtctgtgt tgacgcagcc gccctcagtg tctggggccc cagggcagag ggtcaccatc      60
tcctgcactg ggagcagcgc caacatcggg gcaggttatg atgtccactg gtaccagcag     120
tttccaggaa cagcccccaa actcctcatc tatggtaaca acaatcggcc ctcaggggtc     180
cctgaccgat tctctggctc caagtctggc acctcagcct ccctggccat cactgggctc     240
caggctgagg atgaggctga ttattactgc cagtcctatg acagcagcct gagtggtgcg     300
ttattcggcg gagggaccaa gctgaccgtc ctag                                 334
```

<210> SEQ ID NO 56
<211> LENGTH: 111
<212> TYPE: PRT
<213> ORGANISM: Artificial
<220> FEATURE:
<223> OTHER INFORMATION: SC09-112 VL PROTEIN

<400> SEQUENCE: 56

```
Gln Ser Val Leu Thr Gln Pro Pro Ser Val Ser Gly Ala Pro Gly Gln
  1               5                  10                  15
Arg Val Thr Ile Ser Cys Thr Gly Ser Ser Ala Asn Ile Gly Ala Gly
             20                  25                  30
Tyr Asp Val His Trp Tyr Gln Gln Phe Pro Gly Thr Ala Pro Lys Leu
         35                  40                  45
Leu Ile Tyr Gly Asn Asn Asn Arg Pro Ser Gly Val Pro Asp Arg Phe
     50                  55                  60
Ser Gly Ser Lys Ser Gly Thr Ser Ala Ser Leu Ala Ile Thr Gly Leu
 65                  70                  75                  80
Gln Ala Glu Asp Glu Ala Asp Tyr Tyr Cys Gln Ser Tyr Asp Ser Ser
                 85                  90                  95
Leu Ser Gly Ala Leu Phe Gly Gly Gly Thr Lys Leu Thr Val Leu
            100                 105                 110
```

<210> SEQ ID NO 57
<211> LENGTH: 363
<212> TYPE: DNA
<213> ORGANISM: Artificial
<220> FEATURE:
<223> OTHER INFORMATION: SC09-113 VH DNA

<400> SEQUENCE: 57

```
cagatgcagc tggtgcagtc tggggctgag gtcaagaagg ctgggtcctc ggtgaaagtc      60
tcctgcaagt cttctggagg cacctccaat aactatgcta tcagctgggt gcgacaggcc     120
cctggacaag gccttgagtg gatgggcggg atcagtccaa tctttggttc gacagtctac     180
gcacagaaat tccagggcag agtcactatt tccgcggaca tattttcaca cactgcctac     240
atggagctga acagcctgac atctgaggac acggccgcat atttctgtgc gaggcacgga     300
aactattatt actactccgg tatggacctc tggggccaag gaccacggt caccgtctcg     360
agc                                                                  363
```

<210> SEQ ID NO 58
<211> LENGTH: 121
<212> TYPE: PRT
<213> ORGANISM: Artificial
<220> FEATURE:

<223> OTHER INFORMATION: SC09-113 VH PROTEIN

<400> SEQUENCE: 58

```
Gln Met Gln Leu Val Gln Ser Gly Ala Glu Val Lys Lys Ala Gly Ser
1               5                   10                  15

Ser Val Lys Val Ser Cys Lys Ser Gly Gly Thr Ser Asn Asn Tyr
            20                  25                  30

Ala Ile Ser Trp Val Arg Gln Ala Pro Gly Gln Gly Leu Glu Trp Met
        35                  40                  45

Gly Gly Ile Ser Pro Ile Phe Gly Ser Thr Val Tyr Ala Gln Lys Phe
    50                  55                  60

Gln Gly Arg Val Thr Ile Ser Ala Asp Ile Phe Ser His Thr Ala Tyr
65                  70                  75                  80

Met Glu Leu Asn Ser Leu Thr Ser Glu Asp Thr Ala Ala Tyr Phe Cys
                85                  90                  95

Ala Arg His Gly Asn Tyr Tyr Tyr Ser Gly Met Asp Leu Trp Gly
            100                 105                 110

Gln Gly Thr Thr Val Thr Val Ser Ser
        115                 120
```

<210> SEQ ID NO 59
<211> LENGTH: 331
<212> TYPE: DNA
<213> ORGANISM: Artificial
<220> FEATURE:
<223> OTHER INFORMATION: SC09-113 VL DNA

<400> SEQUENCE: 59

```
cagtctgtgc tgactcagcc acccgcagtg tctgggaccc ccgggcagag ggtcaccatc    60
tcgtgttctg gaagtgattc aacatcggg agaagaagtg taaactggta ccagcagttc   120
ccaggaacgg cccccaaact cctcatctat agtaacgatc agcggccctc agtggtccct   180
gaccgattct ctggctccaa gtccggcacc tcagcctccc tggccatcag tgggctccag   240
gctgaggatg aggctgatta ttactgtgca gcatgggatg ccagcctgag tggtcctgtg   300
ttcggaggag gcacccagct gaccgtcctc g                                  331
```

<210> SEQ ID NO 60
<211> LENGTH: 110
<212> TYPE: PRT
<213> ORGANISM: Artificial
<220> FEATURE:
<223> OTHER INFORMATION: SC09-113 VL PROTEIN

<400> SEQUENCE: 60

```
Gln Ser Val Leu Thr Gln Pro Pro Ala Val Ser Gly Thr Pro Gly Gln
1               5                   10                  15

Arg Val Thr Ile Ser Cys Ser Gly Ser Asp Ser Asn Ile Gly Arg Arg
            20                  25                  30

Ser Val Asn Trp Tyr Gln Gln Phe Pro Gly Thr Ala Pro Lys Leu Leu
        35                  40                  45

Ile Tyr Ser Asn Asp Gln Arg Pro Ser Val Val Pro Asp Arg Phe Ser
    50                  55                  60

Gly Ser Lys Ser Gly Thr Ser Ala Ser Leu Ala Ile Ser Gly Leu Gln
65                  70                  75                  80

Ala Glu Asp Glu Ala Asp Tyr Tyr Cys Ala Ala Trp Asp Ala Ser Leu
                85                  90                  95

Ser Gly Pro Val Phe Gly Gly Gly Thr Gln Leu Thr Val Leu
```

<210> SEQ ID NO 61
<211> LENGTH: 363
<212> TYPE: DNA
<213> ORGANISM: Artificial
<220> FEATURE:
<223> OTHER INFORMATION: SC09-114 VH DNA

<400> SEQUENCE: 61

```
caggtgcagc tggtgcaatc tggggctgag gtcaagaagc ctgggtcctc ggtgaaagtc      60
tcctgcaagt cttctggagg cacctccaat aactatgcta tcagctgggt gcgacaggcc     120
cctggacaag gccttgactg gatgggcggg atcagcccta tctttggttc gacagcctac     180
gcacagaaat tccagggcag agtcactatt tccgcggaca tattttcgaa cacagcctac     240
atggagctga acagcctgac atctgaggac acggccgtat atttctgtgc gaggcacggg     300
aattattatt actactccgg tatggacgtc tggggccaag gaccacggt caccgtctcg      360
agc                                                                   363
```

<210> SEQ ID NO 62
<211> LENGTH: 121
<212> TYPE: PRT
<213> ORGANISM: Artificial
<220> FEATURE:
<223> OTHER INFORMATION: SC09-114 VH PROTEIN

<400> SEQUENCE: 62

Gln Val Gln Leu Val Gln Ser Gly Ala Glu Val Lys Lys Pro Gly Ser
1               5                   10                  15
Ser Val Lys Val Ser Cys Lys Ser Ser Gly Gly Thr Ser Asn Asn Tyr
            20                  25                  30
Ala Ile Ser Trp Val Arg Gln Ala Pro Gly Gln Gly Leu Asp Trp Met
        35                  40                  45
Gly Gly Ile Ser Pro Ile Phe Gly Ser Thr Ala Tyr Ala Gln Lys Phe
    50                  55                  60
Gln Gly Arg Val Thr Ile Ser Ala Asp Ile Phe Ser Asn Thr Ala Tyr
65                  70                  75                  80
Met Glu Leu Asn Ser Leu Thr Ser Glu Asp Thr Ala Val Tyr Phe Cys
                85                  90                  95
Ala Arg His Gly Asn Tyr Tyr Tyr Ser Gly Met Asp Val Trp Gly
            100                 105                 110
Gln Gly Thr Thr Val Thr Val Ser Ser
        115                 120

<210> SEQ ID NO 63
<211> LENGTH: 331
<212> TYPE: DNA
<213> ORGANISM: Artificial
<220> FEATURE:
<223> OTHER INFORMATION: SC09-114 VL DNA

<400> SEQUENCE: 63

```
tcctatgtgc tgactcagcc acccgcagtg tctgggaccc ccgggcagag ggtcaccatc      60
tcgtgttctg gaagtgattc aacatcggg agaagaagtg taaactggta ccagcagttc     120
ccaggaacgg cccccaaact cctcatctat agtaacgatc agcggccctc agtggtccct     180
gaccgattct ctggctccaa gtccggcacc tcagcctccc tggccatcag tgggctccag     240
tctgaagatg aggccgaata ttactgtgca gcatgggat acagcctgaa gggggctgtg     300
```

```
ttcggaggag gcacccagct gaccgtcctc g                                       331
```

<210> SEQ ID NO 64
<211> LENGTH: 110
<212> TYPE: PRT
<213> ORGANISM: Artificial
<220> FEATURE:
<223> OTHER INFORMATION: SC09-114 VL PROTEIN

<400> SEQUENCE: 64

```
Ser Tyr Val Leu Thr Gln Pro Pro Ala Val Ser Gly Thr Pro Gly Gln
1               5                   10                  15

Arg Val Thr Ile Ser Cys Ser Gly Ser Asp Ser Asn Ile Gly Arg Arg
            20                  25                  30

Ser Val Asn Trp Tyr Gln Gln Phe Pro Gly Thr Ala Pro Lys Leu Leu
        35                  40                  45

Ile Tyr Ser Asn Asp Gln Arg Pro Ser Val Val Pro Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Glu Tyr Tyr Cys Ala Ala Trp Asp Asp Ser Leu
                85                  90                  95

Lys Gly Ala Val Phe Gly Gly Gly Thr Gln Leu Thr Val Leu
            100                 105                 110
```

<210> SEQ ID NO 65
<211> LENGTH: 23
<212> TYPE: DNA
<213> ORGANISM: Artificial
<220> FEATURE:
<223> OTHER INFORMATION: OK1 (HuVK1B)

<400> SEQUENCE: 65

```
gacatccagw tgacccagtc tcc                                                23
```

<210> SEQ ID NO 66
<211> LENGTH: 23
<212> TYPE: DNA
<213> ORGANISM: Artificial
<220> FEATURE:
<223> OTHER INFORMATION: OK2 (HuVK2)

<400> SEQUENCE: 66

```
gatgttgtga tgactcagtc tcc                                                23
```

<210> SEQ ID NO 67
<211> LENGTH: 23
<212> TYPE: DNA
<213> ORGANISM: Artificial
<220> FEATURE:
<223> OTHER INFORMATION: OK3 (HuVK2B2)

<400> SEQUENCE: 67

```
gatattgtga tgacccagac tcc                                                23
```

<210> SEQ ID NO 68
<211> LENGTH: 23
<212> TYPE: DNA
<213> ORGANISM: Artificial
<220> FEATURE:
<223> OTHER INFORMATION: OK4 (HuVK3B)

<400> SEQUENCE: 68

```
gaaattgtgw tgacrcagtc tcc                                              23

<210> SEQ ID NO 69
<211> LENGTH: 23
<212> TYPE: DNA
<213> ORGANISM: Artificial
<220> FEATURE:
<223> OTHER INFORMATION: OK5 (HuVK5)

<400> SEQUENCE: 69
gaaacgacac tcacgcagtc tcc                                              23

<210> SEQ ID NO 70
<211> LENGTH: 23
<212> TYPE: DNA
<213> ORGANISM: Artificial
<220> FEATURE:
<223> OTHER INFORMATION: OK6 (HuVK6)

<400> SEQUENCE: 70
gaaattgtgc tgactcagtc tcc                                              23

<210> SEQ ID NO 71
<211> LENGTH: 24
<212> TYPE: DNA
<213> ORGANISM: Artificial
<220> FEATURE:
<223> OTHER INFORMATION: OCK (HuCK)

<400> SEQUENCE: 71
acactctccc ctgttgaagc tctt                                             24

<210> SEQ ID NO 72
<211> LENGTH: 23
<212> TYPE: DNA
<213> ORGANISM: Artificial
<220> FEATURE:
<223> OTHER INFORMATION: OL1 (HuVL1A)

<400> SEQUENCE: 72
cagtctgtgc tgactcagcc acc                                              23

<210> SEQ ID NO 73
<211> LENGTH: 23
<212> TYPE: DNA
<213> ORGANISM: Artificial
<220> FEATURE:
<223> OTHER INFORMATION: OL1 (HuVL1B)

<400> SEQUENCE: 73
cagtctgtgy tgacgcagcc gcc                                              23

<210> SEQ ID NO 74
<211> LENGTH: 23
<212> TYPE: DNA
<213> ORGANISM: Artificial
<220> FEATURE:
<223> OTHER INFORMATION: OL1 (HuVL1C)

<400> SEQUENCE: 74
cagtctgtcg tgacgcagcc gcc                                              23

<210> SEQ ID NO 75
<211> LENGTH: 20
<212> TYPE: DNA
```

```
<213> ORGANISM: Artificial
<220> FEATURE:
<223> OTHER INFORMATION: OL2 (HuVL2B)

<400> SEQUENCE: 75
cagtctgccc tgactcagcc                                               20

<210> SEQ ID NO 76
<211> LENGTH: 23
<212> TYPE: DNA
<213> ORGANISM: Artificial
<220> FEATURE:
<223> OTHER INFORMATION: OL3 (HuVL3A)

<400> SEQUENCE: 76
tcctatgwgc tgactcagcc acc                                           23

<210> SEQ ID NO 77
<211> LENGTH: 23
<212> TYPE: DNA
<213> ORGANISM: Artificial
<220> FEATURE:
<223> OTHER INFORMATION: OL4 (HuVL3B)

<400> SEQUENCE: 77
tcttctgagc tgactcagga ccc                                           23

<210> SEQ ID NO 78
<211> LENGTH: 20
<212> TYPE: DNA
<213> ORGANISM: Artificial
<220> FEATURE:
<223> OTHER INFORMATION: OL5 (HuVL4B)

<400> SEQUENCE: 78
cagcytgtgc tgactcaatc                                               20

<210> SEQ ID NO 79
<211> LENGTH: 23
<212> TYPE: DNA
<213> ORGANISM: Artificial
<220> FEATURE:
<223> OTHER INFORMATION: OL6 (HuVL5)

<400> SEQUENCE: 79
caggctgtgc tgactcagcc gtc                                           23

<210> SEQ ID NO 80
<211> LENGTH: 23
<212> TYPE: DNA
<213> ORGANISM: Artificial
<220> FEATURE:
<223> OTHER INFORMATION: OL7 (HuVL6)

<400> SEQUENCE: 80
aattttatgc tgactcagcc cca                                           23

<210> SEQ ID NO 81
<211> LENGTH: 23
<212> TYPE: DNA
<213> ORGANISM: Artificial
<220> FEATURE:
<223> OTHER INFORMATION: OL8 (HuVL7/8)

<400> SEQUENCE: 81
cagrctgtgg tgacycagga gcc                                           23
```

<210> SEQ ID NO 82
<211> LENGTH: 23
<212> TYPE: DNA
<213> ORGANISM: Artificial
<220> FEATURE:
<223> OTHER INFORMATION: OL9 (HuVL9)

<400> SEQUENCE: 82
cwgcctgtgc tgactcagcc mcc                                              23

<210> SEQ ID NO 83
<211> LENGTH: 18
<212> TYPE: DNA
<213> ORGANISM: Artificial
<220> FEATURE:
<223> OTHER INFORMATION: OL9 (HuVL10

<400> SEQUENCE: 83
caggcagggc tgactcag                                                    18

<210> SEQ ID NO 84
<211> LENGTH: 23
<212> TYPE: DNA
<213> ORGANISM: Artificial
<220> FEATURE:
<223> OTHER INFORMATION: OCL (HuCL2)

<400> SEQUENCE: 84
tgaacattct gtaggggcca ctg                                              23

<210> SEQ ID NO 85
<211> LENGTH: 23
<212> TYPE: DNA
<213> ORGANISM: Artificial
<220> FEATURE:
<223> OTHER INFORMATION: OCL (HuCL7)

<400> SEQUENCE: 85
agagcattct gcaggggcca ctg                                              23

<210> SEQ ID NO 86
<211> LENGTH: 23
<212> TYPE: DNA
<213> ORGANISM: Artificial
<220> FEATURE:
<223> OTHER INFORMATION: OH1(HuVH1B7A)

<400> SEQUENCE: 86
cagrtgcagc tggtgcartc tgg                                              23

<210> SEQ ID NO 87
<211> LENGTH: 23
<212> TYPE: DNA
<213> ORGANISM: Artificial
<220> FEATURE:
<223> OTHER INFORMATION: OH1 (HuVH1C)

<400> SEQUENCE: 87
saggtccagc tggtrcagtc tgg                                              23

<210> SEQ ID NO 88
<211> LENGTH: 23
<212> TYPE: DNA
<213> ORGANISM: Artificial
<220> FEATURE:

<223> OTHER INFORMATION: OH2 (HuVH2B)

<400> SEQUENCE: 88
cagrtcacct tgaaggagtc tgg                                               23

<210> SEQ ID NO 89
<211> LENGTH: 18
<212> TYPE: DNA
<213> ORGANISM: Artificial
<220> FEATURE:
<223> OTHER INFORMATION: OH3 (HuVH3A)

<400> SEQUENCE: 89
gaggtgcagc tggtggag                                                     18

<210> SEQ ID NO 90
<211> LENGTH: 23
<212> TYPE: DNA
<213> ORGANISM: Artificial
<220> FEATURE:
<223> OTHER INFORMATION: OH4 (HuVH3C)

<400> SEQUENCE: 90
gaggtgcagc tggtggagwc ygg                                               23

<210> SEQ ID NO 91
<211> LENGTH: 23
<212> TYPE: DNA
<213> ORGANISM: Artificial
<220> FEATURE:
<223> OTHER INFORMATION: OH5 (HuVH4B)

<400> SEQUENCE: 91
caggtgcagc tacagcagtg ggg                                               23

<210> SEQ ID NO 92
<211> LENGTH: 23
<212> TYPE: DNA
<213> ORGANISM: Artificial
<220> FEATURE:
<223> OTHER INFORMATION: OH6 (HuVH4C)

<400> SEQUENCE: 92
cagstgcagc tgcaggagtc sgg                                               23

<210> SEQ ID NO 93
<211> LENGTH: 23
<212> TYPE: DNA
<213> ORGANISM: Artificial
<220> FEATURE:
<223> OTHER INFORMATION: OH7 (HuVH6A)

<400> SEQUENCE: 93
caggtacagc tgcagcagtc agg                                               23

<210> SEQ ID NO 94
<211> LENGTH: 24
<212> TYPE: DNA
<213> ORGANISM: Artificial
<220> FEATURE:
<223> OTHER INFORMATION: OCM (HuCIgM)

<400> SEQUENCE: 94
tggaagaggc acgttctttt cttt                                              24

<210> SEQ ID NO 95
<211> LENGTH: 41
<212> TYPE: DNA
<213> ORGANISM: Artificial
<220> FEATURE:
<223> OTHER INFORMATION: OK1S (HuVK1B-SAL)

<400> SEQUENCE: 95
tgagcacaca ggtcgacgga catccagwtg acccagtctc c        41

<210> SEQ ID NO 96
<211> LENGTH: 41
<212> TYPE: DNA
<213> ORGANISM: Artificial
<220> FEATURE:
<223> OTHER INFORMATION: OK2S (HuVK2-SAL)

<400> SEQUENCE: 96
tgagcacaca ggtcgacgga tgttgtgatg actcagtctc c        41

<210> SEQ ID NO 97
<211> LENGTH: 41
<212> TYPE: DNA
<213> ORGANISM: Artificial
<220> FEATURE:
<223> OTHER INFORMATION: OK3S (HuVK2B2-SAL)

<400> SEQUENCE: 97
tgagcacaca ggtcgacgga tattgtgatg acccagactc c        41

<210> SEQ ID NO 98
<211> LENGTH: 41
<212> TYPE: DNA
<213> ORGANISM: Artificial
<220> FEATURE:
<223> OTHER INFORMATION: OK4S (HuVK3B-SAL)

<400> SEQUENCE: 98
tgagcacaca ggtcgacgga aattgtgwtg acrcagtctc c        41

<210> SEQ ID NO 99
<211> LENGTH: 41
<212> TYPE: DNA
<213> ORGANISM: Artificial
<220> FEATURE:
<223> OTHER INFORMATION: OK5S (HuVK5-SAL)

<400> SEQUENCE: 99
tgagcacaca ggtcgacgga aacgacactc acgcagtctc c        41

<210> SEQ ID NO 100
<211> LENGTH: 41
<212> TYPE: DNA
<213> ORGANISM: Artificial
<220> FEATURE:
<223> OTHER INFORMATION: OK6S (HuVK6-SAL)

<400> SEQUENCE: 100
tgagcacaca ggtcgacgga aattgtgctg actcagtctc c        41

<210> SEQ ID NO 101
<211> LENGTH: 48
<212> TYPE: DNA
<213> ORGANISM: Artificial
<220> FEATURE:
<223> OTHER INFORMATION: OJK1 (HuJK1-NOT)

<400> SEQUENCE: 101
gagtcattct cgacttgcgg ccgcacgttt gatttccacc ttggtccc            48

<210> SEQ ID NO 102
<211> LENGTH: 48
<212> TYPE: DNA
<213> ORGANISM: Artificial
<220> FEATURE:
<223> OTHER INFORMATION: OJK2 (HuJK2-NOT)

<400> SEQUENCE: 102
gagtcattct cgacttgcgg ccgcacgttt gatctccagc ttggtccc            48

<210> SEQ ID NO 103
<211> LENGTH: 48
<212> TYPE: DNA
<213> ORGANISM: Artificial
<220> FEATURE:
<223> OTHER INFORMATION: OJK3 (HuJK3-NOT)

<400> SEQUENCE: 103
gagtcattct cgacttgcgg ccgcacgttt gatatccact ttggtccc            48

<210> SEQ ID NO 104
<211> LENGTH: 48
<212> TYPE: DNA
<213> ORGANISM: Artificial
<220> FEATURE:
<223> OTHER INFORMATION: OJK4 (HuJK4-NOT)

<400> SEQUENCE: 104
gagtcattct cgacttgcgg ccgcacgttt gatctccacc ttggtccc            48

<210> SEQ ID NO 105
<211> LENGTH: 48
<212> TYPE: DNA
<213> ORGANISM: Artificial
<220> FEATURE:
<223> OTHER INFORMATION: OJK5 (HuJK5-NOT)

<400> SEQUENCE: 105
gagtcattct cgacttgcgg ccgcacgttt aatctccagt cgtgtccc            48

<210> SEQ ID NO 106
<211> LENGTH: 41
<212> TYPE: DNA
<213> ORGANISM: Artificial
<220> FEATURE:
<223> OTHER INFORMATION: OL1S (HuVL1A-SAL)

<400> SEQUENCE: 106
tgagcacaca ggtcgacgca gtctgtgctg actcagccac c            41

<210> SEQ ID NO 107
<211> LENGTH: 41
<212> TYPE: DNA
<213> ORGANISM: Artificial
<220> FEATURE:
<223> OTHER INFORMATION: OL1S (HuVL1B-SAL)

<400> SEQUENCE: 107
tgagcacaca ggtcgacgca gtctgtgytg acgcagccgc c            41

<210> SEQ ID NO 108
<211> LENGTH: 41

```
<212> TYPE: DNA
<213> ORGANISM: Artificial
<220> FEATURE:
<223> OTHER INFORMATION: OL1S (HuVL1C-SAL)

<400> SEQUENCE: 108
tgagcacaca ggtcgacgca gtctgtcgtg acgcagccgc c          41

<210> SEQ ID NO 109
<211> LENGTH: 38
<212> TYPE: DNA
<213> ORGANISM: Artificial
<220> FEATURE:
<223> OTHER INFORMATION: OL2S (HuVL2B-SAL)

<400> SEQUENCE: 109
tgagcacaca ggtcgacgca gtctgccctg actcagcc              38

<210> SEQ ID NO 110
<211> LENGTH: 41
<212> TYPE: DNA
<213> ORGANISM: Artificial
<220> FEATURE:
<223> OTHER INFORMATION: OL3S (HuVL3A-SAL)

<400> SEQUENCE: 110
tgagcacaca ggtcgacgtc ctatgwgctg actcagccac c          41

<210> SEQ ID NO 111
<211> LENGTH: 41
<212> TYPE: DNA
<213> ORGANISM: Artificial
<220> FEATURE:
<223> OTHER INFORMATION: OL4S (HuVL3B-SAL)

<400> SEQUENCE: 111
tgagcacaca ggtcgacgtc ttctgagctg actcaggacc c          41

<210> SEQ ID NO 112
<211> LENGTH: 38
<212> TYPE: DNA
<213> ORGANISM: Artificial
<220> FEATURE:
<223> OTHER INFORMATION: OL5S (HuVL4B-SAL)

<400> SEQUENCE: 112
tgagcacaca ggtcgacgca gcytgtgctg actcaatc              38

<210> SEQ ID NO 113
<211> LENGTH: 41
<212> TYPE: DNA
<213> ORGANISM: Artificial
<220> FEATURE:
<223> OTHER INFORMATION: OL6S (HuVL5-SAL)

<400> SEQUENCE: 113
tgagcacaca ggtcgacgca ggctgtgctg actcagccgt c          41

<210> SEQ ID NO 114
<211> LENGTH: 41
<212> TYPE: DNA
<213> ORGANISM: Artificial
<220> FEATURE:
<223> OTHER INFORMATION: OL7S (HuVL6-SAL)

<400> SEQUENCE: 114
```
tgagcacaca ggtcgacgaa ttttatgctg actcagcccc a                41

<210> SEQ ID NO 115
<211> LENGTH: 41
<212> TYPE: DNA
<213> ORGANISM: Artificial
<220> FEATURE:
<223> OTHER INFORMATION: OL8S (HuVL7/8-SAL)

<400> SEQUENCE: 115
tgagcacaca ggtcgacgca grctgtggtg acycaggagc c                41

<210> SEQ ID NO 116
<211> LENGTH: 41
<212> TYPE: DNA
<213> ORGANISM: Artificial
<220> FEATURE:
<223> OTHER INFORMATION: OL9S (HuVL9-SAL)

<400> SEQUENCE: 116
tgagcacaca ggtcgacgcw gcctgtgctg actcagccmc c                41

<210> SEQ ID NO 117
<211> LENGTH: 36
<212> TYPE: DNA
<213> ORGANISM: Artificial
<220> FEATURE:
<223> OTHER INFORMATION: OL9S (HuVL10-SAL)

<400> SEQUENCE: 117
tgagcacaca ggtcgacgca ggcagggctg actcag                36

<210> SEQ ID NO 118
<211> LENGTH: 48
<212> TYPE: DNA
<213> ORGANISM: Artificial
<220> FEATURE:
<223> OTHER INFORMATION: OJL1 (HuJL1-NOT)

<400> SEQUENCE: 118
gagtcattct cgacttgcgg ccgcacctag gacggtgacc ttggtccc                48

<210> SEQ ID NO 119
<211> LENGTH: 48
<212> TYPE: DNA
<213> ORGANISM: Artificial
<220> FEATURE:
<223> OTHER INFORMATION: OJL2 (HuJL2/3-NOT)

<400> SEQUENCE: 119
gagtcattct cgacttgcgg ccgcacctag gacggtcagc ttggtccc                48

<210> SEQ ID NO 120
<211> LENGTH: 48
<212> TYPE: DNA
<213> ORGANISM: Artificial
<220> FEATURE:
<223> OTHER INFORMATION: OJL3 (HuJL7-NOT)

<400> SEQUENCE: 120
gagtcattct cgacttgcgg ccgcaccgag gacggtcagc tgggtgcc                48

<210> SEQ ID NO 121
<211> LENGTH: 56
<212> TYPE: DNA
<213> ORGANISM: Artificial

```
<220> FEATURE:
<223> OTHER INFORMATION: OH1S (HuVH1B-SFI)

<400> SEQUENCE: 121
gtcctcgcaa ctgcggccca gccggccatg gcccagrtgc agctggtgca rtctgg        56

<210> SEQ ID NO 122
<211> LENGTH: 56
<212> TYPE: DNA
<213> ORGANISM: Artificial
<220> FEATURE:
<223> OTHER INFORMATION: OH1S (HuVH1C-SFI)

<400> SEQUENCE: 122
gtcctcgcaa ctgcggccca gccggccatg gccsaggtcc agctggtrca gtctgg        56

<210> SEQ ID NO 123
<211> LENGTH: 56
<212> TYPE: DNA
<213> ORGANISM: Artificial
<220> FEATURE:
<223> OTHER INFORMATION: OH2S (HuVH2B-SFI)

<400> SEQUENCE: 123
gtcctcgcaa ctgcggccca gccggccatg gcccagrtca ccttgaagga gtctgg        56

<210> SEQ ID NO 124
<211> LENGTH: 51
<212> TYPE: DNA
<213> ORGANISM: Artificial
<220> FEATURE:
<223> OTHER INFORMATION: OH3S (HuVH3A-SFI)

<400> SEQUENCE: 124
gtcctcgcaa ctgcggccca gccggccatg gccgaggtgc agctggtgga g             51

<210> SEQ ID NO 125
<211> LENGTH: 56
<212> TYPE: DNA
<213> ORGANISM: Artificial
<220> FEATURE:
<223> OTHER INFORMATION: OH4S (HuVH3C-SFI)

<400> SEQUENCE: 125
gtcctcgcaa ctgcggccca gccggccatg gccgaggtgc agctggtgga gwcygg        56

<210> SEQ ID NO 126
<211> LENGTH: 56
<212> TYPE: DNA
<213> ORGANISM: Artificial
<220> FEATURE:
<223> OTHER INFORMATION: OH5S (HuVH4B-SFI)

<400> SEQUENCE: 126
gtcctcgcaa ctgcggccca gccggccatg gcccaggtgc agctacagca gtgggg        56

<210> SEQ ID NO 127
<211> LENGTH: 56
<212> TYPE: DNA
<213> ORGANISM: Artificial
<220> FEATURE:
<223> OTHER INFORMATION: OH6S (HuVH4C-SFI)

<400> SEQUENCE: 127
gtcctcgcaa ctgcggccca gccggccatg gcccagstgc agctgcagga gtcsgg        56
```

```
<210> SEQ ID NO 128
<211> LENGTH: 56
<212> TYPE: DNA
<213> ORGANISM: Artificial
<220> FEATURE:
<223> OTHER INFORMATION: OH7S (HuVH6A-SFI)

<400> SEQUENCE: 128
gtcctcgcaa ctgcggccca gccggccatg gcccaggtac agctgcagca gtcagg      56

<210> SEQ ID NO 129
<211> LENGTH: 36
<212> TYPE: DNA
<213> ORGANISM: Artificial
<220> FEATURE:
<223> OTHER INFORMATION: OJH1 (HuJH1/2-XHO)

<400> SEQUENCE: 129
gagtcattct cgactcgaga crgtgaccag ggtgcc                              36

<210> SEQ ID NO 130
<211> LENGTH: 36
<212> TYPE: DNA
<213> ORGANISM: Artificial
<220> FEATURE:
<223> OTHER INFORMATION: OJH2 (HuJH3-XHO)

<400> SEQUENCE: 130
gagtcattct cgactcgaga cggtgaccat tgtccc                              36

<210> SEQ ID NO 131
<211> LENGTH: 36
<212> TYPE: DNA
<213> ORGANISM: Artificial
<220> FEATURE:
<223> OTHER INFORMATION: OJH3 (HuJH4/5-XHO)

<400> SEQUENCE: 131
gagtcattct cgactcgaga cggtgaccag ggttcc                              36

<210> SEQ ID NO 132
<211> LENGTH: 36
<212> TYPE: DNA
<213> ORGANISM: Artificial
<220> FEATURE:
<223> OTHER INFORMATION: OJH4 (HuJH6-XHO)

<400> SEQUENCE: 132
gagtcattct cgactcgaga cggtgaccgt ggtccc                              36

<210> SEQ ID NO 133
<211> LENGTH: 8
<212> TYPE: PRT
<213> ORGANISM: Artificial
<220> FEATURE:
<223> OTHER INFORMATION: HC CDR1

<400> SEQUENCE: 133

Gly Gly Thr Ser Asn Asn Phe Gly
1               5

<210> SEQ ID NO 134
<211> LENGTH: 8
<212> TYPE: PRT
<213> ORGANISM: Artificial
<220> FEATURE:
```

<223> OTHER INFORMATION: HC CDR2

<400> SEQUENCE: 134

Ile Ser Pro Ile Phe Gly Ser Thr
1               5

<210> SEQ ID NO 135
<211> LENGTH: 14
<212> TYPE: PRT
<213> ORGANISM: Artificial
<220> FEATURE:
<223> OTHER INFORMATION: HC CDR3

<400> SEQUENCE: 135

Ala Arg His Gly Asn Tyr Tyr Phe Tyr Ser Gly Met Asp Leu
1               5                   10

<210> SEQ ID NO 136
<211> LENGTH: 6
<212> TYPE: PRT
<213> ORGANISM: Artificial
<220> FEATURE:
<223> OTHER INFORMATION: LC CDR1

<400> SEQUENCE: 136

Asn Val Gly Ser Asn Ser
1               5

<210> SEQ ID NO 137
<211> LENGTH: 3
<212> TYPE: PRT
<213> ORGANISM: Artificial
<220> FEATURE:
<223> OTHER INFORMATION: LC CDR2

<400> SEQUENCE: 137

Asp Asp Arg
1

<210> SEQ ID NO 138
<211> LENGTH: 11
<212> TYPE: PRT
<213> ORGANISM: Artificial
<220> FEATURE:
<223> OTHER INFORMATION: LC CDR3

<400> SEQUENCE: 138

Gln Val Trp Asp Ser Ser Ser Asp His Arg Val
1               5                   10

<210> SEQ ID NO 139
<211> LENGTH: 8
<212> TYPE: PRT
<213> ORGANISM: Artificial
<220> FEATURE:
<223> OTHER INFORMATION: HC CDR1

<400> SEQUENCE: 139

Gly Gly Thr Ser Asn Asn Tyr Ala
1               5

<210> SEQ ID NO 140
<211> LENGTH: 8
<212> TYPE: PRT
<213> ORGANISM: Artificial
<220> FEATURE:
<223> OTHER INFORMATION: HC CDR2

<400> SEQUENCE: 140

Val Ser Pro Ile Phe Gly Ser Thr
1               5

<210> SEQ ID NO 141
<211> LENGTH: 14
<212> TYPE: PRT
<213> ORGANISM: Artificial
<220> FEATURE:
<223> OTHER INFORMATION: HC CDR3

<400> SEQUENCE: 141

Ala Arg His Gly Asn Tyr Tyr Tyr Asn Ser Gly Met Asp Val
1               5                   10

<210> SEQ ID NO 142
<211> LENGTH: 8
<212> TYPE: PRT
<213> ORGANISM: Artificial
<220> FEATURE:
<223> OTHER INFORMATION: LC CDR1

<400> SEQUENCE: 142

Asp Ser Asn Ile Gly Arg Arg Ser
1               5

<210> SEQ ID NO 143
<211> LENGTH: 3
<212> TYPE: PRT
<213> ORGANISM: Artificial
<220> FEATURE:
<223> OTHER INFORMATION: LC CDR2

<400> SEQUENCE: 143

Ser Asn Asp
1

<210> SEQ ID NO 144
<211> LENGTH: 11
<212> TYPE: PRT
<213> ORGANISM: Artificial
<220> FEATURE:
<223> OTHER INFORMATION: LC CDR3

<400> SEQUENCE: 144

Ala Ala Trp Asp Asp Ser Leu Lys Gly Ala Val
1               5                   10

<210> SEQ ID NO 145
<211> LENGTH: 14
<212> TYPE: PRT
<213> ORGANISM: Artificial
<220> FEATURE:
<223> OTHER INFORMATION: HC CDR3

<400> SEQUENCE: 145

Ala Arg His Gly Asn Tyr Tyr Tyr Ser Gly Met Asp Leu
1               5                   10

<210> SEQ ID NO 146
<211> LENGTH: 9
<212> TYPE: PRT
<213> ORGANISM: Artificial
<220> FEATURE:
<223> OTHER INFORMATION: LC CDR1

```
<400> SEQUENCE: 146

Ser Ser Asp Val Gly Gly Tyr Asn Tyr
1               5

<210> SEQ ID NO 147
<211> LENGTH: 10
<212> TYPE: PRT
<213> ORGANISM: Artificial
<220> FEATURE:
<223> OTHER INFORMATION: LC CDR3

<400> SEQUENCE: 147

Cys Ser Tyr Ala Gly Ser Ala Lys Gly Val
1               5                   10

<210> SEQ ID NO 148
<211> LENGTH: 6
<212> TYPE: PRT
<213> ORGANISM: Artificial
<220> FEATURE:
<223> OTHER INFORMATION: LC CDR1

<400> SEQUENCE: 148

Asn Ile Gly Ser Lys Thr
1               5

<210> SEQ ID NO 149
<211> LENGTH: 3
<212> TYPE: PRT
<213> ORGANISM: Artificial
<220> FEATURE:
<223> OTHER INFORMATION: LC CDR2

<400> SEQUENCE: 149

Gly Asp Ser
1

<210> SEQ ID NO 150
<211> LENGTH: 13
<212> TYPE: PRT
<213> ORGANISM: Artificial
<220> FEATURE:
<223> OTHER INFORMATION: LC CDR3

<400> SEQUENCE: 150

Gln Val Trp Asp Ser Ser Ser Asp His Pro Gly Ala Val
1               5                   10

<210> SEQ ID NO 151
<211> LENGTH: 8
<212> TYPE: PRT
<213> ORGANISM: Artificial
<220> FEATURE:
<223> OTHER INFORMATION: HC CDR2

<400> SEQUENCE: 151

Ile Ser Pro Ile Phe Gly Ser Ala
1               5

<210> SEQ ID NO 152
<211> LENGTH: 14
<212> TYPE: PRT
<213> ORGANISM: Artificial
<220> FEATURE:
<223> OTHER INFORMATION: HC CDR3

<400> SEQUENCE: 152
```

```
Ala Arg His Gly Asn Tyr Tyr Tyr Ser Gly Met Asp Val
1               5                   10
```

<210> SEQ ID NO 153
<211> LENGTH: 8
<212> TYPE: PRT
<213> ORGANISM: Artificial
<220> FEATURE:
<223> OTHER INFORMATION: LC CDR1

<400> SEQUENCE: 153

```
Ser Ser Asn Ile Gly Ser Asn Thr
1               5
```

<210> SEQ ID NO 154
<211> LENGTH: 3
<212> TYPE: PRT
<213> ORGANISM: Artificial
<220> FEATURE:
<223> OTHER INFORMATION: LC CDR2

<400> SEQUENCE: 154

```
Gly Asp Asp
1
```

<210> SEQ ID NO 155
<211> LENGTH: 11
<212> TYPE: PRT
<213> ORGANISM: Artificial
<220> FEATURE:
<223> OTHER INFORMATION: LC CDR3

<400> SEQUENCE: 155

```
Ala Thr Trp Asp Asp Ser Leu Asn Gly His Val
1               5                   10
```

<210> SEQ ID NO 156
<211> LENGTH: 6
<212> TYPE: PRT
<213> ORGANISM: Artificial
<220> FEATURE:
<223> OTHER INFORMATION: LC CDR1

<400> SEQUENCE: 156

```
Gln His Ile Ser Ser Trp
1               5
```

<210> SEQ ID NO 157
<211> LENGTH: 3
<212> TYPE: PRT
<213> ORGANISM: Artificial
<220> FEATURE:
<223> OTHER INFORMATION: LC CDR2

<400> SEQUENCE: 157

```
Ser Ala Ser
1
```

<210> SEQ ID NO 158
<211> LENGTH: 9
<212> TYPE: PRT
<213> ORGANISM: Artificial
<220> FEATURE:
<223> OTHER INFORMATION: LC CDR3

<400> SEQUENCE: 158

```
Gln Gln Ala Asn Ser Phe Pro Leu Thr
1               5

<210> SEQ ID NO 159
<211> LENGTH: 3
<212> TYPE: PRT
<213> ORGANISM: Artificial
<220> FEATURE:
<223> OTHER INFORMATION: LC CDR2

<400> SEQUENCE: 159

Val Asp Ser
1

<210> SEQ ID NO 160
<211> LENGTH: 13
<212> TYPE: PRT
<213> ORGANISM: Artificial
<220> FEATURE:
<223> OTHER INFORMATION: LC CDR3

<400> SEQUENCE: 160

Gln Val Trp Asp Ser Asn Ser Asp His Pro Gly Ala Val
1               5                   10

<210> SEQ ID NO 161
<211> LENGTH: 14
<212> TYPE: PRT
<213> ORGANISM: Artificial
<220> FEATURE:
<223> OTHER INFORMATION: HC CDR3

<400> SEQUENCE: 161

Ala Arg His Gly Asn Tyr Tyr Tyr Tyr Ser Gly Thr Asp Val
1               5                   10

<210> SEQ ID NO 162
<211> LENGTH: 14
<212> TYPE: PRT
<213> ORGANISM: Artificial
<220> FEATURE:
<223> OTHER INFORMATION: HC CDR3

<400> SEQUENCE: 162

Ala Arg His Gly Thr Tyr Tyr Tyr Tyr Ser Gly Met Asp Val
1               5                   10

<210> SEQ ID NO 163
<211> LENGTH: 9
<212> TYPE: PRT
<213> ORGANISM: Artificial
<220> FEATURE:
<223> OTHER INFORMATION: LC CDR1

<400> SEQUENCE: 163

Ser Ser Asn Ile Gly Ala Gly Tyr Asp
1               5

<210> SEQ ID NO 164
<211> LENGTH: 3
<212> TYPE: PRT
<213> ORGANISM: Artificial
<220> FEATURE:
<223> OTHER INFORMATION: LC CDR2

<400> SEQUENCE: 164

Gly Asn Asn
```

-continued

```
<210> SEQ ID NO 165
<211> LENGTH: 11
<212> TYPE: PRT
<213> ORGANISM: Artificial
<220> FEATURE:
<223> OTHER INFORMATION: LC CDR3

<400> SEQUENCE: 165

Gln Ser Tyr Asp Gln Asn Leu Ser Glu Gly Val
1               5                   10

<210> SEQ ID NO 166
<211> LENGTH: 6
<212> TYPE: PRT
<213> ORGANISM: Artificial
<220> FEATURE:
<223> OTHER INFORMATION: LC CDR1

<400> SEQUENCE: 166

Gln Ser Val Ser Ser Tyr
1               5

<210> SEQ ID NO 167
<211> LENGTH: 3
<212> TYPE: PRT
<213> ORGANISM: Artificial
<220> FEATURE:
<223> OTHER INFORMATION: LC CDR2

<400> SEQUENCE: 167

Gly Ala Ser
1

<210> SEQ ID NO 168
<211> LENGTH: 9
<212> TYPE: PRT
<213> ORGANISM: Artificial
<220> FEATURE:
<223> OTHER INFORMATION: LC CDR3

<400> SEQUENCE: 168

Gln Gln Tyr Gly Ser Ser Pro Phe Ala
1               5

<210> SEQ ID NO 169
<211> LENGTH: 6
<212> TYPE: PRT
<213> ORGANISM: Artificial
<220> FEATURE:
<223> OTHER INFORMATION: LC CDR1

<400> SEQUENCE: 169

Asn Ile Gly Ser Lys Ser
1               5

<210> SEQ ID NO 170
<211> LENGTH: 13
<212> TYPE: PRT
<213> ORGANISM: Artificial
<220> FEATURE:
<223> OTHER INFORMATION: LC CDR3

<400> SEQUENCE: 170

Gln Ser Tyr Asp Ser Gly Leu Ser Ala Ser Pro Tyr Val
1               5                   10
```

<210> SEQ ID NO 171
<211> LENGTH: 9
<212> TYPE: PRT
<213> ORGANISM: Artificial
<220> FEATURE:
<223> OTHER INFORMATION: LC CDR1

<400> SEQUENCE: 171

Ser Ala Asn Ile Gly Ala Gly Tyr Asp
1               5

<210> SEQ ID NO 172
<211> LENGTH: 11
<212> TYPE: PRT
<213> ORGANISM: Artificial
<220> FEATURE:
<223> OTHER INFORMATION: LC CDR3

<400> SEQUENCE: 172

Gln Ser Tyr Asp Ser Ser Leu Ser Gly Ala Leu
1               5                   10

<210> SEQ ID NO 173
<211> LENGTH: 11
<212> TYPE: PRT
<213> ORGANISM: Artificial
<220> FEATURE:
<223> OTHER INFORMATION: LC CDR3

<400> SEQUENCE: 173

Ala Ala Trp Asp Ala Ser Leu Ser Gly Pro Val
1               5                   10

<210> SEQ ID NO 174
<211> LENGTH: 3
<212> TYPE: PRT
<213> ORGANISM: Artificial
<220> FEATURE:
<223> OTHER INFORMATION: LC CDR2

<400> SEQUENCE: 174

Asp Val Ser
1

<210> SEQ ID NO 175
<211> LENGTH: 10515
<212> TYPE: DNA
<213> ORGANISM: Artificial
<220> FEATURE:
<223> OTHER INFORMATION: Vector pIg-C911-HCgamma1

<400> SEQUENCE: 175
tcgacggatc gggagatctc ccgatcccct atggtgcact ctcagtacaa tctgctctga      60
tgccgcatag ttaagccagt atctgctccc tgcttgtgtg ttggaggtcg ctgagtagtg     120
cgcgagcaaa atttaagcta acaaggca aggcttgacc gacaattgca tgaagaatct      180
gcttagggtt aggcgttttg cgctgcttcg ctaggtggtc aatattggcc attagccata     240
ttattcattg gttatatagc ataaatcaat attggctatt ggccattgca tacgttgtat     300
ccatatcata atatgtacat ttatattggc tcatgtccaa cattaccgcc atgttgacat     360
tgattattga ctagttatta atagtaatca attacgggt cattagttca tagcccatat      420
atggagttcc gcgttacata acttacggta aatggcccgc ctggctgacc gcccaacgac     480

```
ccccgcccat tgacgtcaat aatgacgtat gttcccatag taacgccaat agggactttc    540
cattgacgtc aatgggtgga gtatttacgg taaactgccc acttggcagt acatcaagtg    600
tatcatatgc caagtacgcc ccctattgac gtcaatgacg gtaaatggcc cgcctggcat    660
tatgcccagt acatgacctt atgggacttt cctacttggc agtacatcta cgtattagtc    720
atcgctatta ccatggtgat gcggttttgg cagtacatca atgggcgtgg atagcggttt    780
gactcacggg gatttccaag tctccacccc attgacgtca atgggagttt gttttggcac    840
caaaatcaac gggactttcc aaaatgtcgt aacaactccg ccccattgac gcaaatgggc    900
ggtaggcgtg tacggtggga ggtctatata agcagagctc gtttagtgaa ccgtcagatc    960
gcctggagac gccatccacg ctgttttgac ctccatagaa gacaccggga ccgatccagc   1020
ctccgcggcc gggaacggtg cattggaagc tgcctggat atcctgactc tcttaggtag    1080
ccttgcagaa gttggtcgtg aggcactggg caggtaagta tcaaggttac aagacaggtt   1140
taaggagatc aatagaaact gggcttgtcg agacagagaa gactcttgcg tttctgatag   1200
gcacctattg gtcttactga catccacttt gcctttctct ccacaggtgt ccactcccag   1260
ttcaattaca gctcgccacc atgggatgga gctgtatcat cctcttcttg gtactgctgc   1320
tggcccagcc ggccagtgac cttgaccggt gcaccacttt tgatgatgtt caagctccta   1380
attacactca acatacttca tctatgaggg gggtttacta tcctgatgaa attttagat    1440 cggacactct ttatttaact caggattat ttcttccatt ttattctaat gttacagggt    1500
ttcatactat taatcatacg tttggcaacc ctgtcatacc ttttaaggat ggtatttatt   1560
ttgctgccac agagaaatca aatgttgtcc gtggttgggt ttttggttct accatgaaca   1620
acaagtcaca gtcggtgatt attattaaca attctactaa tgttgttata cgagcatgta   1680
actttgaatt gtgtgacaac ccttttcttg ctgtttctaa acccatgggt acacagacac   1740
atactatgat attcgataat gcatttaatt gcactttcga gtacatatct gatgcctttt   1800
cgcttgatgt ttcagaaaag tcaggtaatt ttaaacactt acgagagttt gtgtttaaaa   1860
ataaagatgg gtttctctat gtttataagg ctatcaacc tatagatgta gttcgtgatc    1920
taccttctgg ttttaacact ttgaaaccta ttttaagtt gcctcttggt attaacatta    1980
caaattttag agccattctt acagcctttt cacctgctca agacatttgg ggcacgtcag   2040
ctgcagccta ttttgttggc tatttaaagc caactacatt tatgctcaag tatgatgaaa   2100
atggtacaat cacagatgct gttgattgtt ctcaaaatcc acttgctgaa ctcaaatgct   2160
ctgttaagag ctttgagatt gacaaaggaa tttaccagac ctctaatttc agggttgttc   2220
cctcaggaga tgttgtgaga ttccctaata ttacaaactt gtgtccttt ggagaggttt    2280 ttaatgctac taaattccct tctgtctatg catgggagaa aaaaaaaatt tctaattgtg   2340
ttgctgatta ctctgtgctc tacaactcaa cattttttc aacctttaag tgctatggcg   2400
tttctgccac taagttgaat gatctttgct ctccaatgt ctatgcagat tcttttgtag    2460
tcaagggaga tgatgtaaga caaatagcgc aggacaaac tggtgttatt gctgattata   2520
attataaatt gccagatgat ttcatgggtt gtgtccttgc ttggaatact aggaacattg   2580
atgctacttc aactggtaat tataattata aatataggta tcttagacat ggcaagctta   2640 ggcccttga gagagacata tctaatgtgc ctttctcccc tgatggcaaa ccttgcaccc    2700
cacctgctct taattgttat tggccattaa atgattatgg ttttttacac actactggca   2760
ttggctacca accttacaga gttgtagtac tttcttttga acttttaaat gcaccggcca   2820
cggtttgtgg accaaaaatta tccactgacc ttattaagaa ccagtgtgtc aatttttaatt  2880
```

```
ttaatggact cactggtact ggtgtgttaa ctccttcttc aaagagattt caaccatttc    2940
aacaatttgg ccgtgatgtt tctgatttca ctgattccgt tcgagatcct aaaacatctg    3000
aaatattaga catttcacct tgctcttttg ggggtgtaag tgtaattaca cctggaacaa    3060
atgcttcatc tgaagttgct gttctatatc aagatgttaa ctgcactgat gtttctacag    3120
caattcatgc agatcaactc acaccagctt ggcgcatata ttctactgga aacaatgtat    3180
tccagactca ggcaggctgt cttataggag ctgagcatgt cgacacttct tatgagtgcg    3240
acattcctat tggagctggc atttgtgcta gttaccatac agtttcttta ttacgtagta    3300
ctagccaaaa atctattgtg gcttatacta tgtctttagg tgctgatagt tcaattgctt    3360
actctaataa caccattgct atacctacta acttttcaat tagcattact acagaagtaa    3420
tgcctgtttc tatggctaaa acctccgtag attgtaatat gtacatctgc ggagattcta    3480
ctgaatgtgc taatttgctt ctccaatatg gtagcttttg cacacaacta aatcgtgcac    3540
tctcaggtat tgctgctgaa caggatcgca acacacgtga agtgttcgct caagtcaaac    3600
aaatgtacaa accccaact ttgaaatatt ttggtggttt taattttca caaatattac    3660 ctgaccctct aaagccaact aagaggtctt ttattgagga cttgctcttt aataaggtga    3720
cactcgctga tgctggcttc atgaagcaat atggcgaatg cctaggtgat attaatgcta    3780
gagatctcat ttgtgcgcag aagttcaatg gacttacagt gttgccacct ctgctcactg    3840
atgatatgat tgctgcctac actgctgctc tagttagtgg tactgccact gctggatgga    3900
catttggtgc tggcgctgct cttcaaatac cttttgctat gcaaatggca tataggttca    3960
atggcattgg agttacccaa aatgttctct atgagaacca aaaacaaatc gccaaccaat    4020
ttaacaaggc gattagtcaa attcaagaat cacttacaac aacatcaact gcattgggca    4080
agctgcaaga cgttgttaac cagaatgctc aagcattaaa cacacttgtt aaacaactta    4140
gctctaattt tggtgcaatt tcaagtgtgc taaatgatat cctttcgcga cttgataaag    4200
tcgaggcgga ggtacaaatt gacaggttaa ttacaggcag acttcaaagc cttcaaacct    4260
atgtaacaca acaactaatc agggctgctg aaatcagggc ttctgctaat cttgctgcta    4320
ctaaaatgtc tgagtgtgtt cttggacaat caaaaagagt tgacttttgt ggaaagggct    4380
accaccttat gtccttccca caagcagccc cgcatggtgt tgtcttccta catgtcacgt    4440
atgtgccatc ccaggagagg aacttcacca gcgccagc aatttgtcat gaaggcaaag    4500
catacttccc tcgtgaaggt gttttttgtgt taatggcac ttcttggttt attacacaga    4560
ggaacttctt ttctccacaa ataattacta cagacaatac atttgtctca ggaaattgtg    4620
atgtcgttat tggcatcatt aacaacacag tttatgatcc tctgcaacct gagcttgact    4680
cattcaaaga agagctggac aagtacttca aaaatcatac atcaccagat gttgattttg    4740
gcgacatttc aggcattaac gcttctgtcg tcaacattca aaaagaaatt gaccgcctca    4800
atgaggtcgc taaaaattta aatgaatcac tcattgacct tcaagaactg ggaaaatatg    4860
agcaatatat taaatggcct ctcgacgaac aaaaactcat ctcagaagag atctgaatg    4920 ctgtgggcca ggacacgcag gaggtcatcg tggtgccaca ctccttgccc tttaaggtgg    4980
tggtgatctc agccatcctg gccctggtgg tgctcaccat catctccctt atcatcctca    5040
tcatgctttg gcagaagaag ccacgttagg cggccgctcg agtgctagca ccaagggccc    5100
cagcgtgttc cccctggccc ccagcagcaa gagcaccagc ggcggcacag ccgccctggg    5160
ctgcctggtg aaggactact cccccgagcc cgtgaccgtg agctggaaca gcggcgcctt    5220
```

```
gaccagcggc gtgcacacct tccccgccgt gctgcagagc agcggcctgt acagcctgag    5280
cagcgtggtg accgtgccca gcagcagcct gggcacccag acctacatct gcaacgtgaa    5340
ccacaagccc agcaacacca aggtggacaa acgcgtggag cccaagagct gcgacaagac    5400
ccacacctgc ccccctgcc ctgccccga gctgctgggc ggaccctccg tgttcctgtt    5460
ccccccaag cccaaggaca ccctcatgat cagccggacc cccgaggtga cctgcgtggt    5520
ggtggacgtg agccacgagg accccgaggt gaagttcaac tggtacgtgg acggcgtgga    5580
ggtgcacaac gccaagacca gccccgggag gagcagtac aacagcacct accgggtggt    5640
gagcgtgctc accgtgctgc accaggactg gctgaacggc aaggagtaca agtgcaaggt    5700
gagcaacaag gccctgcctg cccccatcga aaagaccatc agcaaggcca agggccagcc    5760
ccgggagccc caggtgtaca ccctgccccc cagccgggag gagatgacca agaaccaggt    5820
gtccctcacc tgtctggtga agggcttcta ccccagcgac atcgccgtgg agtgggagag    5880
caacggccag cccgagaaca actacaagac caccccccct gtgctggaca gcgacggcag    5940
cttcttcctg tacagcaagc tcaccgtgga caagagccgg tggcagcagg gcaacgtgtt    6000
cagctgcagc gtgatgcacg aggccctgca caaccactac acccagaaga gcctgagcct    6060
gagccccggc aagtgataat ctagagggcc cgtttaaacc cgctgatcag cctcgactgt    6120
gccttctagt tgccagccat ctgttgtttg ccctccccc gtgccttcct tgaccctgga    6180
aggtgccact cccactgtcc tttcctaata aatgaggaa attgcatcgc attgtctgag    6240
taggtgtcat tctattctgg ggggtggggt ggggcaggac agcaagggg aggattggga    6300
agacaatagc aggcatgctg gggatgcggt gggctctatg gcttctgagg cggaaagaac    6360
cagctggggc tctaggggt atccccacgc gccctgtagc ggcgcattaa gcgcggcggg    6420
tgtggtggtt acgcgcagcg tgaccgctac acttgccagc gccctagcgc ccgctccttt    6480
cgctttcttc ccttcctttc tcgccacgtt cgccggcttt ccccgtcaag ctctaaatcg    6540
ggggctccct ttagggttcc gatttagtgc tttacggcac ctcgacccca aaaaacttga    6600
ttagggtgat ggttcacgta gtgggccatc gccctgatag acggtttttc gccctttgac    6660
gttggagtcc acgttcttta atagtggact cttgttccaa actggaacaa cactcaaccc    6720
tatctcggtc tattcttttg atttataagg gattttgccg atttcggcct attggttaaa    6780
aaatgagctg atttaacaaa aatttaacgc gaattaattc tgtggaatgt gtgtcagtta    6840
gggtgtggaa agtccccagg ctccccagca ggcagaagta tgcaaagcat gcatctcaat    6900
tagtcagcaa ccaggtgtgg aaagtcccca ggctccccag caggcagaag tatgcaaagc    6960
atgcatctca attagtcagc aaccatagtc ccgcccctaa ctccgcccat cccgcccta    7020
actccgccca gttccgccca ttctccgccc catggctgac taattttttt tatttatgca    7080
gaggccgagg ccgcctctgc ctctgagcta ttccagaagt agtgaggagg cttttttgga    7140
ggcctaggct tttgcaaaaa gctcccggga gcttgtatat ccattttcgg atctgatcaa    7200
gagacaggat gaggatcgtt tcgcatgatt gaacaagatg gattgcacgc aggttctccg    7260
gccgcttggg tggagaggct attcggctat gactgggcac aacagacaat cggctgctct    7320
gatgccgccg tgttccggct gtcagcgcag gggcgcccgg ttcttttgt caagaccgac    7380
ctgtccggtg ccctgaatga actgcaggac gaggcagcgc ggctatcgtg gctggccacg    7440
acgggcgttc cttgcgcagc tgtgctcgac gttgtcactg aagcgggaag ggactggctg    7500
ctattgggcg aagtgccggg gcaggatctc ctgtcatctc accttgctcc tgccgagaaa    7560
gtatccatca tggctgatgc aatgcggcgg ctgcatacgc ttgatccggc tacctgccca    7620
```

```
ttcgaccacc aagcgaaaca tcgcatcgag cgagcacgta ctcggatgga agccggtctt    7680
gtcgatcagg atgatctgga cgaagagcat caggggctcg cgccagccga actgttcgcc    7740
aggctcaagg cgcgcatgcc cgacggcgag gatctcgtcg tgacccatgg cgatgcctgc    7800
ttgccgaata tcatggtgga aaatggccgc ttttctggat tcatcgactg tggccggctg    7860
ggtgtggcgg accgctatca ggacatagcg ttggctaccc gtgatattgc tgaagagctt    7920
ggcggcgaat gggctgaccg cttcctcgtg ctttacggta tcgccgctcc cgattcgcag    7980
cgcatcgcct tctatcgcct tcttgacgag ttcttctgag cgggactctg gggttcgaaa    8040
tgaccgacca agcgacgccc aacctgccat cacgagattt cgattccacc gccgccttct    8100
atgaaaggtt gggcttcgga atcgttttcc gggacgccgg ctggatgatc tccagcgcg    8160
gggatctcat gctggagttc ttcgcccacc ccaacttgtt tattgcagct tataatggtt    8220
acaaataaag caatagcatc acaaatttca caaataaagc attttttca ctgcattcta     8280
gttgtggttt gtccaaactc atcaatgtat cttatcatgt ctgtataccg tcgacctcta    8340
gctagagctt ggcgtaatca tggtcatagc tgtttcctgt gtgaaattgt tatccgctca    8400
caattccaca acatacga gccggaagca taaagtgtaa agcctggggt gcctaatgag      8460
tgagctaact cacattaatt gcgttgcgct cactgcccgc tttccagtcg ggaaacctgt    8520
cgtgccagct gcattaatga atcggccaac gcgcggggag aggcggtttg cgtattgggc    8580
gctcttccgc ttcctcgctc actgactcgc tgcgctcggt cgttcggctg cggcgagcgg    8640
tatcagctca ctcaaaggcg gtaatacggt tatccacaga atcaggggat aacgcaggaa    8700
agaacatgtg agcaaaaggc cagcaaaagg ccaggaaccg taaaaaggcc gcgttgctgg    8760
cgttttccca taggctccgc cccctgacg agcatcacaa aaatcgacgc tcaagtcaga    8820
ggtggcgaaa cccgacagga ctataaagat accaggcgtt tccccctgga agctccctcg    8880
tgcgctctcc tgttccgacc ctgccgctta ccggatacct gtccgccttt ctcccttcgg    8940
gaagcgtggc gctttctcat agctcacgct gtaggtatct cagttcggtg taggtcgttc    9000
gctccaagct gggctgtgtg cacgaacccc ccgttcagcc cgaccgctgc gccttatccg    9060
gtaactatcg tcttgagtcc aacccggtaa gacacgactt atcgccactg gcagcagcca    9120
ctggtaacag gattagcaga gcgaggtatg taggcggtgc tacagagttc ttgaagtggt    9180
ggcctaacta cggctacact agaagaacag tatttggtat ctgcgctctg ctgaagccag    9240
ttaccttcgg aaaaagagtt ggtagctctt gatccggcaa acaaaccacc gctggtagcg    9300
gtttttttgt ttgcaagcag cagattacgc gcagaaaaaa aggatctcaa gaagatcctt    9360
tgatcttttc tacggggtct gacgctcagt ggaacgaaaa ctcacgttaa gggattttgg    9420
tcatgagatt atcaaaaagg atcttcacct agatcctttt aaattaaaaa tgaagtttta    9480
aatcaatcta agtatatatg agtaaacttg gtctgacag ttaccaatgc ttaatcagtg     9540
aggcacctat ctcagcgatc tgtctatttc gttcatccat agttgcctga ctccccgtcg    9600
tgtagataac tacgatacgg gagggcttac catctggccc cagtgctgca atgataccgc    9660
gagacccacg ctcaccggct ccagatttat cagcaataaa ccagccagcc ggaagggccg    9720
agcgcagaag tggtcctgca actttatccg cctccatcca gtctattaat tgttgccggg    9780
aagctagagt aagtagttcg ccagttaata gtttgcgcaa cgttgttgcc attgctacag    9840
gcatcgtggt gtcacgctcg tcgtttggta tggcttcatt cagctccggt tcccaacgat    9900
caaggcgagt tacatgatcc cccatgttgt gcaaaaaagc ggttagctcc ttcggtcctc    9960
```

| | |
|---|---|
| cgatcgttgt cagaagtaag ttggccgcag tgttatcact catggttatg gcagcactgc | 10020 |
| ataattctct tactgtcatg ccatccgtaa gatgcttttc tgtgactggt gagtactcaa | 10080 |
| ccaagtcatt ctgagaatag tgtatgcggc gaccgagttg ctcttgcccg gcgtcaatac | 10140 |
| gggataatac cgcgccacat agcagaactt taaaagtgct catcattgga aaacgttctt | 10200 |
| cggggcgaaa actctcaagg atcttaccgc tgttgagatc cagttcgatg taacccactc | 10260 |
| gtgcacccaa ctgatcttca gcatctttta ctttcaccag cgtttctggg tgagcaaaaa | 10320 |
| caggaaggca aaatgccgca aaaagggaa taagggcgac acggaaatgt tgaatactca | 10380 |
| tactcttcct ttttcaatat tattgaagca tttatcaggg ttattgtctc atgagcggat | 10440 |
| acatatttga atgtatttag aaaaataaac aatagggggt tccgcgcaca tttccccgaa | 10500 |
| aagtgccacc tgacg | 10515 |

<210> SEQ ID NO 176
<211> LENGTH: 8777
<212> TYPE: DNA
<213> ORGANISM: Artificial
<220> FEATURE:
<223> OTHER INFORMATION: Vector pIg-C909-Ckappa

<400> SEQUENCE: 176

| | |
|---|---|
| tcgacggatc gggagatctc ccgatcccct atggtgcact ctcagtacaa tctgctctga | 60 |
| tgccgcatag ttaagccagt atctgctccc tgcttgtgtg ttggaggtcg ctgagtagtg | 120 |
| cgcgagcaaa atttaagcta caacaaggca aggcttgacc gacaattgtt aattaacatg | 180 |
| aagaatctgc ttagggttag gcgttttgcg ctgcttcgct aggtggtcaa tattggccat | 240 |
| tagccatatt attcattggt tatatagcat aaatcaatat ggctattggc cattgcata | 300 |
| cgttgtatcc atatcataat atgtacattt atattggctc atgtccaaca ttaccgccat | 360 |
| gttgacattg attattgact agttattaat agtaatcaat tacgggtca ttagttcata | 420 |
| gcccatatat ggagttccgc gttacataac ttacggtaaa tggcccgcct ggctgaccgc | 480 |
| ccaacgaccc ccgcccattg acgtcaataa tgacgtatgt tcccatagta acgccaatag | 540 |
| ggactttcca ttgacgtcaa tgggtggagt atttacggta aactgcccac ttggcagtac | 600 |
| atcaagtgta tcatatgcca agtacgcccc ctattgacgt caatgacggt aaatggcccg | 660 |
| cctggcatta tgcccagtac atgaccttat gggactttcc tacttggcag tacatctacg | 720 |
| tattagtcat cgctattacc atggtgatgc ggttttggca gtacatcaat gggcgtggat | 780 |
| agcggtttga ctcacgggga tttccaagtc tccaccccat tgacgtcaat gggagtttgt | 840 |
| tttggcacca aaatcaacgg gactttccaa aatgtcgtaa caactccgcc ccattgacgc | 900 |
| aaatgggcgg taggcgtgta cggtgggagg tctatataag cagagctcgt ttagtgaacc | 960 |
| gtcagatcgc ctggagacgc catccacgct gttttgacct ccatagaaga caccgggacc | 1020 |
| gatccagcct ccgcggccgg gaacggtgca ttggaatcga tgactctctt aggtagcctt | 1080 |
| gcagaagttg gtcgtgaggc actgggcagg taagtatcaa ggttacaaga caggtttaag | 1140 |
| gagatcaata gaaactgggc ttgtcgagac agagaagact cttgcgtttc tgataggcac | 1200 |
| ctattggtct tactgacatc cactttgcct ttctctccac aggtgtccac tcccagttca | 1260 |
| attacagctc gccaccatgc ggctgcccgc ccagctgctg ggccttctca tgctgtgggt | 1320 |
| gcccgcctcg agatctatcg atgcatgcca tggtaccaag cttgccacca tgagcagcag | 1380 |
| ctcttggctc tgctgagcc tggtggccgt gacagccgcc cagagcacca tcgaggcagca | 1440 |
| ggccaagacc ttcctggaca agttcaacca cgaggccgag gacctgttct accagagcag | 1500 |

```
cctggccagc tggaactaca acaccaacat caccgaggag aacgtgcaga acatgaacaa    1560
cgccggcgac aagtggagcg ccttcctgaa ggagcagagc acactggccc agatgtaccc    1620
cctgcaggag atccagaacc tgaccgtgaa gctgcagctg caggccctgc agcagaacgg    1680
cagcagcgtg ctgagcgagg acaagagcaa gcggctgaac accatcctga acaccatgtc    1740
caccatctac agcaccggca aagtgtgcaa ccccgacaac ccccaggagt gcctgctgct    1800
ggagcccggc ctgaacgaga tcatggccaa cagcctggac tacaacgagc ggctgtgggc    1860
ctgggagagc tggcggagcg aagtgggcaa gcagctgcgg ccctgtacg aggagtacgt    1920
ggtgctgaag aacgagatgg ccagggccaa ccactacgag gactacgcg actactggag    1980
aggcgactac gaagtgaacg gcgtggacgg ctacgactac agcagaggcc agctgatcga    2040
ggacgtggag cacaccttcg aggagatcaa gcctctgtac gagcacctgc acgcctacgt    2100
gcgggccaag ctgatgaacg cctaccccag ctacatcagc cccatcggct gcctgcccgc    2160
ccacctgctg ggcgacatgt ggggccggtt ctggaccaac ctgtacagcc tgaccgtgcc    2220
cttcggccag aagcccaaca tcgacgtgac cgacgccatg gtggaccagg cctgggacgc    2280
ccagcggatc ttcaaggagg ccgagaagtt cttcgtgagc gtgggcctgc caacatgac    2340
ccagggcttt tgggagaaca gcatgctgac cgaccccggc aatgtgcaga aggccgtgtg    2400
ccaccccacc gcctgggacc tgggcaaggg cgacttccgg atcctgatgt gcaccaaagt    2460
gaccatggac gacttcctga ccgcccacca cgagatgggc cacatccagt acgacatggc    2520
ctacgccgcc cagcccttcc tgctgcggaa cggcgccaac gagggctttc acgaggccgt    2580
gggcgagatc atgagcctga cgccgccac ccccaagcac ctgaagagca tcggcctgct    2640
gagccccgac ttccaggagg acaacgagac cgagatcaac ttcctgctga gcaggccct    2700
gaccatcgtg ggcacccgc ccttcaccta catgctggag aagtggcggt ggatggtgtt    2760
taagggcgag atccccaagg accagtggat gaagaagtgg tgggagatga gcgggagat    2820
cgtgggcgtg gtggagcccg tgccccacga cgagacctac tgcgacccg ccagcctgtt    2880
ccacgtgagc aacgactact ccttcatccg gtactacacc cggaccctgt accagttcca    2940
gttccaggag gccctgtgcc aggccgccaa gcacgagggc cccctgcaca gtgcgacat    3000
cagcaacagc accgaggccg acagaaaact gttcaacatg ctgcggctgg caagagcga    3060
gccctggacc ctggccctgg agaatgtggt gggcgccaag aacatgaatg tgcgcccct    3120
gctgaactac ttcgagcccc tgttcacctg gctgaaggac cagaacaaga cagcttcgt    3180
gggctggagc accgactgga gcccctacgc cgaccagagc atcaaagtgc ggatcagcct    3240
gaagagcgcc ctgggcgaca aggcctacga gtggaacgac aacgagatgt acctgttccg    3300
gagcagcgtg gcctatgcca tgcggcagta cttcctgaaa gtgaagaacc agatgatcct    3360
gttcggcgag gaggacgtga gagtggccaa cctgaagccc cggatcagct tcaacttctt    3420
cgtgaccgcc cccaagaacg tgagcgacat catcccccgg accgaagtgg agaaggccat    3480
ccggatgagc cggagccgga tcaacgacgc cttccggctg aacgacaact ccctggagtt    3540
cctgggcatc cagcccaccc tgggccctcc caaccagccc cccgtgagca tctggctgat    3600
cgtgtttggc gtggtgatgg gcgtgatcgt ggtgggaatc gtgatcctga tcttcaccgg    3660
catccgggac cggaagaaga gaacaaggc ccggagcggc gagaacccct acgccagcat    3720
cgatatcagc aagggcgaga caaccccgg cttccagaac accgacgacg tgcagaccag    3780
cttctgataa tctagaacga gctcgaattc gaagcttctg cagacgcgtc gacgtcatat    3840
```

```
ggatccgata tcgccgtggc ggccgcaccc agcgtgttca tcttcccccc ctccgacgag    3900
cagctgaaga gcggcaccgc cagcgtggtg tgcctgctga caacttcta ccccccgggag    3960 gccaaggtgc agtggaaggt ggacaacgcc ctgcagagcg gcaacagcca ggagagcgtg    4020
accgagcagg acagcaagga ctccacctac agcctgagca gcaccctcac cctgagcaag    4080
gccgactacg agaagcacaa ggtgtacgcc tgcgaggtga cccaccaggg cctgagcagc    4140
cccgtgacca gagcttcaa ccggggcgag tgttaataga cttaagttta aaccgctgat    4200
cagcctcgac tgtgccttct agttgccagc catctgttgt ttgcccctcc cccgtgcctt    4260
ccttgaccct ggaaggtgcc actcccactg tcctttccta ataaaatgag gaaattgcat    4320
cgcattgtct gagtaggtgt cattctattc tggggggtgg ggtggggcag gacagcaagg    4380
gggaggattg ggaagacaat agcaggcatg ctggggatgc ggtgggctct atggcttctg    4440
aggcggaaag aaccagctgg ggctctaggg ggtatcccca cgcgccctgt agcggcgcat    4500
taagcgcggc gggtgtggtg gttacgcgca gcgtgaccgc tacacttgcc agcgccctag    4560
cgcccgctcc tttcgctttc ttcccttcct ttctcgccac gttcgccggc tttccccgtc    4620
aagctctaaa tcggggggctc cctttagggt tccgatttag tgctttacgg cacctcgacc    4680
ccaaaaaact tgattagggt gatggttcac gtagtgggcc atcgccctga tagacggttt    4740
ttcgcccttt gacgttggag tccacgttct ttaatagtgg actcttgttc caaactggaa    4800
caacactcaa ccctatctcg gtctattctt ttgatttata agggattttg gccatttcgg    4860
cctattggtt aaaaaatgag ctgatttaac aaaaatttaa cgcgaattaa ttctgtggaa    4920
tgtgtgtcag ttagggtgtg aaagtcccca aggctcccca gcaggcagaa gtatgcaaag    4980
catgcatctc aattagtcag caaccaggtg tggaaagtcc ccaggctccc cagcaggcag    5040
aagtatgcaa agcatgcatc tcaattagtc agcaaccata gtcccgcccc taactccgcc    5100 catccccgccc ctaactccgc ccagttccgc ccattctccg ccccatggct gactaatttt    5160
ttttatttat gcagaggccg aggccgcctc tgcctctgag ctattccaga agtagtgagg    5220 aggcttttt ggaggcctag gcttttgcaa aaagctcccg ggagcttgta tatccatttt    5280
cggatctgat cagcacgtga tgaaaaagcc tgaactcacc gcgacgtctg tcgagaagtt    5340
tctgatcgaa aagttcgaca gcgtctccga cctgatgcag ctctcggagg gcgaagaatc    5400
tcgtgctttc agcttcgatg taggagggcg tggatatgtc ctgcgggtaa atagctgcgc    5460
cgatggtttc tacaaagatc gttatgttta tcggcacttt gcatcggccg cgctcccgat    5520
tccggaagtg cttgacattg gggaattcag cgagagcctg acctattgca tctcccgccg    5580
tgcacagggt gtcacgttgc aagacctgcc tgaaaccgaa ctgcccgctg ttctgcagcc    5640
ggtcgcggag gccatggatg cgatcgctgc ggccgatctt agccagacga gcgggttcgg    5700
cccattcgga ccacaaggaa tcggtcaata cactacatgg cgtgatttca tatgcgcgat    5760
tgctgatccc catgtgtatc actggcaaac tgtgatggac gacaccgtca gtgcgtccgt    5820
cgcgcaggct ctcgatgagc tgatgctttg gccgaggac tgccccgaag tccggcacct    5880
cgtgcacgcg gatttcggct ccaacaatgt cctgacggac aatggccgca taacagcggt    5940
cattgactgg agcgaggcga tgttcgggga ttcccaatac gaggtcgcca acatcttctt    6000
ctggaggccg tggttggctt gtatggagca gcagacgcgc tacttcgagc ggaggcatcc    6060
ggagcttgca ggatcgccgc ggctccgggc gtatatgctc cgcattggtc ttgaccaact    6120
ctatcagagc ttggttgacg gcaatttcga tgatgcagct tgggcgcagg gtcgatgcga    6180
cgcaatcgtc cgatccggag ccgggactgt cgggcgtaca caaatcgccc gcagaagcgc    6240
```

```
ggccgtctgg accgatggct gtgtagaagt actcgccgat agtggaaacc gacgccccag   6300
cactcgtccg agggcaaagg aatagcacgt gctacgagat ttcgattcca ccgccgcctt   6360
ctatgaaagg ttgggcttcg gaatcgtttt ccgggacgcc ggctggatga tcctccagcg   6420
cggggatctc atgctggagt tcttcgccca ccccaacttg tttattgcag cttataatgg   6480
ttacaaataa agcaatagca tcacaaattt cacaaataaa gcattttttt cactgcattc   6540
tagttgtggt ttgtccaaac tcatcaatgt atcttatcat gtctgtatac cgtcgacctc   6600
tagctagagc ttggcgtaat catggtcata gctgtttcct gtgtgaaatt gttatccgct   6660
cacaattcca cacaacatac gagccggaag cataaagtgt aaagcctggg gtgcctaatg   6720
agtgagctaa ctcacattaa ttgcgttgcg ctcactgccc gctttccagt cgggaaacct   6780
gtcgtgccag ctgcattaat gaatcggcca acgcgcgggg agaggcggtt tgcgtattgg   6840
gcgctcttcc gcttcctcgc tcactgactc gctgcgctcg gtcgttcggc tgcggcgagc   6900
ggtatcagct cactcaaagg cggtaatacg gttatccaca gaatcagggg ataacgcagg   6960
aaagaacatg tgagcaaaag gccagcaaaa ggccaggaac cgtaaaaagg ccgcgttgct   7020
ggcgtttttc cataggctcc gcccccctga cgagcatcac aaaaatcgac gctcaagtca   7080
gaggtggcga aacccgacag gactataaag ataccaggcg tttccccctg gaagctccct   7140
cgtgcgctct cctgttccga ccctgccgct taccggatac ctgtccgcct ttctcccttc   7200
gggaagcgtg gcgctttctc atagctcacg ctgtaggtat ctcagttcgg tgtaggtcgt   7260
tcgctccaag ctgggctgtg tgcacgaacc ccccgttcag cccgaccgct gcgccttatc   7320
cggtaactat cgtcttgagt ccaacccggt aagacacgac ttatcgccac tggcagcagc   7380
cactggtaac aggattagca gagcgaggta tgtaggcggt gctacagagt tcttgaagtg   7440
gtggcctaac tacggctaca ctagaagaac agtatttggt atctgcgctc tgctgaagcc   7500
agttaccttc ggaaaaagag ttggtagctc ttgatccggc aaacaaacca ccgctggtag   7560
cggtttttt gtttgcaagc agcagattac gcgcagaaaa aaaggatctc aagaagatcc   7620
tttgatcttt tctacggggt ctgacgctca gtggaacgaa aactcacgtt aagggatttt   7680
ggtcatgaga ttatcaaaaa ggatcttcac ctagatcctt taaattaaa aatgaagttt   7740
taaatcaatc taaagtatat atgagtaaac ttggtctgac agttaccaat gcttaatcag   7800
tgaggcacct atctcagcga tctgtctatt tcgttcatcc atagttgcct gactccccgt   7860
cgtgtagata actacgatac gggagggctt accatctggc cccagtgctg caatgatacc   7920
gcgagaccca cgctcaccgg ctccagattt atcagcaata aaccagccag ccggaagggc   7980
cgagcgcaga agtggtcctg caactttatc cgcctccatc cagtctatta attgttgccg   8040
ggaagctaga gtaagtagtt cgccagttaa tagtttgcgc aacgttgttg ccattgctac   8100
aggcatcgtg gtgtcacgct cgtcgtttgg tatggcttca ttcagctccg gttcccaacg   8160
atcaaggcga gttacatgat cccccatgtt gtgcaaaaaa gcggttagct ccttcggtcc   8220
tccgatcgtt gtcagaagta agttggccgc agtgttatca ctcatggtta tggcagcact   8280
gcataattct cttactgtca tgccatccgt aagatgcttt tctgtgactg gtgagtactc   8340
aaccaagtca ttctgagaat agtgtatgcg gcgaccgagt tgctcttgcc cggcgtcaat   8400
acgggataat accgcgccac atagcagaac tttaaaagtg ctcatcattg gaaaacgttc   8460
ttcggggcga aaactctcaa ggatcttacc gctgttgaga tccagttcga tgtaacccac   8520
tcgtgcaccc aactgatctt cagcatcttt tactttcacc agcgtttctg ggtgagcaaa   8580
```

```
aacaggaagg caaaatgccg caaaaaaggg aataagggcg acacggaaat gttgaatact    8640
catactcttc cttttcaat attattgaag catttatcag ggttattgtc tcatgagcgg    8700
atacatattt gaatgtattt agaaaaataa acaaataggg gttccgcgca catttccccg    8760
aaaagtgcca cctgacg                                                  8777

<210> SEQ ID NO 177
<211> LENGTH: 8792
<212> TYPE: DNA
<213> ORGANISM: Artificial
<220> FEATURE:
<223> OTHER INFORMATION: Vector pIg-C910-Clambda

<400> SEQUENCE: 177
tcgacggatc gggagatctc ccgatcccct atggtgcact ctcagtacaa tctgctctga     60
tgccgcatag ttaagccagt atctgctccc tgcttgtgtg ttggaggtcg ctgagtagtg    120
cgcgagcaaa atttaagcta caacaaggca aggcttgacc gacaattgtt aattaacatg    180
aagaatctgc ttagggttag gcgttttgcg ctgcttcgct aggtggtcaa tattggccat    240
tagccatatt attcattggt tatatagcat aaatcaatat ggctattggc cattgcata    300 cgttgtatcc atatcataat atgtacattt atattggctc atgtccaaca ttaccgccat    360
gttgacattg attattgact agttattaat agtaatcaat tacggggtca ttagttcata    420
gcccatatat ggagttccgc gttacataac ttacggtaaa tggcccgcct ggctgaccgc    480
ccaacgaccc ccgcccattg acgtcaataa tgacgtatgt tcccatagta acgccaatag    540
ggactttcca ttgacgtcaa tgggtggagt atttacggta aactgcccac ttggcagtac    600
atcaagtgta tcatatgcca gtacgcccc ctattgacgt caatgacggt aaatggcccg    660
cctggcatta tgcccagtac atgaccttat gggactttcc tacttggcag tacatctacg    720
tattagtcat cgctattacc atggtgatgc ggttttggca gtacatcaat gggcgtggat    780
agcggtttga ctcacgggga tttccaagtc tccaccccat tgacgtcaat gggagtttgt    840
tttggcacca aaatcaacgg gactttccaa aatgtcgtaa caactccgcc ccattgacgc    900
aaatgggcgg taggcgtgta cggtgggagg tctatataag cagagctcgt ttagtgaacc    960
gtcagatcgc ctggagacgc catccacgct gttttgacct ccatagaaga caccgggacc   1020
gatccagcct ccgcggccgg gaacggtgca ttggaatcga tgactctctt aggtagcctt   1080
gcagaagttg gtcgtgaggc actgggcagg taagtatcaa ggttacaaga caggtttaag   1140
gagatcaata gaaactgggc ttgtcgagac agagaagact cttgcgtttc tgataggcac   1200
ctattggtct tactgacatc cactttgcct ttctctccac aggtgtccac tcccagttca   1260
attacagctc gccaccatgc ggttctccgc tcagctgctg gccttctgg tgctgtggat   1320 tcccggcgtc tcgagatcta tcgatgcatg ccatggtacc aagcttgcca ccatgagcag   1380
cagctcttgg ctgctgctga gcctggtggc cgtgacagcc gcccagagca ccatcgagga   1440
gcaggccaag accttcctgg acaagttcaa ccacgaggcc gaggacctgt ctaccagag   1500 cagcctggcc agctggaact acaacaccaa catcaccgag gagaacgtgc agaacatgaa   1560
caacgccggc gacaagtgga gcgccttcct gaaggagcag agcacactgg cccagatgta   1620
ccccctgcag gagatccaga acctgaccgt gaagctgcag ctgcaggccc tgcagcagaa   1680
cggcagcagc gtgctgagcg aggacaagag caagcggctg aacaccatcc tgaacaccat   1740
gtccaccatc tacagcaccg gcaaagtgtg caacccccga accccccagg agtgcctgct   1800
gctggagccc ggcctgaacg agatcatggc caacagcctg gactacaacg agcggctgtg   1860
```

```
ggcctgggag agctggcgga gcgaagtggg caagcagctg cggcccctgt acgaggagta   1920
cgtggtgctg aagaacgaga tggccagggc caaccactac gaggactacg gcgactactg   1980
gagaggcgac tacgaagtga acggcgtgga cggctacgac tacagcagag gccagctgat   2040
cgaggacgtg gagcacacct tcgaggagat caagcctctg tacgagcacc tgcacgccta   2100
cgtgcgggcc aagctgatga acgcctaccc cagctacatc agcccatcg gctgcctgcc   2160 cgcccacctg ctgggcgaca tgtggggccg gttctggacc aacctgtaca gcctgaccgt   2220
gcccttcggc cagaagccca acatcgacgt gaccgacgcc atggtggacc aggcctggga   2280
cgcccagcgg atcttcaagg aggccgagaa gttcttcgtg agcgtgggcc tgcccaacat   2340
gacccagggc tttgggagga cagcatgct gaccgacccc ggcaatgtgc agaaggccgt   2400
gtgccacccc accgcctggg acctgggcaa gggcgacttc cggatcctga tgtgcaccaa   2460
agtgaccatg gacgacttcc tgaccgccca ccacgagatg ggccacatcc agtacgacat   2520
ggcctacgcc gcccagccct tcctgctgcg gaacggcgcc aacgagggct tcacgaggc   2580 cgtgggcgag atcatgagcc tgagcgccgc caccccaag cacctgaaga gcatcggcct   2640
gctgagcccc gacttccagg aggacaacga gaccgagatc aacttcctgc tgaagcaggc   2700
cctgaccatc gtgggcaccc tgccttcac ctacatgctg gagaagtggc ggtggatggt   2760
gtttaagggc gagatcccca aggaccagtg gatgaagaag tggtgggaga tgaagcggga   2820
gatcgtgggc gtggtggagc ccgtgcccca cgacgagacc tactgcgacc ccgccagcct   2880
gttccacgtg agcaacgact actccttcat ccggtactac acccggaccc tgtaccagtt   2940
ccagttccag gaggccctgt gccaggccgc caagcacgag ggcccccctgc acaagtgcga   3000 catcagcaac agcaccgagg ccggacagaa actgttcaac atgctgcggc tgggcaagag   3060
cgagccctgg accctggccc tggagaatgt ggtgggcgcc aagaacatga atgtgcgccc   3120
cctgctgaac tacttcgagc ccctgttcac ctggctgaag gaccagaaca gaacagctt   3180 cgtgggctgg agcaccgact ggagccccta cgccgaccag agcatcaaag tgcggatcag   3240
cctgaagagc gccctgggcg acaaggccta cgagtggaac gacaacgaga tgtacctgtt   3300
ccggagcagc gtggcctatg ccatgcggca gtacttcctg aaagtgaaga accagatgat   3360
cctgttcggc gaggaggacg tgagagtggc caacctgaag ccccggatca gcttcaactt   3420
cttcgtgacc gcccccaaga acgtgagcga catcatcccc cggaccgaag tggagaaggc   3480
catccggatg agccggagcc ggatcaacga cgccttccgg ctgaacgaca actccctgga   3540
gttcctgggc atccagccca ccctgggccc tccaaccag ccccccgtga gcatctggct   3600
gatcgtgttt ggcgtggtga tgggcgtgat cgtggtggga atcgtgatcc tgatcttcac   3660
cggcatccgg gaccggaaga gaagaacaa ggcccggagc ggcgagaacc cctacgccag   3720
catcgatatc agcaagggcg agaacaaccc cggcttccag aacaccgacg acgtgcagac   3780
cagcttctga taatctagaa cgagctcgaa ttcgaagctt ctgcagacgc gtcgacgtca   3840
tatggatccg atatcgccgt ggcggccgca ggccagccca aggccgctcc cagcgtgacc   3900
ctgttccccc cctcctccga ggagctgcag gccaacaagg ccaccctggt gtgcctcatc   3960
agcgacttct acccctggcgc cgtgaccgtg gcctggaagg ccgacagcag ccccgtgaag   4020
gccggcgtgg agaccaccac ccccagcaag cagagcaaca acaagtacgc cgccagcagc   4080
tacctgagcc tcaccccga gcagtggaag agccaccgga gctacagctg ccaggtgacc   4140
cacgagggca gcaccgtgga gaagaccgtg gccccaccg agtgcagcta atagacttaa   4200
```

```
gtttaaaccg ctgatcagcc tcgactgtgc cttctagttg ccagccatct gttgtttgcc      4260
cctcccccgt gccttccttg accctggaag gtgccactcc cactgtcctt tcctaataaa      4320
atgaggaaat tgcatcgcat tgtctgagta ggtgtcattc tattctgggg ggtggggtgg      4380
ggcaggacag caaggggag gattgggaag acaatagcag gcatgctggg gatgcggtgg       4440
gctctatggc ttctgaggcg gaaagaacca gctgggctc taggggtat ccccacgcgc        4500 cctgtagcgg cgcattaagc gcggcgggtg tggtggttac gcgcagcgtg accgctacac      4560
ttgccagcgc cctagcgccc gctcctttcg ctttcttccc ttcctttctc gccacgttcg      4620
ccggctttcc ccgtcaagct ctaaatcggg gctcccttt aggggttccga tttagtgctt     4680 tacggcacct cgaccccaaa aaacttgatt agggtgatgg ttcacgtagt gggccatcgc      4740
cctgatagac ggttttttcgc cctttgacgt tggagtccac gttctttaat agtggactct     4800
tgttccaaac tggaacaaca ctcaacccta tctcggtcta ttcttttgat ttataaggga      4860
ttttggccat ttcggcctat tggttaaaaa atgagctgat ttaacaaaaa tttaacgcga      4920
attaattctg tggaatgtgt gtcagttagg gtgtggaaag tccccaggct ccccagcagg      4980
cagaagtatg caaagcatgc atctcaatta gtcagcaacc aggtgtggaa agtccccagg      5040 ctcccccagca ggcagaagta tgcaaagcat gcatctcaat tagtcagcaa ccatagtccc    5100
gcccctaact ccgcccatcc cgcccctaac tccgcccagt tccgcccatt ctccgcccca      5160
tggctgacta ttttttttta tttatgcaga ggccgaggcc gcctctgcct ctgagctatt      5220
ccagaagtag tgaggaggct ttttggagg cctaggcttt tgcaaaaagc tcccgggagc       5280
ttgtatatcc attttcggat ctgatcagca cgtgatgaaa aagcctgaac tcaccgcgac      5340
gtctgtcgag aagtttctga tcgaaaagtt cgacagcgtc tccgacctga tgcagctctc      5400
ggagggcgaa gaatctcgtg ctttcagctt cgatgtagga gggcgtggat atgtcctgcg     5460
ggtaaatagc tgcgccgatg gtttctacaa agatcgttat gtttatcggc actttgcatc     5520
ggccgcgctc ccgattccgg aagtgcttga cattggggaa ttcagcgaga gcctgaccta    5580
ttgcatctcc cgccgtgcac agggtgtcac gttgcaagac ctgcctgaaa ccgaactgcc      5640
cgctgttctg cagccggtcg cggaggccat ggatgcgatc gctgcggccg atcttagcca      5700
gacgagcggg ttcggcccat tcggaccgca aggaatcggt caatacacta catggcgtga     5760
tttcatatgc gcgattgctg atccccatgt gtatcactgg caaactgtga tggacgacac      5820
cgtcagtgcg tccgtcgcgc aggctctcga tgagctgatg ctttgggccg aggactgccc      5880
cgaagtccgg cacctcgtgc acgcggattt cggctccaac aatgtcctga cggacaatgg      5940
ccgcataaca gcggtcattg actggagcga ggcgatgttc ggggattccc aatacgaggt      6000
cgccaacatc ttcttctgga ggccgtggtt ggcttgtatg gagcagcaga cgcgctactt      6060
cgagcggagg catccggagc ttgcaggatc gccgcggctc cgggcgtata tgctccgcat     6120
tggtcttgac caactctatc agagcttggt tgacggcaat ttcgatgatg cagcttgggc      6180
gcagggtcga tgcgacgcaa tcgtccgatc cggagccggg actgtcgggc gtacacaaat     6240
cgcccgcaga agcgcggccg tctggaccga tggctgtgta agtactcg ccgatagtgg        6300 aaaccgacgc cccagcactc gtccgagggc aaaggaatag cacgtgctac gagatttcga     6360
ttccaccgcc gccttctatg aaaggttggg cttcggaatc gttttccggg acgccggctg      6420
gatgatcctc cagcgcgggg atctcatgct ggagttcttc gcccacccca acttgtttat      6480
tgcagcttat aatggttaca aataaagcaa tagcatcaca aatttcacaa ataaagcatt      6540 ttttttcactg cattctagtt gtggtttgtc caaactcatc aatgtatctt atcatgtctg      6600
```

```
tataccgtcg acctctagct agagcttggc gtaatcatgg tcatagctgt ttcctgtgtg   6660
aaattgttat ccgctcacaa ttccacacaa catacgagcc ggaagcataa agtgtaaagc   6720
ctggggtgcc taatgagtga gctaactcac attaattgcg ttgcgctcac tgcccgcttt   6780
ccagtcggga aacctgtcgt gccagctgca ttaatgaatc ggccaacgcg cggggagagg   6840
cggtttgcgt attgggcgct cttccgcttc ctcgctcact gactcgctgc gctcggtcgt   6900
tcggctgcgg cgagcggtat cagctcactc aaaggcggta atacggttat ccacagaatc   6960
aggggataac gcaggaaaga acatgtgagc aaaaggccag caaaaggcca ggaaccgtaa   7020
aaaggccgcg ttgctggcgt ttttccatag gctccgcccc cctgacgagc atcacaaaaa   7080
tcgacgctca agtcagaggt ggcgaaaccc gacaggacta taaagatacc aggcgtttcc   7140
ccctggaagc tccctcgtgc gctctcctgt tccgaccctg ccgcttaccg gatacctgtc   7200
cgcctttctc ccttcgggaa gcgtggcgct ttctcatagc tcacgctgta ggtatctcag   7260
ttcggtgtag gtcgttcgct ccaagctggg ctgtgtgcac gaaccccccg ttcagcccga   7320
ccgctgcgcc ttatccggta actatcgtct tgagtccaac ccggtaagac acgacttatc   7380
gccactggca gcagccactg gtaacaggat tagcagagcg aggtatgtag gcggtgctac   7440
agagttcttg aagtggtggc ctaactacgg ctacactaga agaacagtat ttggtatctg   7500
cgctctgctg aagccagtta ccttcggaaa aagagttggt agctcttgat ccggcaaaca   7560
aaccaccgct ggtagcggtt ttttgtttg caagcagcag attacgcgca gaaaaaaagg   7620
atctcaagaa gatcctttga tcttttctac ggggtctgac gctcagtgga acgaaaactc   7680
acgttaaggg attttggtca tgagattatc aaaaaggatc ttcacctaga tccttttaaa   7740
ttaaaaatga agttttaaat caatctaaag tatatatgag taaacttggt ctgacagtta   7800
ccaatgctta atcagtgagg cacctatctc agcgatctgt ctatttcgtt catccatagt   7860
tgcctgactc cccgtcgtgt agataactac gatacgggag gcttaccat ctggccccag    7920
tgctgcaatg ataccgcgag acccacgctc accggctcca gatttatcag caataaacca   7980
gccagccgga agggccgagc gcagaagtgg tcctgcaact ttatccgcct ccatccagtc   8040
tattaattgt tgccgggaag ctagagtaag tagttcgcca gttaatagtt tgcgcaacgt   8100
tgttgccatt gctacaggca tcgtggtgtc acgctcgtcg tttggtatgg cttcattcag   8160
ctccggttcc caacgatcaa ggcgagttac atgatccccc atgttgtgca aaaaagcggt   8220
tagctccttc ggtcctccga tcgttgtcag aagtaagttg gccgcagtgt tatcactcat   8280
ggttatggca gcactgcata attctcttac tgtcatgcca tccgtaagat gcttttctgt   8340
gactggtgag tactcaacca agtcattctg agaatagtgt atgcggcgac cgagttgctc   8400
ttgcccggcg tcaatacggg ataataccgc gccacatagc agaactttaa aagtgctcat   8460
cattggaaaa cgttcttcgg ggcgaaaact ctcaaggatc ttaccgctgt tgagatccag   8520
ttcgatgtaa cccactcgtg cacccaactg atcttcagca tcttttactt tcaccagcgt   8580
ttctgggtga gcaaaaacag gaaggcaaaa tgccgcaaaa aagggaataa gggcgacacg   8640
gaaatgttga atactcatac tcttcctttt tcaatattat tgaagcattt atcagggtta   8700
ttgtctcatg agcggataca tatttgaatg tatttagaaa aataaacaaa tagggggttcc   8760
gcgcacattt ccccgaaaag tgccacctga cg                                 8792
```